(12) United States Patent
Wagoner et al.

(10) Patent No.: US 10,524,455 B2
(45) Date of Patent: Jan. 7, 2020

(54) METHODS AND COMPOSITIONS FOR INDUCING HYGIENIC BEHAVIOR IN HONEY BEES

(71) Applicant: University of North Carolina at Greensboro, Greensboro, NC (US)

(72) Inventors: Kaira Wagoner, Greensboro, NC (US); Olav Rueppell, Greensboro, NC (US)

(73) Assignee: University of North Carolina at Greensboro, Greensboro, NC (US)

(*) Notice: Subject to any disclaimer, the term of this patent is extended or adjusted under 35 U.S.C. 154(b) by 0 days.

(21) Appl. No.: 16/279,432

(22) Filed: Feb. 19, 2019

(65) Prior Publication Data
US 2019/0357501 A1    Nov. 28, 2019

Related U.S. Application Data

(62) Division of application No. 15/742,072, filed as application No. PCT/US2016/040993 on Jul. 5, 2016.

(60) Provisional application No. 62/188,991, filed on Jul. 6, 2015.

(51) Int. Cl.
*A61K 31/00* (2006.01)
*A01K 51/00* (2006.01)

(52) U.S. Cl.
CPC .............. *A01K 51/00* (2013.01); *A61K 31/00* (2013.01)

(58) Field of Classification Search
CPC ..................................................... A61K 31/00
See application file for complete search history.

(56) References Cited

U.S. PATENT DOCUMENTS

| 7,049,373 | B2 | 5/2006 | Matyjaszewski et al. |
| 7,666,057 | B2 | 2/2010 | Junqueira de Souza et al. |
| 7,816,441 | B2 | 10/2010 | Elizalde et al. |
| 7,922,559 | B2 | 4/2011 | Cook |
| 2002/0182977 | A1 | 12/2002 | Page, Jr. et al. |
| 2007/0026765 | A1 | 2/2007 | Renn |
| 2009/0036551 | A1 | 2/2009 | Venkatesh et al. |
| 2009/0104288 | A1 | 4/2009 | Probasco |
| 2009/0169893 | A1 | 7/2009 | Ikegami et al. |
| 2009/0275681 | A1 | 11/2009 | Venkatesh |
| 2010/0069597 | A1 | 3/2010 | Venkatesh et al. |

(Continued)

FOREIGN PATENT DOCUMENTS

| CN | 103875549 A | 6/2014 |
| DE | 102005010137 A1 | 9/2006 |
| DE | 102012022345 A1 | 5/2014 |

(Continued)

OTHER PUBLICATIONS

Richards, BMC Biology 2008, 6:50. (Year: 2008).*

(Continued)

*Primary Examiner* — Benjamin J Packard
(74) *Attorney, Agent, or Firm* — Julia A. Kim; In Vivo Patent Law

(57) ABSTRACT

The presently disclosed subject matter provides tritriacontene compositions for inducing hygienic behavior in honey bees; mite-infested brood extract compositions for inducing hygienic behavior in honey bees; methods of inducing hygienic behavior in honey bees; methods of selecting one or more honey bee(s) exhibiting hygienic behavior, and methods for assessing the degree of hygienic behavior within a honey bee colony.

64 Claims, 17 Drawing Sheets

Specification includes a Sequence Listing.

(56) References Cited

U.S. PATENT DOCUMENTS

2010/0234506 A1  3/2010  Venkatesh et al.

FOREIGN PATENT DOCUMENTS

| FR | 2668332 A1 | 4/1992 |
|---|---|---|
| GR | 1004165 B | 2/2003 |
| KR | 2012129044 A | 11/2012 |
| RO | 116148 B | 11/2000 |
| RS | 83504 A | 2/2007 |
| RU | 2534586 C2 | 11/2014 |
| WO | 2005018313 A1 | 3/2005 |
| WO | 2011097749 A1 | 8/2011 |

OTHER PUBLICATIONS

Nojima, Satoshi et al., "A Simple, Convenient, and Efficient Preparative GC System that Uses a Short Megabore Capillary Column as a Trap," Journal of Chemical Ecology, vol. 34, Issue 3, Mar. 2008, Springer, pp. 418-428.

Nojima, Satoshi et al., "Identification of the Sex Pheromone of the German Cockroach, *Blattella germanica*," Science, vol. 307, Issue 5712, Feb. 18, 2005, American Association for the Advancement of Science, pp. 1104-1106.

Oldroyd, Benjamin P. et al., "Genetic diversity promotes homeostasis in insect colonies," TRENDS in Ecology and Evolution, vol. 22, Issue 8, Jun. 18, 2007, Elsevier Ltd., pp. 408-413.

Otvos, Laszlo Jr. et al., "Interaction between Heat Shock Proteins and Antimicrobial Peptides," Biochemistry, vol. 39, Issue 46, Nov. 21, 2000, American Chemical Society, pp. 14150-14159.

Oxley, Peter R. et al., "Six quantitative trait loci influence task thresholds for hygienic behaviour in honeybees (*Apis mellifera*)," Molecular Ecology, vol. 19, Issue 7, Apr. 2010, Blackwell Publishing Ltd., pp. 1452-1461.

Parker, Robert et al., "Correlation of proteome-wide changes with social immunity behaviors provides insight into resistance to the parasitic mite, *Varroa destructor*, in the honey bee (*Apis mellifera*)," Genome Biology, vol. 13, Issue 9, Sep. 28, 2012, BioMed Central Ltd., 46 pages.

Peng, Ying-Shen et al., "The Resistance Mechanism of the Asian Honey Bee, *Apis cerana* Fabr., to an Ectoparasitic Mite, *Varroa jacobsoni oudemans*," Journal of Invertebrate Pathology, vol. 49, Issue 1, 1987, Academic Press, Inc., pp. 54-60.

Pepke, Shirley et al., "Computation for ChIP-seq and RNA-seq studies," Nature Methods, vol. 6, Issue 11s, Nov. 2009, Nature Publishing Group, pp. 1-25.

Pernal, Stephen F. et al., "Breeding for hygienic behaviour in honeybees (*Apis mellifera*) using free-mated nucleus colonies," Apidologie, vol. 43, Issue 4, Jul. 2012, INRA, DIB and Springer-Verlag, pp. 403-416.

Pettis, Jeffery S. et al., "Effects of coumaphos on queen rearing in the honey bee, *Apis mellifera*," Apidologie, vol. 35, Issue 6, Nov. 2004, INRA/DIB-AGIB/ EDP Sciences, pp. 605-610.

Pettis, Jeffery S. et al., "Pesticide exposure in honey bees results in increased levels of the gut pathogen Nosema," Naturwissenschaften, vol. 99, Issue 2, Jan. 13, 2012, Springerlink, pp. 153-158.

Podgwaite, J. D. et al., "Latency of Insect Viruses," Advances in Virus Research, vol. 31, 1986, Academic Press, Inc., pp. 293-320.

Potts, Simon G. et al., "Global pollinator declines: trends, impacts and drivers," Trends in Ecology and Evolution, vol. 25, Issue 6, Feb. 24, 2010, Elsevier Ltd., pp. 345-353.

Principal De D'Aubeterre, Judith et al., "A scientific note of an application of isotope ratio mass spectrometry to feeding by the mite, *Varroa jacobsoni oudemans*, on the honeybee, *Apis mellifera* L.," Apidologie, vol. 30, Issue 4, 1999, Springer Verlag, pp. 351-352.

Rademacher, Eva et al., "Oxalic acid for the control of varroosis in honey bee colonies—a review," Apidologie, vol. 37, Issue 1, 2006, INRA/DIB-AGIB/ EDP Sciences, pp. 98-120.

Richard, F-J et al., "Modulation of social interactions by immune stimulation in honey bee, *Apis mellifera*, workers," BMC Biology, vol. 6, Issue 1, Nov. 17, 2008, BioMed Central Ltd., pp. 1-13.

Rinderer, Thomas E. et al., "Breeding for resistance to Varroa destructor in North America," Apidologie, vol. 41, Issue 3, May 2010, INRA/DIB-AGIB/EDP Sciences, pp. 409-424.

Rosenkranz, Peter et al., "Biology and control of Varroa destructor," Journal of Invertebrate Pathology, vol. 103, Nov. 11, 2009, Elsevier Inc., pp. S96-S119.

Rosenkranz, Peter et al., "Differential hygienic behavior towards Varroa jacobsoni in capped worker brood of Apis cerana depends on alien scent adhering to the mites," Journal of Apicultural Research, vol. 32, Issue 2, 1993, IBRA, pp. 89-93.

Rothenbuhler, Walter C., "Behavior Genetics of Nest Cleaning in Honey Bees. IV. Responses of F1 and Backcross Generations to Disease-Killed Brood," American Zoologist, vol. 4, Issue 2, May 1964, Oxford University Press, pp. 111-123.

Runckel, Charles et al., "Temporal Analysis of the Honey Bee Microbiome Reveals Four Novel Viruses and Seasonal Prevalence of Known Viruses, Nosema, and Crithidia," PLoS ONE, vol. 6, Issue 6, Jun. 7, 2011, www.plosone.org, pp. 1-18.

Rueppel, O. et al. "Altruistic self-removal of health-compromised honey bee workers from their hive," Journal of Evolutionary Biology, vol. 23, Issue 7, Jul. 2010, European Society for Evolutionary Biology, pp. 1538-1546.

Ryabov, Eugene V. et al., "A Virulent Strain of Deformed Wing Virus (DWV) of Honeybees (*Apis mellifera*) Prevails after Varroa destructor-Mediated, or In Vitro, Transmission," PLOS Pathogens, vol. 10, Issue 6, Jun. 26, 2014, www.plospathogens.org, pp. 1-21.

Salvy, M. et al., "Modifications of the cuticular hydrocarbon profile of Apis mellifera worker bees in the presence of the ectoparasitic mite *Varroa jacobsoni* in brood cells," Parasitology, vol. 122, Issue 2, Feb. 2001, Cambridge University Press, pp. 145-159.

Sammataro, Diana et al., "Parasitic Mites of Honey Bees: Life History, Implications, and Impact," Annual Review of Entomology, vol. 45, 2000, Annual Reviews, pp. 519-548.

Sammataro, Diana et al., "The Resistance of Varroa Mites (Acari: Varroidae) to Acaricides and the Presence of Esterase," International Journal of Acarology, vol. 31, Issue 1, 2005, Taylor & Francis, pp. 67-74.

Schöning, Caspar et al., "Evidence for damage-dependent hygienic behaviour towards Varroa destructorparasitised brood in the western honey bee, *Apis mellifera*," The Journal of Experimental Biology, vol. 215, Issue 2, 2012, The Company of Biologists Ltd., pp. 264-271.

Seeley, Thomas D. et al., "Honey bees of the Arnot Forest: a population of feral colonies persisting with Varroa destructor in the northeastern United States," Apidologie, vol. 38, Issue 1, 2007, EDP Sciences, pp. 19-29.

Seeley, Thomas D. et al., "Queen promiscuity lowers disease within honeybee colonies," Proceedings of the Royal Society B, vol. 274, Issue 1606, Sep. 26, 2006, The Royal Society, pp. 67-72.

Severson, D.W. et al., "Heat stress induced enhancement of heat shock protein gene activity in the honey bee (*Apis mellifera*)," Experientia, vol. 46, Issue 7, Jul. 1990, Birkhäuser Verlag Basel, pp. 737-739.

Shelton, Daniel R. et al., "Isolation and Characterization of Coumaphos-Metabolizing Bacteria from Cattle Dip," Applied and Environmental Microbiology, vol. 54, Issue 10, Oct. 1988, American Society for Microbiology, pp. 2566-2571.

Singh, Rajwinder et al., "RNA Viruses in Hymenopteran Pollinators: Evidence of Inter-Taxa Virus Transmission via Pollen and Potential Impact on Non-*Apis Hymenopteran* Species," PLoS ONE, vol. 5, Issue 12, Dec. 22, 2010, www.plosone.org, pp. 1-16.

Slessor, Keith N. et al., "Pheromone Communication in the Honeybee," Journal of Chemical Ecology, vol. 31, Issue 11, Nov. 2005, Springer Science + Business Media, Inc., pp. 2731-2745.

Smet, Lina De et al., "BeeDoctor, a Versatile MLPA-Based Diagnostic Tool for Screening Bee Viruses," PLOS ONE, vol. 7, Issue 10, Oct. 2012, www.plosone.org, pp. 1-8.

(56) References Cited

OTHER PUBLICATIONS

Sonnet, P.E. et al., "Sex Pheromone of the Stable Fly: Identification, Synthesis, and Evaluation of Alkenes from Female Stable Flies," Journal of Chemical Ecology, vol. 5, Issue 3, May 1979, Springer US, pp. 353-361.
Spivak, Marla et al., "Field Assays for Hygienic Behavior in Honey Bees (Hymenoptera: Apidae)," Journal of Economic Entomology, vol. 91, Issue 1, Feb. 1, 1998, EntomologicalSociety of America, pp. 64-70.
Spivak, Marla, "Honey bee hygienic behavior and defense against Varroa jacobsoni," Apidologie, vol. 27, Issue 4, Aug. 14, 1996, Springer Verlag, pp. 245-260.
Spivak, Marla et al., "Hygienic Behavior in the Honey Bee (*Apis mellifera* L.) and the Modulatory Role of Octopamine," Developmental Neurobiology, vol. 55, Issue 3, Jun. 2003, Wiley Periodicals, Inc., pp. 341-354.
Spivak, Marla et al., "Hygienic behaviour of honey bees and its application for control of brood diseases and varroa," Bee World, vol. 79, Issue 4, 1998, IBRA, pp. 169-186.
Spivak, Marla et al., "New Direction for the Minnesota Hygienic Line of Bees," American Bee Journal, vol. 148, Issue 12, Dec. 2008, pp. 1085-1086.
Spivak, Marla et al., "Performance of hygienic honey bee colonies in a commercial apiary," Apidologie, vol. 29, Issue 3, 1998, Springer Verlag, pp. 291-302.
Spivak, Marla et al., "The Plight of the Bees," Environmental Science & Technology, vol. 45, Issue 1, Sep. 14, 2010, American Chemical Society, pp. 34-38.
Spivak, Marla et al., "Resistance to American foulbrood disease by honey bee colonies *Apis mellifera* bred for hygienic behavior," Apidologie, vol. 32, Issue 6, Nov.-Dec. 2001, INRA/DIB-AGIB/EDP Sciences, pp. 555-565.
Spivak, Marla et al., "Varroa destructor Infestation in Untreated Honey Bee (Hymenoptera: Apidae) Colonies Selected for Hygienic Behavior," Journal of Economic Entomology, vol. 94, Issue 2, Apr. 2001, Entomological Society of America, pp. 326-331.
Spleen, Angela M. et al., "A national survey of managed honey bee 2011-12 winter colony losses in the United States: results from the Bee Informed Partnership," Journal of Apicultural Research, vol. 52, Issue 2, 2013, IBRA, pp.44-53.
Spotter, A. et al., "Development of a 44K SNP assay focussing on the analysis of a varroa-specific defence behaviour in honey bees (*Apis mellifera camica*)," Molecular Ecology Resources, vol. 12, Issue 2, Mar. 2012, Blackwell Publishing Ltd., pp. 323-332.
Steinhauer, N. A. et al., "A national survey of managed honey bee 2012-2013 annual colony losses in the USA: results from the Bee Informed Partnership," Journal of Apicultural Research, vol. 53, Issue 1, Feb. 2014, IBRA, pp. 1-18.
Swanson, Jodi A. I. et al., Odorants that Induce Hygienic Behavior in Honeybees: Identification of Volatile Compounds in Chalkbrood-Infected Honeybee Larvae, Journal of Chemical Ecology, vol. 35, Issue 9, Sep. 8, 2009, Springer Science + Business Media, LLC., pp. 1108-1116.
Sylevester, H. Allen et al., "Varroa in the Mating Yard: II. The Effects of Varroa and Fluvalinate on Drone Mating Competitiveness," American Bee Journal, vol. 139, Issue 2, Mar. 1999, American Bee Journal, pp. 225-227.
Torto, Baldwyn et al., "Standard methods for chemical ecology research in Apis mellifera," Journal of Apicultural Research, vol. 52, Issue 4, 2013, IBRA, pp. 1-35.
De Jong, D. et al., "Weight loss and other damage to developing worker honeybees from infestation with Varroa Jacobsoni," Journal of Apicultural Research, vol. 21, Issue 3, 1982, Taylor & Francis, pp. 165-167.
Dekeyser, Mark A. et al., "Biochemical and Physiological Targets for Miticides," Pesticide Science, vol. 40, Issue 2, 1994, SCI, pp. 85-101.
Delaplane, Keith S. et al., "Standard methods for estimating strength parameters of Apis mellifera colonies," Journal of Apicultural Research, vol. 52, Issue 1, Oct. 22, 2012, IBRA, pp. 1-12.

De Miranda, Joachim R. et al., "Standard methods for virus research in Apis mellifera," Journal of Apicultural Research, vol. 52, Issue 4, 2013, IBRA, pp. 1-55.
Desai, S. D. et al., "Reduction in deformed wing virus infection in larval and adult honey bees (*Apis mellifera* L.) by double-stranded RNA ingestion," Insect Molecular Biology, vol. 21, Issue 4, Jun. 12, 2012, The Royal Entomological Society, pp. 446-455.
Desneux, Nicolas et al., "The Sublethal Effects of Pesticides on Beneficial Arthropods," Annual Review of Entomology, vol. 52, 2007, Annual Reviews, pp. 81-106.
Dietemann, Vincent et al., "Standard methods for varroa research," Journal of Apicultural Research, vol. 52, Issue 1, Nov. 14, 2012, IBRA, pp. 1-54.
Dietemann, Vincent et al., "Varroa destructor: research avenues towards sustainable control," Journal of Apicultural Research, vol. 51, Issue 1, Dec. 20, 2011, IBRA, pp. 125-132.
Di Prisco, Gennaro et al., "Dynamics of Persistent and Acute Deformed Wing Virus Infections in Honey Bees, *Apis mellifera*," Viruses, vol. 3, Issue 12, Dec. 14, 2011, http://www.mdpi.com/journal/viruses, pp. 2425-2441.
Di Prisco, Gennaro et al., "Varroa destructor is an effective vector of Israeli acute paralysis virus in the honeybee, *Apis mellifera*," Journal of General Virology, vol. 92, 2011, Microbiology Society, pp. 151-155.
Dunkelblum, E. et al., "Double-bond Location in Monounsaturated Fatty Acids by Dimethyl Disulfide Derivatization and Mass Spectrometry: Application to Analysis of Fatty Acids in Pheromone Glands of Four Lepidoptera," Journal of Chemical Ecology, vol. 11, Issue 3, 1985, Plenum Publishing Corporation, pp. 265-277.
Eliyahu, Dorit et al., "Unusual macrocyclic lactone sex pheromone of Parcoblatta lata, a primary food source of the endangered red-cockaded woodpecker," Proceedings of the National Academy of Sciences (PNAS), vol. 109, Issue 8, Feb. 2012, National Academy of Sciences, pp. E490-E496.
Elsik, Christine G. et al., "Finding the missing honey bee genes: lessons learned from a genome upgrade," BMC Genomics, vol. 15, Issue 86, 2014, BioMed Central, http://www.biomedcentral.com/1471-2164/15/86, pp. 1-29.
Espinosa-Montaño, Laura G. et al. "Comparative study of three assays to evaluate hygienic behavior in honey bee (*Apis meiiifera* L.) colonies," Veterinaria Mexico, vol. 39, Issue 1, Mar. 2008, Universidad Nacional Autonoma de Mexico, pp. 39-53.
Evans, Jay D., "Beepath: An ordered quantitative-PCR array for exploring honey bee immunity and disease," Journal of Invertebrate Pathology, vol. 93, Issue 2, Oct. 2006, Elsevier Inc., pp. 135-139.
Evans, Jay D., "Diverse origins of tetracycline resistance in the honey bee bacterial pathogen Paenibacillus larvae," Journal of Invertebrate Pathology, vol. 83, Issue 1, May 2003, Elsevier Science, pp. 46-50.
Evans, J.D. et al., "Immune pathways and defence mechanisms in honey bees *Apis mellifera*," Insect Molecular Biology, vol. 15, Issue 5, Oct. 2006, The Royal Entomological Society, pp. 645-656.
Fakhimzadeh, Kamran, "Effectiveness of confectioner sugar dusting to knock down Varroa destructor from adult honey bees in laboratory trials," Apidologie, vol. 32, Issue 2, Mar.-Apr. 2001, INRA/DIB-AGIB/EDP Sciences, pp. 139-148.
Ferreira-Caliman, M.J. et al., "Analysis of Insect Cuticular Compounds by Non-lethal Solid Phase Micro Extraction with Styrene-Divinylbenzene Copolymers," Journal of Chemical Ecology, vol. 38, Issue 4, Apr. 2012, Springer Science+Business Media, LLC, pp. 418-426.
Flenniken, Michelle L. et al., "Non-Specific dsRNA-Mediated Antiviral Response in the Honey Bee," PLoS ONE, vol. 8, Issue 10, Oct. 10, 2013, www.plosone.org, pp. 1-16.
Forkpah, Cordelia et al., "Xenobiotic Effects on Intestinal Stem Cell Proliferation in Adult Honey Bee (*Apis mellifera* L.) Workers," PLoS ONE, vol. 9, Issue 3, Mar. 7, 2014, www.plosone.org, 9 pages.
Frazier, Maryann et al., "What Have Pesticides Got to Do with It?" American Bee Journal, vol. 148, Issue 6, Jun. 2008, American Bee Journal, pp. 1-5.

(56) References Cited

OTHER PUBLICATIONS

Frey, Eva et al., "Activation and interruption of the reproduction of Varroa destructor is triggered by host signals (Apis mellifera)," Journal of Invertebrate Pathology, vol. 113, Issue 1, May 2013, Elsevier Inc., pp. 56-62.
Furman, David et al., "Cytomegalovirus infection improves immune responses to influenza," Science Translational Medicine, vol. 7, Issue 281, Apr. 1, 2015, American Association for the Advancement of Science, pp. 1-22.
Galbraith, David A. et al., "Parallel Epigenomic and Transcriptomic Responses to Viral Infection in Honey Bees (Apis mellifera)," PLOS Pathogens, vol. 11, Issue 3, Mar. 26, 2015, https://www.ncbi.nlm.nih.gov/pmc/articles/PMC4374888/, pp. 1-24.
Garbian, Yael et al., "Bidirectional Transfer of RNAi between Honey Bee and Varroa destructor: Varroa Gene Silencing Reduces Varroa Population," PLOS Pathogens, vol. 8, Issue 12, Dec. 2012, www.plospathogens.org, pp. 1-9.
Garedew, Assegid et al., "The energy and nutritional demand of the parasitic life of the mite Varroa destructor," Apidologie, vol. 35, Issue 4, Jul.-Aug. 2004, INRA/DIB-AGIB/ EDP Sciences, pp. 419-430.
Genersch, Elke et al., "Emerging and re-emerging viruses of the honey bee (Apis mellifera L.)," Veterinary Research, vol. 41, Issue 6, 2010, EDP Sciences, pp. 1-20.
Genersch, Elke, "Honey bee pathology: current threats to honey bees and beekeeping," Applied Microbiology and Biotechnology, vol. 87, Issue 1, Apr. 17, 2010, Springer-Verlag, pp. 87-97.
Gillespie, Jeremy P. et al., "Biological Mediators of Insect Immunity," Annual Review of Entomology, vol. 42, Issue 1, 1997, Annual Reviews, pp. 611-643.
Genersch, Elke et al., "The German bee monitoring project: a long term study to understand periodically high winter losses of honey bee colonies," Apidologie, vol. 41, Issue 3, May-Jun. 2010, INRA/DIB-AGIB/EDP Sciences, pp. 1-21.
Ginzel, Matthew D. et al., "(Z)-9-Nonacosene-Major Component of the Contact Sex Pheromone of the Beetle Megacyllene caryae," Journal of Chemical Ecology, vol. 32, Issue 2, Feb. 2006, Springer Science + Business Media, Inc., pp. 435-451.
Goode, Katarzyna et al., "Hygienic behavior of the honey bee (Apis mellifera) is independent of sucrose responsiveness and foraging ontogeny," Hormones and Behavior, vol. 49, Issue 3, Mar. 2006, Elsevier Inc., pp. 391-397.
Goulson, Dave et al., "Bee declines driven by combined stress from parasites, pesticides, and lack of flowers," Science, vol. 347, Issue 6229, Mar. 27, 2015, American Association for the Advancement of Science (AAAS), 11 pages.
Goulson, Dave et al., "Combined stress from parasites, pesticides and lack of flowers drives bee declines," Science, vol. 347, Issue 6229, Feb. 2015, American Association for the Advancement of Science, pp. 1-30.
Granberg, Fredrik et al., "Metagenomic Detection of Viral Pathogens in Spanish Honeybees: Co-Infection by Aphid Lethal Paralysis, Israel Acute Paralysis and Lake Sinai Viruses," PLOS ONE, vol. 8, Issue 2, Feb. 2013, www.plosone.org, pp. 1-8.
Gregorc, Aleš et al., "Gene expression in honey bee (Apis mellifera) larvae exposed to pesticides and Varroa mites (Varroa destructor)," Journal of Insect Physiology, vol. 58, Issue 8, 2012, Elsevier Ltd., pp. 1042-1049.
Gregory, Pamela G. et al., "Conditional immune-gene suppression of honeybees parasitized by Varroa mites," Journal of Insect Science, vol. 5, Issue 7, Mar. 25, 2005, Oxford University Press, insectscience.org/5.7, pp. 1-5.
Haarmann, Timothy et al., "Effects of Fluvalinate and Coumaphos on Queen Honey Bees (Hymenoptera: Apidae) in Two Commercial Queen Rearing Operations," Journal of Economic Entomology, vol. 95, Issue 1, Feb. 2002, Entomological Society of America, pp. 28-35.
Harbo, John R. et al., "Resistance to Varroa destructor (Mesostigmata: Varroidae) When Mite-Resistant Queen Honey Bees (Hymenoptera: Apidae) Were Free-Mated with Unselected Drones," Journal of Economic Entomology, vol. 94, Issue 6, Dec. 2001, Entomological Society of America, pp. 1319-1323.
Harbo, John R. et al., "Responses to Varroa by honey bees with different levels of Varroa Sensitive Hygiene," Journal of Apicultural Research and Bee World, vol. 48, Issue 3, 2009, IBRA, pp. 156-161.
Harbo, John R. et al., "Suppressed mite reproduction explained by the behaviour of adult bees," Journal of Apicultural Research, vol. 44, Issue 1, 2005, IBRA, pp. 21-23.
Harris, Jeffrey W., "Bees with Varroa Sensitive Hygiene preferentially remove mite infested pupae aged ≤ five days post capping," Journal of Apicultural Research, vol. 46, Issue 3, 2007, IBRA, pp. 134-139.
Harris, Jeffrey W. et al., "Changes in Infestation, Cell Cap Condition, and Reproductive Status of Varroa destructor (Mesostigmata: Varroidae) in Brood Exposed to Honey Bees with Varroa Sensitive Hygiene," Annals of the Entomological Society of America, vol. 105, Issue 3, May 2012, Entomological Society of America, pp. 512-518.
Harris, Jeffrey W., "Effect of Brood Type on Varroa-Sensitive Hygiene by Worker Honey Bees (Hymenoptera: Apidae)," Annals of the Entomological Society of America, vol. 101, Issue 6, 2008, pp. 1137-1144.
Harris, Jeffery et al., "Selecting for Varroa Sensitive Hygiene," Bee Health, Nov. 12, 2010, http://articles.extension.org/pages/30984/selecting-for-varroa-sensitive-hygiene, eXtension, 4 pages.
Harris, Jeffrey et al., "Varroa Sensitive Hygiene and Mite Reproduction," Bee Health, Dec. 13, 2013, http://articles.extension.org/pages/30361/varroa-sensitive-hygiene-and-mite-reproduction, 5 pages.
Hawthorne, David J. et al., "Killing Them with Kindness? In-Hive Medications may Inhibit Xenobiotic Efflux Transporters and Endanger Honey Bees," PLoS ONE, vol. 6, Issue 11, Nov. 2, 2011, www.plosone.org, pp. 1-6.
Herrmann, Matthias et al., "Survival of honey bee (Apis mellifera) pupae after trypan blue staining of wounds caused by Varroa destructor mites or artificial perforation," Apidologie, vol. 36, Issue 1, Mar. 16, 2005, INRA/DIB-AGIB/ EDP Sciences, pp. 107-111.
Higes, Mariano et al., "How natural infection by Nosema ceranae causes honeybee colony collapse," Environmental Microbiology, vol. 10, Issue 10, 2008, Society for Applied Microbiology and Blackwell Publishing Ltd., pp. 2659-2669.
USPTO, Non-Final Rejection in U.S. Appl. No. 15/742,072 dated May 17, 2019.
Sonnet, P.E., et al., Sex Pheromone of the Stable Fly, Identification, Synthesis, and Evaluation of Alkenes from Female Stable Flies, Journal of Chemical Ecology, 1979, pp. 353-361, vol. 5, No. 3.
Aboshi, Takako et al., "Biosynthesis of linoleic acid in Tyrophagus mites (Acarina: Acaridae)," Insect Biochemistry and Molecular Biology, vol. 43, Issue 11, 2013, Elsevier Ltd., pp. 991-996.
Aizen, Marcelo A. et al., "The Global Stock of Domesticated Honey Bees is Growing Slower Than Agricultural Demand for Pollination," Current Biology, vol. 19, Issue 11, Jun. 9, 2009, Elsevier Ltd., pp. 915-918.
Alaux, Cëdric et al., "Nutrigenomics in honey bees: digital gene expression analysis of pollen's nutritive effects on healthy and varroa-parasitized bees," BMC Genomics, vol. 12, Issue 496, Oct. 10, 2011, BioMed Central, http://www.biomedcentral.com/1471-2164/12/496, pp. 1-13.
Amdam, Gro V. et al., "Altered Physiology in Worker Honey Bees (Hymenoptera: Apidae) Infested with the Mite Varroa destructor (Acari: Varroidae): A Factor in Colony Loss During Overwintering?" Journal of Economic Entomology, vol. 97, Issue 3, Jun. 2004, Entomological Society of America, pp. 741-747.
Anders, Simon et al., HTSeq—a Python framework to work with high-throughput sequencing data, Bioinformatics, vol. 31, Issue 2, 2015, Oxford University Press, pp. 166-169.
Anderson, Claus Lindbjerg et al., "Normalization of Real-Time Quantitative Reverse Transcription-PCR Data: A Model-Based Variance Estimation Approach to Identify Genes Suited for Normalization, Applied to Bladder and Colon Cancer Data Sets," Cancer Research, vol. 64, Issue 15, Aug. 1, 2004, American Association for Cancer Research, pp. 5245-5250.

(56) References Cited

OTHER PUBLICATIONS

Anderson, D.L. et al., "*Varroa jacobsoni* (Acari: Varroidae) is more than one species," Experimental and Applied Acarology, vol. 24, Issue 3, Jan. 6, 2000, Kluwer Academic Publishers, pp. 165-189.
Arrese, Estela L. et al., "Insect Fat Body: Energy, Metabolism, and Regulation," Annual Review of Entomology, vol. 55, 2010, Annual Reviews, pp. 207-225.
Author Unknown, "Bee Healthy Roadmap: Improving Honey Bee Health," Honey Bee Health Coalition, Oct. 2014, http://honeybeehealthcoalition.org/wp-contentuploads/2014/12Bee-Healthy-Roadmap-October-2014.pdf, www.honeybeehealthcoalition.org, 6 pages.
Aumeier, Pia et al., "Scent or movement of Varroa destructor mites does not elicit hygienic behaviour by Africanized and Carniolan honey bees," Apidologie, vol. 32, Issue 3, May-Jun. 2001, INRA/DIB-AGIB/EDP Sciences, pp. 253-263.
Azzami, Klara et al., "Infection of honey bees with acute bee paralysis virus does not trigger humoral or cellular Immune responses," Archives of Virology, vol. 157, Issue 4, Jan. 19, 2012, Springer, pp. 689-702.
Baracchi, David et al., "Evidence for antiseptic behaviour towards sick adult bees in honey bee colonies," Journal of Insect Physiology, vol. 58, Issue 12, Dec. 2012, Elsevier Ltd., pp. 1589-1596.
Behrens, Dieter et al., "Three QTL in the honey bee *Apis mellifera* L. suppress reproduction of the parasitic mite *Varroa destructor*," Ecology and Evolution, vol. 1, Issue 4, Dec. 2011, Blackwell Publishing Ltd., pp. 451-458.
Bello, Jan E. et al., "Isolation and determination of absolute configurations of insect-produced methyl-branched hydrocarbons," Proceedings of the National Academy of Sciences, vol. 112, Issue 4, Jan. 27, 2015, PNAS, pp. 1077-1082.
Benoit, Joshua B. et al., "Mycoflora and fungal vector capacity of the parasitic mite *Varroa destructor* (Mesostigmata: Varroidae) in honey bee (Hymenoptera: Apidae) colonies," International Journal of Acarology, vol. 30, Issue 2, 2004, Taylor & Francis, pp. 103-106.
Berry, Jennifer, "Pesticides, Bees and Wax: An unhealthy, untidy mix," Bee Culture, Jan. 2009, vol. 137, Bee Culture, pp. 33-35.
Biesmeijer, J. C. et al., "Parallel Declines in Pollinators and Insect-Pollinated Plants in Britain and the Netherlands," Science, vol. 313, Issue 5785, Jul. 21, 2006, American Association for the Advancement of Science (AAAS), pp. 351-354.
Bogdanov, Stefan, "Contaminants of bee products," Apidologie, vol. 37, Issue 1, Jan.-Feb. 2006, INRA/DIB-AGIB/ EDP Sciences, pp. 1-18.
Boecking, Otto et al., "Behavioral defenses of honey bees against *Varroa jacobsoni* Oud.," Apidologie, vol. 30, Issue 2-3, 1999, Elsevier, pp. 141-158.
Boekling, Otto et al., "Heritability of the Varroa-speci® c hygienic behaviour in honey bees (Hymenoptera: Apidae)," Journal of Animal Breeding and Genetics, vol. 117, Issue 6, Dec. 2000, Blackwell Wissenschafts-Verlag, Berlin, pp. 417-424.
Boecking, Otto et al., "The pore in the hard conical Apis cerana drone capping results from a spinning process," Apidologie, vol. 30, Issue 6, 1999, INRA / EDP Sciences / DIB-AGIB, pp. 513-519.
Boecking, O. et al., "The removal response of *Apis mellifera* L. colonies to brood in wax and plastic cells after artificial and natural infestation with *Varroa jacobsoni* Oud. and to freeze-killed brood," Experimental & Applied Acarology, vol. 16, Issue 4, Dec. 1992, Elsevier Science Publishers B.V., pp. 321-329.
Boecking, O. et al., "Varroosis—the Ongoing Crisis in Bee Keeping," Journal für Verbraucherschutz und Lebensmittelsicherheit, vol. 3, Issue 2, May 2008, SP Birkhäuser Verlag Basel, pp. 221-228.
Boncristiani, Humberto, et al., "Direct effect of acaricides on pathogen loads and gene expression levels in honey bees *Apis mellifera*," Journal of Insect Physiology, vol. 58, Issue 5, May 2012, Elsevier Ltd., pp. 1-8.
Boncristiani, Humberto F. et al., "In Vitro Infection of Pupae with Israeli Acute Paralysis Virus Suggests Disturbance of Transcriptional Homeostasis in Honey Bees (*Apis mellifera*)," PLOS ONE, vol. 8, Issue 9, Sep. 2013, www.plosone.org, pp. 1-11.
Böröczky, Katalin et al., "Insects groom their antennae to enhance olfactory acuity," Proceedings of the National Academy of Sciences (PNAS), vol. 110, Issue 9, Feb. 26, 2013, www.pnas.org/cgi/doi/10.1073/pnas.1212466110, National Academy of Sciences, pp. 3615-3620.
Bourgeois, A. Lelania et al., "Genetic Characterization of Russian Honey Bee Stock Selected for Improved Resistance to Varroa destructor," Journal of Economic Entomology, vol. 102, Issue 3, Jun. 2009, pp. 1233-1238.
Bowen-Walker, P.L. et al., "The Transmission of Deformed Wing Virus between Honeybees (*Apis mellifera* L.) by the Ectoparasitic Mite *Varroa jacobsoni oud*," Journal of Invertebrate Pathology, vol. 73, Issue 1, Jan. 1999, Academic Press, pp. 101-106.
Burley, Lisa M. et al., "Survival of Honey Bee (Hymenoptera: Apidae) Spermatozoa Incubated at Room Temperature from Drones Exposed to Miticides," Journal of Economic Entomology, vol. 101, Issue 4, Aug. 1, 2008, Entomological Society of America, pp. 1081-1087.
Calderón, Rafael A. et al., "Behavior of varroa mites in worker brood cells of Africanized honey bees," Experimental and Applied Acarology, vol. 49, Issue 4, Dec. 2009, Springer Science+Business Media B.V., pp. 329-338.
Calderone, Nicholas W., "Evaluation of Formic Acid and a Thymol-Based Blend of Natural Products for the Fall control of Varroa jacobsoni (Acari: Varroidae) in Colonies of Apis mellifera (Hymenoptera: Apidae)," Journal of Economic Entomology, vol. 92, Issue 2, Apr. 1, 1999, Entomological Society of America, pp. 253-260.
Calderone, Nicholas W., "Insect Pollinated Crops, Insect Pollinators and US Agriculture: Trend Analysis of Aggregate Data for the Period 1992-2009," PLoS ONE, vol. 7, Issue 5, May 22, 2012, www.plosone.org, pp. 1-27.
Carlson, D.A. et al., "Polyunsaturated Hydrocarbons in the Stable Fly," Journal of Chemical Ecology, vol. 11, Issue 11, Nov. 1985, Springer, pp. 1485-1496.
Carreck, Norman L. et al., "Honey bee colony collapse and changes in viral prevalence associated with Varroa destructor," Journal of Apicultural Research, vol. 49, Issue 1, 2010, IBRA, pp. 93-94.
Carreck, Norman, "Varroa—still a problem in the 21st century?" Jan. 2011, International Bee Research Association, 2 pages.
Caulkins, Peter, "Environmental Protection Agency: Tau-fluvalinate; Reregistration Eligibility Decision for Low Risk Pesticide; Notice of Availability," Agency No. OPP-2005-0230, Nov. 7, 2005, in Federal Register: A Notice by the Environmental Protection Agency, vol. 70, Issue 220, Nov. 16, 2005, Office of the Federal Register, pp. 69555-69557.
Charlier, Cathy et al., "Oocyte-somatic cells interactions, lessons from evolution," BMC Genomics, vol. 13, Oct. 2012, BioMed Central Ltd., pp. 1-18.
Chen, Yan Ping et al., "Chapter 2: Honey Bee Viruses," Advances in Virus Research (book), vol. 70, 2007, New York, New York, Academic Press, pp. 33-80.
Chen, Yanping et al., "Multiple virus infections in the honey bee and genome divergence of honey bee viruses," Journal of Invertebrate Pathology, vol. 87, Issue 2-3, Oct.-Nov. 2004, Elsevier Inc., pp. 84-93.
Chen, Yanping et al., "Transmission of Kashmir bee virus by the ectoparasitic mite *Varroa destructor*," Apidologie, vol. 35, Issue 4, Jul.-Aug. 2004, Springer Verlag, pp. 441-448.
Claudianos, C. et al., "A deficit of detoxification enzymes: pesticide sensitivity and environmental response in the honeybee," Insect Molecular Biology, vol. 15, Issue 5, Oct. 2006, The Royal Entomological Society, pp. 615-636.
Coelho, Joseph R., "Heat Transfer and Body Temperature in Honey Bee (Hymenoptera: Apidae) Drones and Workers," Environmental Entomology, vol. 20, Issue 6, Dec. 1991, Entomological Society of America, pp. 1627-1635.
Collins, Anita, M. et al., "Performance of honey bee (*Apis mellifera*) queens reared in beeswax cells impregnated with coumaphos," Journal of Apicultural Research, vol. 43, Issue 3, Jul. 1, 2004, IBRA, pp. 128-134.
Cornman, Robert Scott et al., "Pathogen Webs in Collapsing Honey Bee Colonies," PloS One, vol. 7, Issue 8, Aug. 2012, www.plosone.org, pp. 1-15.

(56) References Cited

OTHER PUBLICATIONS

Cornman, Robert Scott et al., "Population-genomic variation within RNA viruses of the Western honey bee, *Apis mellifera*, inferred from deep sequencing," BMC Genomics, vol. 14, Issue 154, 2013, BioMed Central, http://www.biomedcentral.com/1471-2164/14/154, pp. 1-14.

Cox-Foster, Diana L. et al., "A Metagenomic Survey of Microbes in Honey Bee Colony Collapse Disorder," Science, vol. 318, Issue 283, Oct. 12, 2007, American Association for the Advancement of Science (AAAS), pp. 283-287.

Dahlgren, Lizette et al., "Comparative Toxicity of Acaricides to Honey Bee (Hymenoptera: Apidae) Workers and Queens," Journal of Economic Entomology, vol. 105, Issue 6, 2012, Entomological Society of America, pp. 1895-1902.

Dainat, Benjamin et al., "Predictive Markers of Honey Bee Colony Collapse," PLoS ONE, vol. 7, Issue 2, Feb. 23, 2012, www.plosone.org, pp. 1-9.

De Guzman, Lilia I. et al., "Hygienic Behavior by Honey Bees From Far-eastern Russia," American Bee Journal, vol. 142, Issue 1, Jan. 2002, pp. 58-60.

Aizen, M.A., et al., Long-Term Global Trends in Crop Yield and Production Reveal no Current Pollination Shortage But Increasing Pollinator Dependency, Current Biology, Oct. 28, 2008, pp. 1572-1575, vol. 18.

Annoscia, D., et al., How does the mite *Varroa destructor* kill the honeybee *Apis mellifera*? Alteration of cuticular hydrcarbons and water loss in infested honeybees, Journal of Insect Physiology, 2012, pp. 1548-1555, vol. 58.

Aumeier, P., et al., Cuticular volatiles, attractivity of worker larvae and invasion of brood cells by Varroa mites. A comparison of Africanized and European honey bees, Chemoecology, 2002, pp. 65-75, vol. 12.

Bloomquist, G.J., et al., Introduction: history and overview of insect hydrocarbons, Cambridge University Press, 2010, p. 3.

Dani, F.R., et al, Deciphering the recognition signature within the cuticular chemical profile of paper wasps Animal Behaviour, 2001, pp. 165-171, vol. 62.

Danka, R.G., et al., Varying congruence of hygienic responses to Varroa destructor and freeze-killed brood among different types of honeybees, Apidologie, 2013, pp. 447-457, vol. 44.

De Miranda, J.R., et al, Deformed Wing Virus, Journal of Invertebrate Pathology, 2010, pp. S48-S61, vol. 103.

Del Piccolo, F., et al., Selection of Apis mellifera workers by the parasitic mite *Varroa destructor* using host cuticular hydrocarbons, Parasitology, 2010, pp. 967-973, vol. 137.

Francis, B.R., et al., Extractable surface hydrocarbons of workers and drones of the genus *Apis*, Journal of Apicultural Research, 1985, pp. 13-26, vol. 24, Issue 1.

Gilliam, M., et al, Hygienic behavior of honey bees in relation to chalkbrood disease, Apidologie, 1983, pp. 29-39, vol. 14, Issue 1.

Gisder, S., et al., Deformed wing virus: replication and viral load in mites (*Varroa destructor*), Journal of General Virology, 2009, pp. 463-467, vol. 90.

Gramacho, K.P., et al., Differences in olfactory sensitivity and behavioral responses among honey bees bred for hygienic behavior, Behavioral Ecology and Sociobiology, 2003, pp. 472-479, vol. 54.

Haarmann, T., et al., Effects of fluvalinate and coumaphos on queen honey bees (Hymenoptera: Apidae) in two commercial queen rearing operations, Journal of Economic Entomology, 2002, pp. 28-35, vol. 95.

Hefetz, A., The evolution of hydrocarbon pheromone parsimony in ants (Hymenoptera: Formicidae)—interplay of colony odor uniformity and odor idiosyncrasy, Myrmecological News, Sep. 2007, pp. 59-68, vol. 10.

Highfield, A.C., et al., Deformed wing virus implicated in overwintering honeybee colony losses, Applied and Environmental Microbiology, 2009, pp. 7212-7220, vol. 75, No. 22.

Howard, R.W., et al., Ecological, behavioral, and biochemical aspects of insect hydrocarbons, Annu Rev Entomol, 2005, pp. 371-393, vol. 50.

Ibrahim, A., et al., Field trial of honey bee colonies bred for mechanisms of resistance against Varroa destructor, Apidologie, 2007, pp. 67-76, vol. 38.

Larsson, K., et al., Antimicrobial effect of simple lipids with different branches at the methyl end group, Antimicrobial Agents and Chemotherapy, 1975, pp. 742-750, vol. 8.

Le Conte, Y., et al., Varroa destructor changes its cuticular hydrocarbons to mimic new hosts, Biology Letters, 2015, pp. 1-4, vol. 11:20150233.

Martin, C., et al., Variations in chemical mimicry by the ectoparasitic mite *Varroa jacobsoni* according to the developmental stage of the host honey-bee *Apis mellifera*, Insect Biochemistry and Molecular Biology, 2001, pp. 365-379, vol. 31.

Mockel, N., et al., Horizontal transmission of deformed wing virus: pathological consequences in adult bees (*Apis mellifera*) depend on the transmission route, Journal of General Virology, 2011, pp. 370-377, vol. 92.

Mondet F., et al., Antennae hold a key to Varroa-sensitive hygiene behaviour in honey bees, Scientific Reports 5, 2015, pp. 1-12.

Nascimento, D.L., et al. Acceptance threshold hypothesis is supported by chemical similarity of cuticular hydrocarbons in a stingless bee, *Melipona asilvai*, Journal of Chemical Ecology, 2012, pp. 1432-1440, vol. 38.

Nation, J.L., et al., Cuticular hydrocarbons from Varroa jacobsoni, Experimental & Applied Acarology, 1992, pp. 331-344, vol. 16.

Nazzi, F., et al., (Z)-8-Heptadecene from infested cells reduces the reproduction of Varroa destructor under laboratory conditions, Journal of Chemical Ecology, 2002, pp. 2181-2190, vol. 28.

Pettis, J.S., et al., Fluvalinate treatment of queen and worker honey bees (*Apis mellifera* L) and effects on subsequent mortality, queen acceptance and supersedure, Apidologie, 1991, pp. 1-7, vol. 22.

Soroker, V., et al., Hydrocarbon site of synthesis and circulation in the desert ant *Cataglyphis niger*, Journal of Insect Physiology, 2000, pp. 1097-1102, vol. 46.

Villa, J.D., et al., Simplified methods of evaluating colonies for levels of Varroa Sensitive Hygiene (VSH), Journal of Apicultural Research, 2009, pp. 162-167, vol. 48.

Yang, X., et al., Effects of parasitization by Varroa destructor on survivorship and physiological traits of Apis mellifera in correlation with viral incidence and microbial challenge, 2007, Parasitology, pp. 405-412, vol. 134.

Francis, B.R., et al., Hydrocarbons of the cuticle and hemolymph of the adult honey bee (Hymenoptera: Apidae), Annals of the Entomological Society of America, 1989, pp. 486-494, vol. 82, No. 4.

Oliveira, C.C., et al., Variations on a theme: diversification of cuticular hydrocarbons in a clade of cactophilic *Drosophila*, BMC Evolutionary Biology, 2011, pp. 1-19, vol. 11, No. 179.

Huang, Alice S. et al., "Defective Viral Particles and Viral Disease Processes," Nature, vol. 226, Apr. 25, 1970, Nature Publishing Group, pp. 325-327.

Hunter, Wayne et al., "Large-Scale Field Application of RNAi Technology Reducing Israeli Acute Paralysis Virus Disease in Honey Bees (*Apis mellifera*, Hymenoptera: Apidae)," PLoS Pathogens, vol. 6, Issue 12, Dec. 23, 2010, https://doi.org/10.1371/journal.ppat.1001160, pp. 1-10.

Hurd, Hilary, "Manipulation of Medically Important Insect Vectors by Their Parasites," Annual Review of Entomology, vol. 48, 2003, Annual Reviews, pp. 141-161.

Ibrahim, Abdullah et al., "Field trial of honey bee colonies bred for mechanisms of resistance against Varroa destructor," Apidologie, vol. 38, Issue 1, Jan.-Feb. 2007, INRA/DIB-AGIB/ EDP Sciences, pp. 67-76.

Ibrahim, Abdullah et al., "The relationship between hygienic behavior and suppression of mite reproduction as honey bee (*Apis mellifera*) mechanisms of resistance to Varroa destructor," Apidologie, vol. 37, Issue 1, Jan.-Feb. 2006, INRA/DIB-AGIB/ EDP Sciences, pp. 31-40.

Ifantidis, Michael, D., "Ontogenesis of the Mite *Varroa jacobsoni* in Worker and Drone Honeybee Brood Cells," Journal of Apicultural Research, vol. 22, Issue 3, 1983, IBRA, pp. 200-206.

(56) References Cited

OTHER PUBLICATIONS

Ifantidis, Michael, D., Some Aspects of the Process of Varroa Jacobsoni Mite Entrance Into Honey Bee (*Apis Mellifera*) Brood Cells, Apidologie, vol. 19, Issue 4, 1988, Springer International Publishing AG, pp. 387-396.

Imdorf, Anton et al., "Alternative strategy in central Europe for the control of Varroa destructor in honey bee colonies," Apiacta, vol. 38, 2003, International Federation of Beekeepers' Associations "Apimondia," pp. 258-285.

Johnson, Reed M. et al., "Changes in transcript abundance relating to colony collapse disorder in honey bees (*Apis mellifera*)," Proceedings of the National Academy of Sciences (PNAS), vol. 106, Issue 35, Sep. 1, 2009, National Academy of Sciences, pp. 14790-14795.

Johnson, Reed M., "Honey Bee Toxicology," Annual Review of Entomology, vol. 60, Oct. 10, 2014, Annual Reviews, pp. 22.1-22.20.

Johnson, Reed M. et al., "Pesticides and honey bee toxicity—USA," Apidologie, vol. 41, Issue 3, May-Jun. 2010, INRA/DIB-AGIB/EDP Sciences, pp. 1-20.

Johnson, Reed M. et al., "Synergistic Interactions Between In-Hive Miticides in Apis mellifera," Journal of Economic Entomology, vol. 102, Issue 2, Apr. 2009, Entomological Society of America, pp. 474-479.

Kanbar, G. et al., "Ultrastructure and bacterial infection of wounds in honey bee (*Apis mellifera*) pupae punctured by Varroa mites," Parasitology Research, vol. 90, Issue 5, Aug. 2003, Springer International Publishing AG, pp. 349-354.

Kanga, Lambert et al., "Susceptibility of the small hive beetle, *Aethina tumida* (Coleoptera: Nitidulidae), to insecticides and insect growth regulators," Apidologie, vol. 43, Issue 1, 2012, INRA, DIB and Springer-Verlag, pp. 95-102.

Katzav-Gozansky et al., "Plasticity of Caste-Specific Dufour's Gland Secretion in the Honey Bee (*Apis mellifera* L.)," Naturwissenschaften, vol. 84, 1997, Springer-Verlag, pp. 238-241.

Kimura, Taichi et al., "Synthesis of All the Stereoisomers of 13,17-Dimethyl-1-tritriacontene and 13, 17-Dimethyl-1-pentatriacontene, the Contact Sex Pheromone Components of the Female Tsetse Fly, *Glossina austeni*,"European Journal of Organic Chemistry, Pheromone synthesis, Part 211, 2001, Wiley-VCH Verlag-GmbH, pp. 3385-3390.

Kirrane, Maria J. et al., "Asynchronous Development of Honey Bee Host and Varroa destructor (Mesostigmata: Varroidae) Influences Reproductive Potential of Mites," Journal of Economic Entomology, vol. 104, Issue 4, Aug. 2011, Entomological Society of America, pp. 1146-1152.

Kochansky, Jan et al., "Screening alternative antibiotics against oxytetracycline-susceptible and -resistant Paenibacillus larvae," Apidologie, vol. 32, Issue 3, 2001, INRA/DIB-AGIB/EDP Sciences, pp. 215-222.

Kraus, Bernhard et al., "Effect of Varroa jacobsoni (Mesostigmata: Varroidae) on Feral Apis mellifera (Hymenoptera: Apidae) in California," Environmental Entomology, vol. 24, Issue 6, Dec. 1995, Entomological Society of America, pp. 1473-1480.

Kuster, Ryan D. et al., "Immunogene and viral transcript dynamics during parasitic Varroa destructor mite infection of developing honey bee (*Apis mellifera*) pupae," The Journal of Experimental Biology, vol. 217, Issue 10, 2014, The Company of Biologists Ltd., pp. 1710-1718.

Langmead, Ben et al., "Fast gapped-read alignment with Bowtie 2," Nature Methods, vol. 9, Issue 4, 2012, Nature America, Inc., pp. 1-8.

Le Conte, Yves et al., "Honey bee colonies that have survived Varroa destructor," Apidologie, vol. 38, Issue 6, Nov.-Dec. 2007, INRA, EDP Sciences, pp. 566-572.

Le Conte, Yves et al., "Identification of a Brood Pheromone in Honeybees," Naturwissenschaften, vol. 77, Issue 1, 1990, Springer-Verlag, pp. 334-336.

Le Conte, Yves et al., "Primer Pheromones in Social Hymenoptera," Annual Review of Entomology, vol. 53, 2008, Annual Reviews, pp. 523-542.

Le Conte, Yves et al., "Varroa mites and honey bee health: can Varroa explain part of the colony losses?," Apidologie, vol. 41, Issue 3, Jan. 1, 2010, Springer Verlag, pp. 353-363.

Lee, Kathleen V. et al., "A national survey of managed honey bee 2013-2014 annual colony losses in the USA," Apidologie, vol. 46, Issue 3, May 2015, Springer Paris, pp. 292-305.

Li, Dongsheng et al., "Defective Interfering Viral Particles in Acute Dengue Infections," PLoS ONE, vol. 6, Issue 4, Apr. 2011, www.plosone.org, pp. 1-12.

Locke, Barbara et al., "Characteristics of honey bee colonies (*Apis mellifera*) in Sweden surviving Varroa destructor infestation," Apidologie, vol. 42, Issue 4, Aug. 2011, INRA, DIB-AGIB and Springer Science+Business Media B.V., pp. 533-542.

Locke, Barbara et al., "Host adaptations reduce the reproductive success of Varroa destructor in two distinct European honey bee populations," Ecology and Evolution, vol. 2, Issue 6, Feb. 29, 2012, Blackwell Publishing Ltd., pp. 1144-1150.

Locke, Barbara et al., "Increased Tolerance and Resistance to Virus Infections: A Possible Factor in the Survival of Varroa destructor-Resistant Honey Bees (*Apis mellifera*)," PLOS ONE, vol. 9, Issue 6, Jun. 2014, www.plosone.org, pp. 1-7.

Mant, Jim et al., "Cuticular Hydrocarbons as Sex Pheromone of the Bee Colletes cunicularius and the Key to Its Mimicry by the Sexually Deceptive Orchid, *Ophrys exaltata*," Journal of Chemical Ecology, vol. 31, Issue 8, Aug. 2005, Springer Science + Business Media, Inc., p. 1765-1787.

Maori, E et al., "IAPV, a bee-affecting virus associated with Colony Collapse Disorder can be silenced by dsRNA ingestion," Insect Molecular Biology, vol. 18, Issue 1, 2009, The Royal Entomological Society, pp. 55-60.

Martel, Anne-Claire et al., "Acaricide residues in honey and wax after treatment of honey bee colonies with Apivar® or Asuntol® 50," Apidologie, vol. 38, Issue 6, Nov. 2007, INRA, EDP Sciences, pp. 534-544.

Martin, Stephen, "A population model for the ectoparasitic mite *Varroa jacobsoni* in honey bee (*Apis mellifera*) colonies," Ecological Modelling, vol. 109, Issue 3, 1998, Elsevier Science B.V., pp. 267-281.

Martin, Stephen J., "Global honey bee viral landscape altered by a parasitic mite," Science, vol. 336, Jun. 8, 2012, American Association for the Advancement of Science, pp. 1304-1306.

Martin, Stephen J., "Ontogenesis of the mite *Varroa jacobsoni* Oud. in worker brood of the honeybee *Apis mellifera* L. under natural conditions," Experimental & Applied Acarology, vol. 18, Issue 2, 1994, Science and Technology Letters, pp. 87-100.

Martin, Stephen J., "The role of Varroa and viral pathogens in the collapse of honeybee colonies: a modelling approach," Journal of AppliedEcology, vol. 38, Issue 5, 2001, British Ecological Society, pp. 1082-1093.

Masterman, R. et al., "Olfactory and behavioral response thresholds to odors of diseased brood differ between hygienic and non-hygienic honey bees (*Apis mellifera* L.)," Journal of Comparative Physiology A, vol. 187, Issue 6, Jul. 11, 2001, Springer-Verlag, pp. 441-452.

McMenamin, Alexander et al., "Honey bee (*Apis mellifera*) colony losses and associated viruses," Current Opinion in Insect Science, vol. 8, 2015, Elsevier Ltd., pp. 1-9.

Millar, Jocelyn G., "Chapter 8: Chemical synthesis of insect cuticular hydrocarbons," Insect Hydrocarbons: Biology, Biochemistry, and Chemical Ecology (book), Part I—Chemistry, Biochemistry, and Physiology, 2010, Cambridge University Press, pp. 163-186.

Mondet, Fanny et al., "On the Front Line: Quantitative Virus Dynamics in Honeybee (*Apis mellifera* L.) Colonies along a New Expansion Front of the Parasite *Varroa destructor*," PLOS Pathogens, vol. 10, Issue 8, Aug. 2014, www.plospathogens.org, pp. 1-15.

Mondet, Fanny et al., "Specific Cues Associated With Honey Bee Social Defence against Varroa destructor Infested Brood," Scientific Reports, vol. 6, May 3, 2016, www.nature.com/scientificreports, pp. 1-9.

Morse, Roger A. et al., "The Value of Honey Bees As Pollinators of U.S. Crops in 2000," Bee Culture Magazine, vol. 128, Issue 3, 2000, pp. 1-15.

(56) References Cited

OTHER PUBLICATIONS

Mortazavi, Ali et al., "Mapping and quantifying mammalian transcriptomes by RNA-Seq," Nature Methods, vol. 6, Issue 7, Jul. 2008, Nature Publishing Group, pp. 621-628.
Mullin, Christopher A. et al., "High Levels of Miticides and Agrochemicals in North American Apiaries: Implications for Honey Bee Health," PLoS ONE, vol. 5, Issue 3, Mar. 19, 2010, www.plosone.org, pp. 1-19.
National Research Council, "Status of Pollinators in North America," Board on Life Sciences Board on Agriculture and Natural Resources Division on Earth and Life Studies, 2007, Washington, DC, National Academy of Sciences, 327 pages.
Nault, Brian A. et al., "Limitations of Using Regression and Mean Separation Analyses for Describing the Response of Crop Yield to Defoliation: A Case Study of the Colorado Potato Beetle (Coleoptera: Chrysomelidae) on Potato," Journal of Economic Entomology, vol. 91, Issue 1, Feb. 1, 1998, Entomological Society of America, pp. 7-20.
Nazzi, Francesco et al., "A semiochemical from brood cells infested by Varroa destructor triggers hygienic behaviour in Apis mellifera," Apidologie, vol. 35, Issue 1, 2004, Springer Verlag, pp. 65-70.
Nazzi, Francesco et al., "Synergistic Parasite-Pathogen Interactions Mediated by Host Immunity Can Drive the Collapse of Honeybee Colonies," PLoS Pathogens, vol. 8, Issue 6, Jun. 2012, www.plospathogens.org, pp. 1-16.
Neumann, Peter et al., "Varroa invasion and virus adaptation," Trends in Parasitology, vol. 28, Issue 9, Sep. 2012, Elsevier Ltd., pp. 353-354.
Trapnell, Cole et al., "Differential gene and transcript expression analysis of RNA-seq experiments with TopHat and Cufflinks," Nature Protocols, vol. 7, Issue 3, Mar. 1, 2012, Nature America, Inc., pp. 1-39.
Trapnell, Cole et al., "TopHat: discovering splice junctions with RNA-Seq," Bioinformatics, vol. 25, Issue 9, May 1, 2009, The Author(s), doi:10.1093/bioinformatics/btp120, pp. 1105-1111.
Trapnell, Cole et al, "Transcript assembly and abundance estimation from RNA-Seq reveals thousands of new transcripts and switching among isoforms," Nature Biotechnology, vol. 28, Issue 5, May 2010, Nature Publishing Group, pp. 1-20.
Tsigouri, Angeliki et al., "Study of tau-fluvalinate persistence in honey," Pest Management Science, vol. 57, 2001, Society of Chemical Industry, pp. 467-471.
Tsuruda, Jennifer M. et al., "High-Resolution Linkage Analyses to Identify Genes That Influence Varroa Sensitive Hygiene Behavior in Honey Bees," PLOS ONE, vol. 7, Issue 11, Nov. 2, 2012, www.plosone.org, pp. 1-8.
University of Maryland, "U.S. beekeepers lost 40 percent of bees in 2014-15," Science Daily, May 13, 2015, www.sciencedaily.com/releases/2015/05/150513093605.htm, ScienceDaily, 5 pages.
Van Dooremalen, Coby et al., "Winter Survival of Individual Honey Bees and Honey Bee Colonies Depends on Level of Varroa destructor Infestation," PLoS ONE, vol. 7, Issue 4, Apr. 27, 2012, www.plosone.org, pp. 1-8.
Vanengelsdorp, Dennis et al., "A historical review of managed honey bee populations in Europe and the United States and the factors that may affect them," Journal of Invertebrate Pathology, vol. 103, Nov. 11, 2009, Elsevier Inc., pp. S80-S95.
Vanengelsdorp, Dennis et al., "A national survey of managed honey bee 2010-11 winter colony losses in the USA: results from the Bee Informed Partnership," Journal of Apicultural Research, vol. 51, Issue 1, Apr. 2, 2015, IBRA, pp. 115-124.
Vanengelsdorp, Dennis et al., "A Survey of Honey Bee Colony Losses in the U.S., Fall 2007 to Spring 2008," PLoS ONE, vol. 3, Issue 12, Dec. 2008, www.plosone.org, pp. 1-6.
Vanengelsdorp, Dennis et al., "Colony Collapse Disorder: A Descriptive Study," PLoS ONE, vol. 4, Issue 8, Aug. 3, 2009, www.plosone.org, pp. 1-17.
Vincenti, Marco et al., "Determination of Double Bond Position in Diunsaturated Compounds by Mass Spectrometry of Dimethyl Disulfide Derivatives," Analytical Chemistry, vol. 59, Issue 5, 1987, pp. 694-699.
Wallner, Klaus, "Varroacides and their residues in bee products," Apidologie, vol. 30, Issue 2-3, 1999, INRA/DIB/AGIB/Elsevier, Paris, pp. 235-248.
Wang, Ying et al., "Nurse bee behaviour manipulates worker honeybee (*Apis mellifera* L.) reproductive development," Animal Behaviour, vol. 92, 2014, The Association for the Study of Animal Behaviour. Published by Elsevier Ltd., pp. 253-261.
Wantuch, Holly A. et al., "Removal of Drone Brood from Apis mellifera (Hymenoptera: Apidae) Colonies to Control Varroa destructor (Acari: Varroidae) and Retain Adult Drones," Journal of Economic Entomology, vol. 102, Issue 6, Dec. 2009, Entomological Society of America, pp. 2033-2040.
Ward, Kenneth et al., "Comparative Performance of Two Mite-Resistant Stocks of Honey Bees (Hymenoptera: Apidae) in Alabama Beekeeping Operations," Journal of Economic Entomology, vol. 101, Issue 3, Jun. 2008, Entomological Society of America, pp. 654-659.
Whitfield, Charles W. et al., "Thrice Out of Africa: Ancient and Recent Expansions of the Honey Bee, *Apis mellifera*," Science, vol. 314, Oct. 27, 2006, American Association for the Advancement of Science (AAAS), pp. 642-645.
Williams, Geoffrey R. et al., "Standard methods for maintaining adult Apis mellifera in cages under in vitro laboratory conditions," Journal of Apicultural Research, vol. 52, Issue 1, 2013, IBRA, pp. 1-36.
Williamson, Sally M. et al., "Exposure to multiple cholinergic pesticides impairs olfactory learning and memory in honeybees," The Journal of Experimental Biology, vol. 216, Issue 10, 2013, The Company of Biologists Ltd., pp. 1799-1807.
Wilson-Rich, Noah et al., "Genetic, Individual, and Group Facilitation of Disease Resistance in Insect Societies," Annual Review of Entomology, vol. 54, 2009, Annual Reviews, pp. 405-423.
Wu, Judy Y. et al., "Sub-Lethal Effects of Pesticide Residues in Brood Comb on Worker Honey Bee (*Apis mellifera*) Development and Longevity," PLoS ONE, vol. 6, Issue 2, Feb. 23, 2011, www.plosone.org, pp. 1-11.
Yang, Xiaolong et al., "Impact of an ectoparasite on the immunity and pathology of an invertebrate: Evidence for host immunosuppression and viral amplification," Proceedings of the National Academy of Sciences (PNAS), vol. 102, Issue 21, May 24, 2005, The National Academy of Sciences of the USA, pp. 7470-7475.
Youngsteadt, Elsa et al., "Seed odor mediates an obligate ant—plant mutualism in Amazonian rainforests," Proceedings of the National Academy of Sciences (PNAS), vol. 105, Issue 12, Mar. 25, 2008, The National Academy of Sciences of the USA, pp. 4571-4575.
International Search Report and Written Opinion for International Patent Application No. PCT/US2016/040993, dated Oct. 18, 2016, 8 pages.

\* cited by examiner

METHODS AND COMPOSITIONS FOR INDUCING HYGIENIC BEHAVIOR IN HONEY BEES

CROSS REFERENCE TO RELATED APPLICATIONS

This application is a divisional application of U.S. patent application Ser. No. 15/742,072 filed Jan. 5, 2018, which is a 35 U.S.C. § 371 national phase application of PCT Application PCT/US16/40993 filed Jul. 5, 2016, which claims priority to U.S. Provisional Patent Application No. 62/188,991 filed on Jul. 6, 2015. The contents of each are hereby incorporated by reference in their entirety.

STATEMENT REGARDING FEDERALLY SPONSORED RESEARCH OR DEVELOPMENT

This invention was made with government support under Grant No. 2010-65104-20533 awarded by the National Institute of Food and Agriculture, an agency within the United States Department of Agriculture. The government has certain rights in the invention.

FIELD

The inventions relate to the fields of agriculture, apiculture and hygienic behavior in honey bees.

SEQUENCE LISTING

The instant application contains a Sequence Listing which has been submitted electronically in ASCII text file format and is hereby incorporated by reference in its entirety. Said ASCII copy, created Aug. 9, 2019, is named "UNCG-961-4-2-Sequence_Listing-20190809.txt" and is 2 kb in size.

BACKGROUND

Honey bees are the most important commercial pollinator world-wide for agricultural production and food security. Agriculture depends on animal pollination for over 100 different crops that provide >30% of the human diet and also supply fiber, fuel, and drugs. [3, 4] Honey bees are responsible for 80% of managed insect pollination and their economic impact on U.S. food crops in the year 2000 has been estimated to be $14.6 billion. [3]However, honey bees and other insect pollinators suffer from a combination of factors, including habitat loss, pesticide exposure, pathogens, and stress due to active management. [15, 16] Recently, honey bee health has been marked with sharp declines and losses of colonies, with reports of "colony collapse disorder." [17] The failure to identify a single factor as the cause of colony collapse disorder indicates that the global honey bee health crisis is complex and heterogeneous: Multiple stressors may act synergistically to lead to symptomatic health declines and colony failure [18] and the causes may vary in time and between locations. [19]

While no single factor has been identified as the cause of colony collapse disorder, the introduction and spread of parasites and associated pathogens and pesticide exposure have a central role in the health decline of honey bees. [17, 20-29] Disease control in the honey bee is crucial because it remains the most important commercial pollinator world-wide and its pollination services are irreplaceable in many agricultural systems. Moreover, honey bees are significant pollinators in natural ecosystems and are potential vectors of diseases that threaten native pollinator communities. [6]

The ectoparasitic mite *Varroa destructor* in particular is a threat to honey bee health and apiculture today. [30, 31, 33, 41, 42] *Varroa* enter honey bee colonies to complete its reproductive cycle on developing honey bee brood. [30, 31] Mature, fertilized *Varroa* females enter a brood cell to lay eggs, and both the *Varroa* female and its offspring feed on the brood. [35] *Varroa* causes physical and physiological damage when feeding on the brood. *Varroa* is a vector of viruses and has been associated with viral amplification and honey bee disease susceptibility. Miticides used to control *Varroa* infestations are problematic because of toxicity to honey bees, beekeepers, and crops; general ecosystem pollution; and resistance development in *Varroa*.

*Varroa* is conventionally treated with synthetic acaricides, most notably coumaphos, tau-fluvalinate, flumethrin, and amitraz. [31] These substances are toxic and persistent and may accumulate in the hive [64], consequently harming honey bee health. [65, 66] For example, miticides fluvalinate and coumaphos, have been found to have lethal and sub-lethal effects on honey bee queens, workers, and drones. [2, 31, 64-66, 132, 154, 162, 177, 181] Moreover, resistance build-up in resident *Varroa* populations decreases the efficacy of chemical control. [31, 72, 178] Synergistic effects of fluvalinate and coumaphos have been measured, where the toxicity of each chemical is significantly increased in bees previously exposed to the other. [172] Furthermore, immunosuppression caused by chemical exposure makes honey bees more susceptible to parasites like *Varroa*, as well as to the pathogens they vector. [64, 70, 181, 184] In addition to affecting honey bee health, miticides compromise beekeeper health [158], enter bee products including those consumed by humans [64, 157, 174, 185] and contribute to general ecosystem pollution.

Other control strategies such as physical mite removal and use of organic acids and essential oils have been proposed as alternatives, but have many limitations that compromise efficacy, such as the labor-intensive application, temperature-sensitivity, and potential side-effects on honey bees. [74, 75, 171] Despite substantial evidence of the need, no adequate solution for control of *Varroa* has been developed. [75]

Traditional efforts to keep honey bees healthy have focused on management techniques and treatments (primarily chemotherapies). These treatments may lead to a loss of honey, are expensive and labor-intensive, and pose human health risks. [62, 63] Moreover, their long-term efficacy is questionable: None of the honey bee diseases have been eradicated due to past management. On the contrary, a steady emergence of novel pests and pathogens can be observed. [19]

Beekeepers have selectively bred honey bees for hygienic behavior as an alternative. [75, 87, 92, 155, 183] The mechanism for hygienic behavior is not completely understood, but the trait can be measured, for instance, by frequency of certain behaviors in honey bees. Minnesota Hygienic (HYG) is a breed of honey bees based on the high frequency of honey bee removal of freeze-killed brood. [83] A circle of brood is frozen with liquid nitrogen and percent removal of the killed brood is recorded, thus assessing the effectiveness of the general detection and removal of dead brood. [83] However, the olfactory trigger for hygienic removal of mite-infested and other live brood may be significantly lower than that of dead brood. [10, 100, 112, 156, 175, 183] HYG breeding relies on olfactory triggers of dead brood and results in bred honey bees that may lack sufficient sensitivity to living diseased brood. [94, 100] Another example is *Varroa* Sensitive Hygienic (VSH), which is a breed of honey bees based on measured changes in mite reproduction. [85] VSH breeding is based on a more narrowly defined goal but hygienic behavior may just be one mechanism for these bees to suppress mite reproduction. It has been unclear whether VSH bees are truly distinct or whether suppression of mite reproduction is due to the interruption of the mite reproductive cycle by hygienic removal of infested brood. [31, 84, 85, 170, 196] While the HYG and VSH hygienic honey bee colonies exhibit reduced mite and disease loads compared to unselected hives [9, 84, 167, 182], the selective breeding programs are not widely adopted by beekeepers due to lack of specificity, difficulty and expense of current selection assays. [92-95, 99, 183, 197] Also, hygienic lines do not yet serve as complete alternatives to chemical *Varroa* control [75], as chemical treatments are sometimes required to control severe mite infestations in hygienic hives. [170, 182]

Moreover, despite the presence of natural honey bee social immune mechanisms like hygienic behavior, honey bee health is currently being severely threatened. Following global pollinator population trends [2, 189], managed honey bee colonies in the United States have declined steadily for over six decades, from 5.9 million colonies in 1947 to 2.4 million colonies in 2005 [190, 191]. Total annual colony losses in the United States have exceeded 33% in four of the last five years, exceeding 45% between April 2012 and April 2013. [192, 193, 194, 195] Honey bee losses are largely attributed to introduction and spread of new parasites and associated pathogens, and to lethal and sublethal effects of agrochemical exposure. [2, 47, 195]

The long-term sustainability of apiculture depends on the balance between the benefit of honey bee keeping to the individual and the costs of honey bee management and losses. There remains a need for improving selection of honey bees for hygienic behavior and use of hygienic behavior by honey bees to prevent or treat a diseased honey bee colony to ensure adequate supplies of managed pollinators for agriculture.

SUMMARY

The presently disclosed subject matter provides tritriacontene compositions for inducing hygienic behavior in honey bees; mite-infested brood extract compositions for inducing hygienic behavior in honey bees; methods of inducing hygienic behavior in honey bees; methods of selecting one or more honey bee(s) exhibiting hygienic behavior, and methods for assessing the degree of hygienic behavior within a honey bee colony.

In some embodiments, the presently disclosed subject matter is directed to a composition for inducing hygienic behavior in honey bees comprising a tritriacontene and an agriculturally acceptable diluent or carrier, wherein the tritriacontene is in an effective amount for inducing hygienic behavior in honey bees. In a further embodiment, the tritriacontene is a stereoisomer, racemic mixture or optically active mixture. The various stereoisomers include geometric isomers/diastereomers (e.g. cis-isomers and trans-isomers, also referred to as Z-isomers and E-isomers) and enantiomers; and refers to isomers that differ only in the way the atoms are arranged in space. In one embodiment, the tritriacontene is a trans-isomer. In one embodiment, the tritriacontene is of the structure:

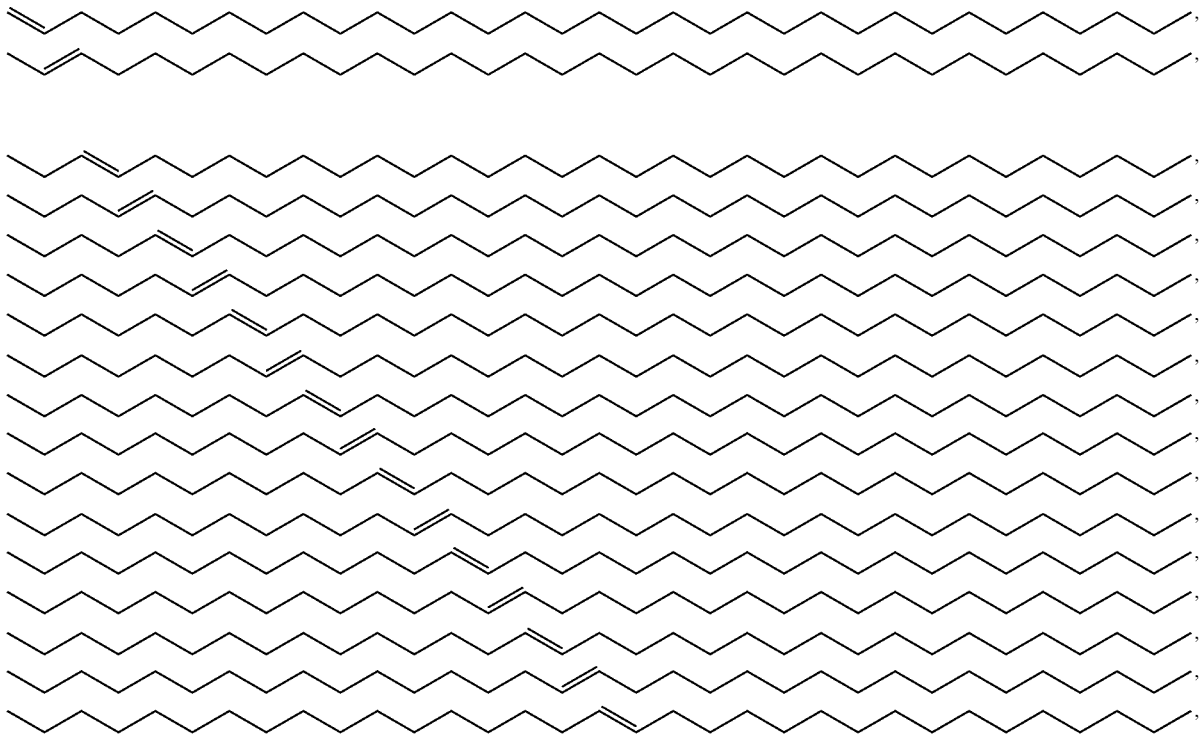

or agriculturally acceptable derivatives thereof. In one embodiment, the tritriacontene is a cis-isomer. In one embodiment, the tritriacontene is of the structure:

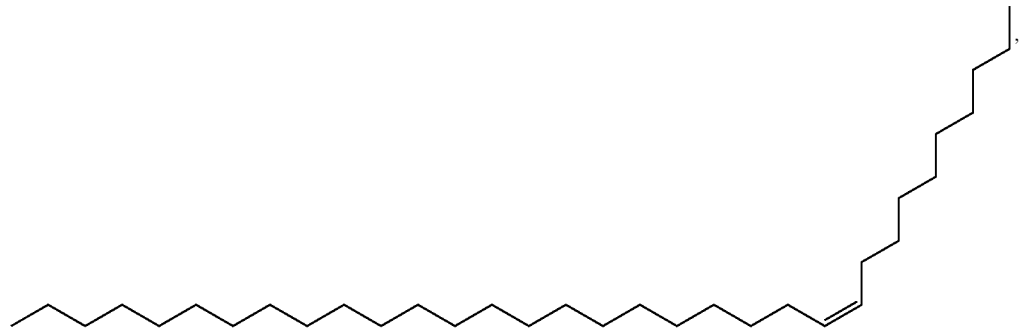 [SMILES: CCCCCCCCC/C=C\CCCCCCCCCCCCCCCCCCCCCC]

or an agriculturally acceptable derivative thereof.

In some embodiments, the presently disclosed subject matter is directed to a composition for inducing hygienic behavior in honey bees comprising mite-infested brood extract and an agriculturally acceptable diluent or carrier, wherein the mite-infested brood extract is in an effective amount for inducing hygienic behavior in honey bees. In one embodiment, the mite-infested brood extract has a concentration of 3, 1, or 0.3 brood equivalents.

In other embodiments, the presently disclosed subject matter is directed to a method of inducing hygienic behavior in honey bees, the method comprising contacting hive cells with a composition comprising a tritriacontene and an agriculturally acceptable diluent or carrier, wherein the tritriacontene is in an effective amount for inducing hygienic behavior in honey bees. In a further embodiment, the tritriacontene is a stereoisomer, racemic mixture or optically active mixture. The various stereoisomers include geometric isomers/diastereomers (e.g. cis-isomers and trans-isomers, also referred to as Z-isomers and E-isomers) and enantiomers; and refers to isomers that differ only in the way the atoms are arranged in space. In one embodiment, the tritriacontene is a trans-isomer. In one embodiment, the tritriacontene is of the structure:

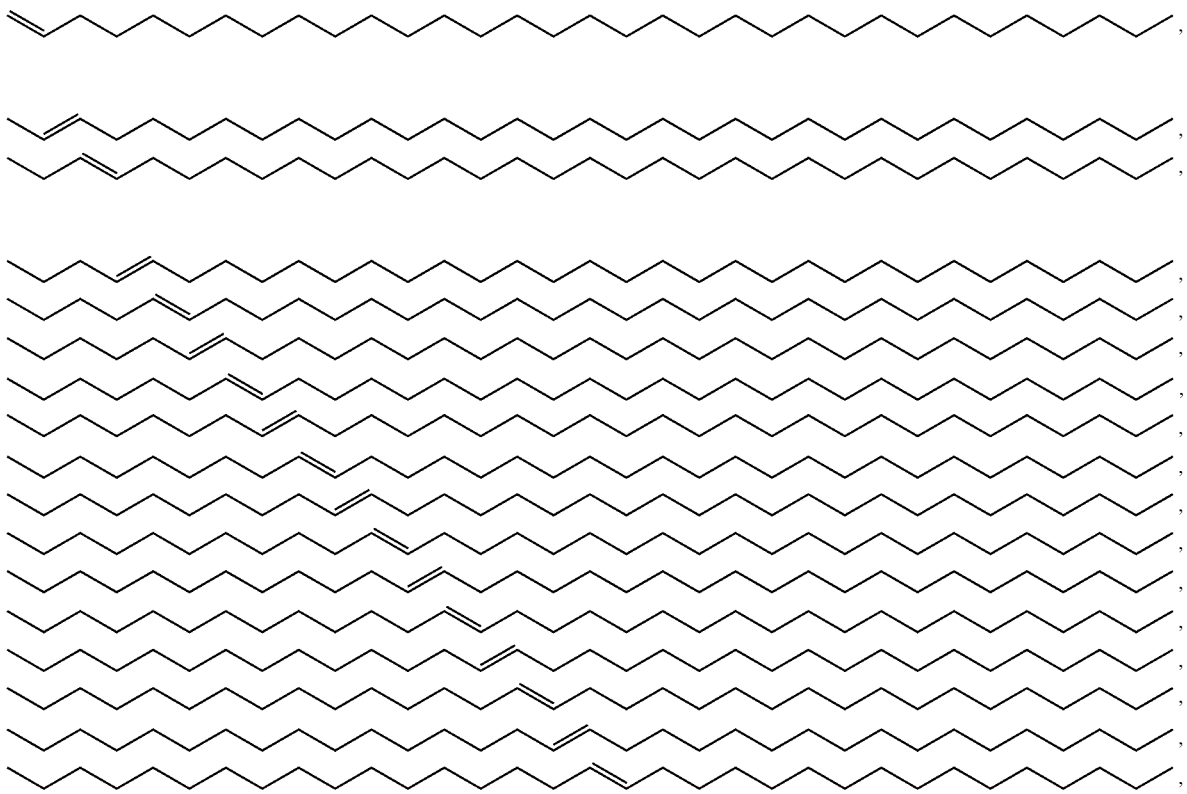

or agriculturally acceptable derivatives thereof. In one embodiment, the tritriacontene is a cis-isomer. In one embodiment, the tritriacontene is of the structure:

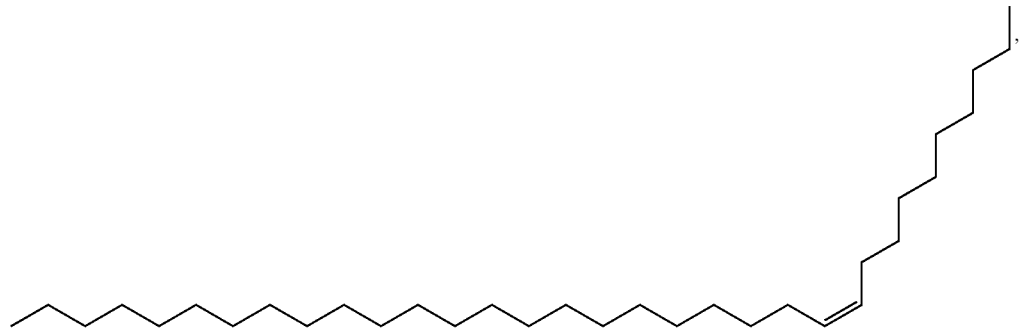 [SMILES: CCCCCCCCC/C=C\CCCCCCCCCCCCCCCCCCCCCC]

or an agriculturally acceptable derivative thereof.

In other embodiments, the presently disclosed subject matter is directed to a method of inducing hygienic behavior in honey bees, the method comprising contacting hive cells with a composition comprising a mite-infested brood extract and an agriculturally acceptable diluent or carrier, wherein the mite-infested brood extract is in an effective amount for inducing hygienic behavior in honey bees. In one embodiment, the mite-infested brood extract has a concentration of 3, 1, or 0.3 brood equivalents.

In another embodiment, the hygienic behavior comprises eating diseased brood or diseased honeybees, removing diseased brood or diseased honeybees from hive cells, removing pests or parasites, uncapping hive cells, or uncapping and recapping hive cells. In a further embodiment, the diseased brood or diseased honeybees are infested with pests or parasites; infected with a pathogen; or damaged. In a further embodiment, the diseased brood or diseased honeybees are infested with mites; more particularly, wherein the mites are mites of the genus *Varroa*; particularly wherein the mites are mites of the species *Varroa destructor* or *Varroa jacobsoni*. In another embodiment, the hygienic behavior results in survival of a honey bee colony. In another embodiment, the hygienic behavior results in suppression of mite reproduction, decreased mite survival, or suppression of a mite infestation. In another embodiment, the hive cells are capped hive cells or uncapped hive cells. In another embodiment, the contacting of the hive cells is on one or more days after the hive cells are capped. In another embodiment, the contacting of the hive cells is on one or more days before the hive cells are capped. In another embodiment, the hive cells are worker-brood cells, drone-brood cells, or queen bee cells. In yet another embodiment the diseased brood are eggs, larvae, or pupae.

In additional embodiments, the presently disclosed subject matter is directed to a method for selecting one or more honey bee(s) exhibiting hygienic behavior comprising a) applying a tritriacontene composition to a set of hive cells; b) performing an assay to identify a hygienic colony, wherein the assay comprises exposing the set of hive cells to a test colony; and c) selecting one or more honey bee(s) from an identified hygienic colony, wherein the selected one or more honey bee(s) exhibit hygienic behavior. In further embodiments, the set of hive cells contains a diseased brood, diseased honey bees, or pests or parasites. In another embodiment, the tritriacontene composition comprises a tritriacontene and an agriculturally acceptable diluent or carrier, wherein the tritriacontene is in an effective amount for inducing hygienic behavior in honey bees. In a further embodiment, the tritriacontene is a stereoisomer, racemic mixture or optically active mixture. The various stereoisomers include geometric isomers/diastereomers (e.g. cis-isomers and trans-isomers, also referred to as Z-isomers and E-isomers) and enantiomers; and refers to isomers that differ only in the way the atoms are arranged in space. In one embodiment, the tritriacontene is a trans-isomer. In one embodiment, the tritriacontene is of the structure:

-continued

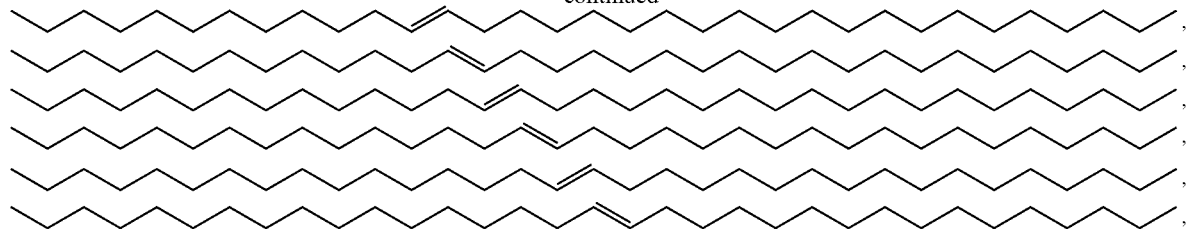

or agriculturally acceptable derivatives thereof. In one embodiment, the tritriacontene is a cis-isomer. In one embodiment, the tritriacontene is of the structure:

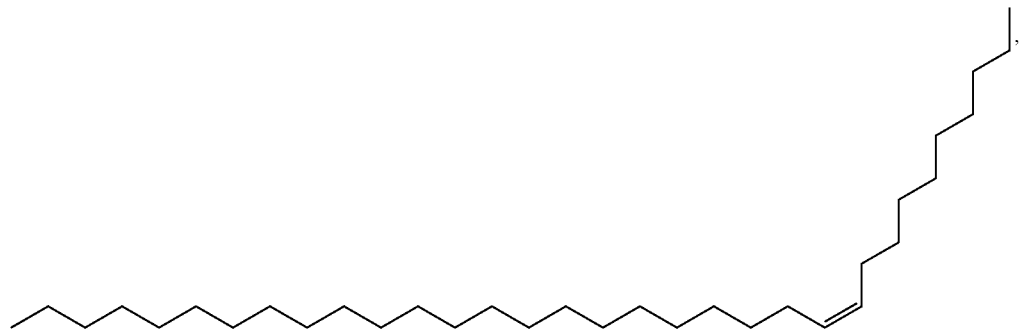 [SMILES: CCCCCCCCC/C=C\CCCCCCCCCCCCCCCCCCCCCC]

or an agriculturally acceptable derivative thereof.

In additional embodiments, the presently disclosed subject matter is directed to a method for selecting one or more honey bee(s) exhibiting hygienic behavior comprising a) applying a mite-infested brood extract composition to a set of hive cells; b) performing an assay to identify a hygienic colony, wherein the assay comprises exposing the set of hive cells to a test colony; and c) selecting one or more honey bee(s) from an identified hygienic colony, wherein the selected one or more honey bee(s) exhibit hygienic behavior. In further embodiments, the set of hive cells contains a diseased brood, diseased honey bees, or pests or parasites. In another embodiment, the mite-infested brood extract composition comprises a mite-infested brood extract and an agriculturally acceptable diluent or carrier, wherein the mite-infested brood extract is in an effective amount for inducing hygienic behavior in honey bees. In one embodiment, the mite-infested brood extract has a concentration of 3, 1, or 0.3 brood equivalents.

In another embodiment, each of the selected honey bee(s) is a queen bee or drone bee. In another embodiment, the assay further comprises i) determining the amount of emptied hive cells in the set of hive cells; and ii) identifying a hygienic colony, wherein a test colony is a hygienic colony if at least 90% of the set of hive cells are emptied; more particularly wherein the emptied hive cells have no eggs, larvae, or pupae, or contain partially eaten larvae or pupae; particularly wherein the emptied hive cells are capped hive cells or uncapped hive cells. In another embodiment, the emptied hive cells have no diseased honey bees, or contain partially eaten diseased honey bees. In another embodiment, the hive cells are capped hive cells and the assay further comprises i) determining the amount of uncapped and/or recapped hive cells in the set of capped hive cells; and ii) identifying a hygienic colony, wherein a test colony is a hygienic colony if at least 90% of the set of capped hive cells are uncapped and/or recapped.

In another embodiment, the method further comprises d) mating a selected honey bee with one or more honey bee(s) from at least one separately identified hygienic colony to produce offspring. In another embodiment, the method further comprises e) raising the offspring, f) applying a tritriacontene composition to a second set of hive cells, g) performing a second assay to identify whether the raised offspring is a hygienic colony, wherein the second assay comprises exposing the second set of hive cells to the raised offspring, and h) selecting one or more honey bee(s) from an identified hygienic colony, wherein the selected one or more honey bee(s) exhibit hygienic behavior. In further embodiments, the second set of hive cells contains a diseased brood, diseased honey bees, or pests or parasites. In another embodiment, the tritriacontene composition comprises a tritriacontene and an agriculturally acceptable diluent or carrier, wherein the tritriacontene is in an effective amount for inducing hygienic behavior in honey bees. In a further embodiment, the tritriacontene is a stereoisomer, racemic mixture or optically active mixture. The various stereoisomers include geometric isomers/diastereomers (e.g. cis-isomers and trans-isomers, also referred to as Z-isomers and E-isomers) and enantiomers; and refers to isomers that differ only in the way the atoms are arranged in space. In one embodiment, the tritriacontene is a trans-isomer. In one embodiment, the tritriacontene is of the structure:

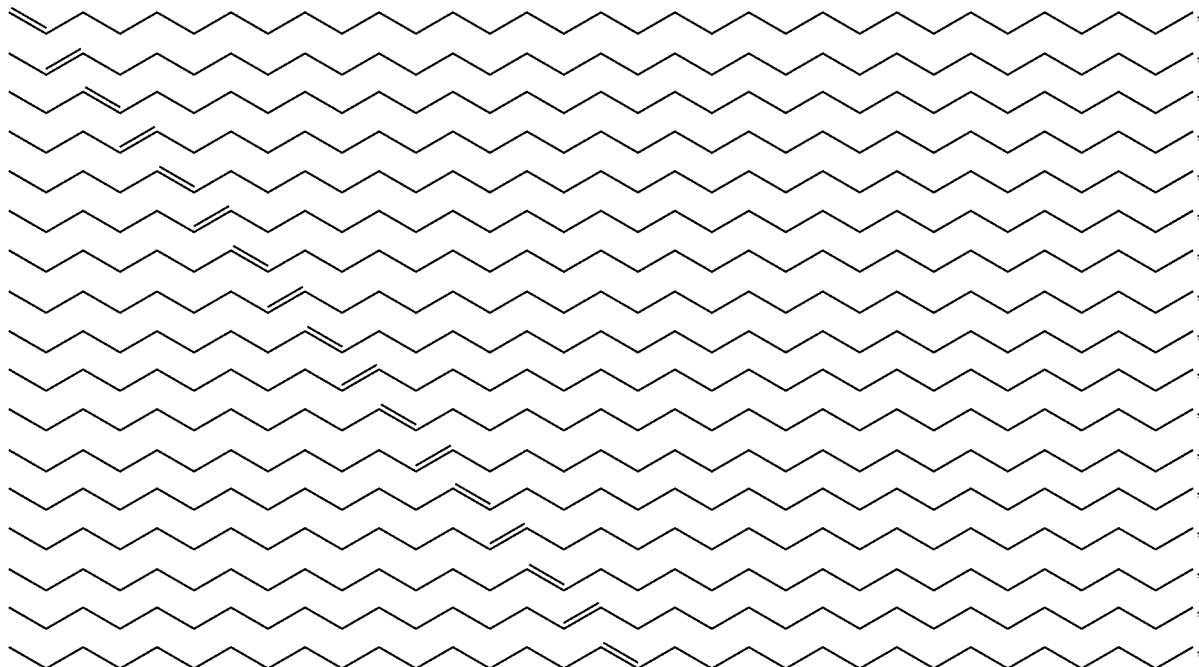

or agriculturally acceptable derivatives thereof. In one embodiment, the tritriacontene is a cis-isomer. In one embodiment, the tritriacontene is of the structure:

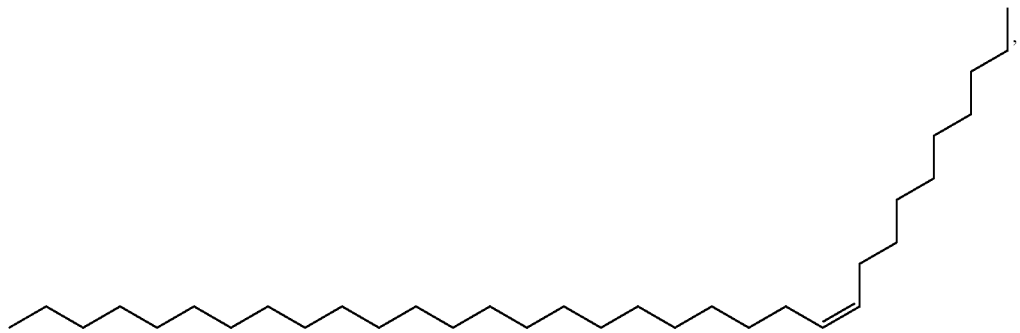 [SMILES: CCCCCCCCC/C=C\CCCCCCCCCCCCCCCCCCCCCC]

or an agriculturally acceptable derivative thereof.

In another embodiment, the method further comprises d) mating a selected honey bee with one or more honey bee(s) from at least one separately identified hygienic colony to produce offspring. In another embodiment, the method further comprises e) raising the offspring, f) applying a mite-infested brood extract composition to a second set of hive cells, g) performing a second assay to identify whether the raised offspring is a hygienic colony, wherein the second assay comprises exposing the second set of hive cells to the raised offspring, and h) selecting one or more honey bee(s) from an identified hygienic colony, wherein the selected one or more honey bee(s) exhibit hygienic behavior. In further embodiments, the second set of hive cells contains a diseased brood, diseased honey bees, or pests or parasites. In another embodiment, the mite-infested brood extract composition comprises a mite-infested brood extract and an agriculturally acceptable diluent or carrier, wherein the mite-infested brood extract is in an effective amount for inducing hygienic behavior in honey bees. In one embodiment, the mite-infested brood extract has a concentration of 3, 1, or 0.3 brood equivalents.

In another embodiment, the second assay further comprises i) determining the amount of emptied hive cells in the second set of hive cells; and ii) identifying a hygienic colony, wherein the raised offspring is a hygienic colony if at least 90% of the second set of hive cells are emptied. In another embodiment, the emptied hive cells are capped hive cells or uncapped hive cells. In another embodiment, the hive cells are capped hive cells and the second assay further comprises i) determining the amount of uncapped and/or recapped hive cells in the second set of capped hive cells; and ii) identifying a hygienic colony, wherein the raised offspring is a hygienic colony if at least 90% of the second set of capped hive cells are uncapped and/or recapped.

In some embodiments, the presently disclosed subject matter is directed to a method for assessing the degree of hygienic behavior within a honey bee colony comprising a) applying a tritriacontene composition to a set of hive cells; b) exposing the set of hive cells to a honey bee colony; and c) determining the amount of emptied hive cells in the set of hive cells; wherein a higher amount of the set of hive cells that are emptied is associated with a greater degree of hygienic behavior. In another embodiment, the emptied hive cells are capped hive cells or uncapped hive cells. In further embodiments, the set of hive cells contains a diseased brood, diseased honey bees, or pests or parasites. In another embodiment, the tritriacontene composition comprises a tritriacontene and an agriculturally acceptable diluent or carrier, wherein the tritriacontene is in an effective amount for inducing hygienic behavior in hone bees. In a further embodiment, the tritriacontene is a stereoisomer, racemic mixture or optically active mixture. The various stereoisomers include geometric isomers/diastereomers (e.g. cis-isomers and trans-isomers, also referred to as Z-isomers and E-isomers) and enantiomers; and refers to isomers that differ only in the way the atoms are arranged in space. In one embodiment, the tritriacontene is a trans-isomer. In one embodiment, the tritriacontene is of the structure:

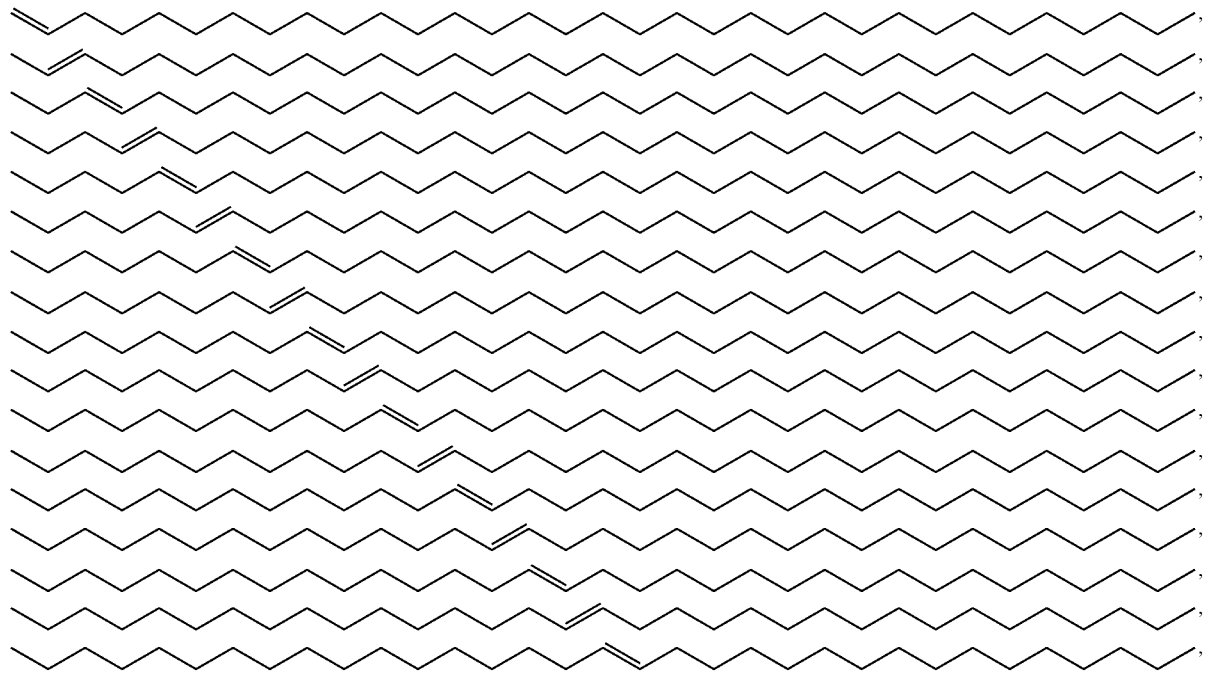

or agriculturally acceptable derivatives thereof. In one embodiment, the tritriacontene is a cis-isomer. In one embodiment, the tritriacontene is of the structure:

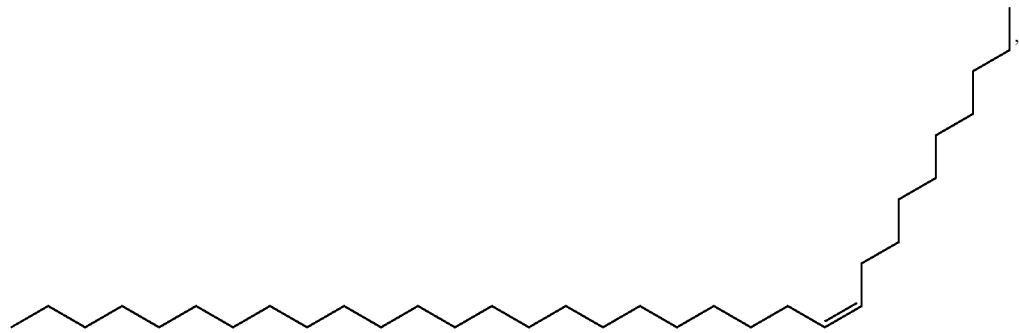 [SMILES: CCCCCCCCC/C=C\CCCCCCCCCCCCCCCCCCCCCC]

or an agriculturally acceptable derivative thereof.

In some embodiments, the presently disclosed subject matter is directed to a method for assessing the degree of hygienic behavior within a honey bee colony comprising a) applying a mite-infested brood extract composition to a set of hive cells; b) exposing the set of hive cells to a honey bee colony; and c) determining the amount of emptied hive cells in the set of hive cells; wherein a higher amount of the set of hive cells that are emptied is associated with a greater degree of hygienic behavior. In another embodiment, the emptied hive cells are capped hive cells or uncapped hive cells. In further embodiments, the set of hive cells contains a diseased brood, diseased honey bees, or pests or parasites. In another embodiment, the mite-infested brood extract composition comprises a mite-infested brood extract and an agriculturally acceptable diluent or carrier, wherein the mite-infested brood extract is in an effective amount for inducing hygienic behavior in honey bees. In one embodiment, the mite-infested brood extract has a concentration of 3, 1, or 0.3 brood equivalents.

In other embodiments, the presently disclosed subject matter is directed to a method for assessing the degree of hygienic behavior within a honey bee colony comprising a) applying a tritriacontene composition to a set of capped hive cells; b) exposing the set of capped hive cells to a honey bee colony; and c) determining the amount of uncapped and/or recapped hive cells in the set of capped hive cells; wherein a higher amount of the set of hive cells that are uncapped and/or recapped is associated with a greater degree of hygienic behavior. In further embodiments, the set of capped hive cells contains a diseased brood, diseased honey bees, or pests or parasites. In another embodiment, the set of capped hive cells is empty. In another embodiment, the tritriacontene composition comprises a tritriacontene and an agriculturally acceptable diluent or carrier, wherein the tritriacontene is in an effective amount for inducing hygienic behavior in honey bees. In a further embodiment, the tritriacontene is a stereoisomer, racemic mixture or optically active mixture. The various stereoisomers include geometric isomers/diastereomers (e.g. cis-isomers and trans-isomers, also referred to as Z-isomers and E-isomers) and enantiomers; and refers to isomers that differ only in the way the atoms are arranged in space. In one embodiment, the tritriacontene is a trans-isomer. In one embodiment, the tritriacontene is of the structure:

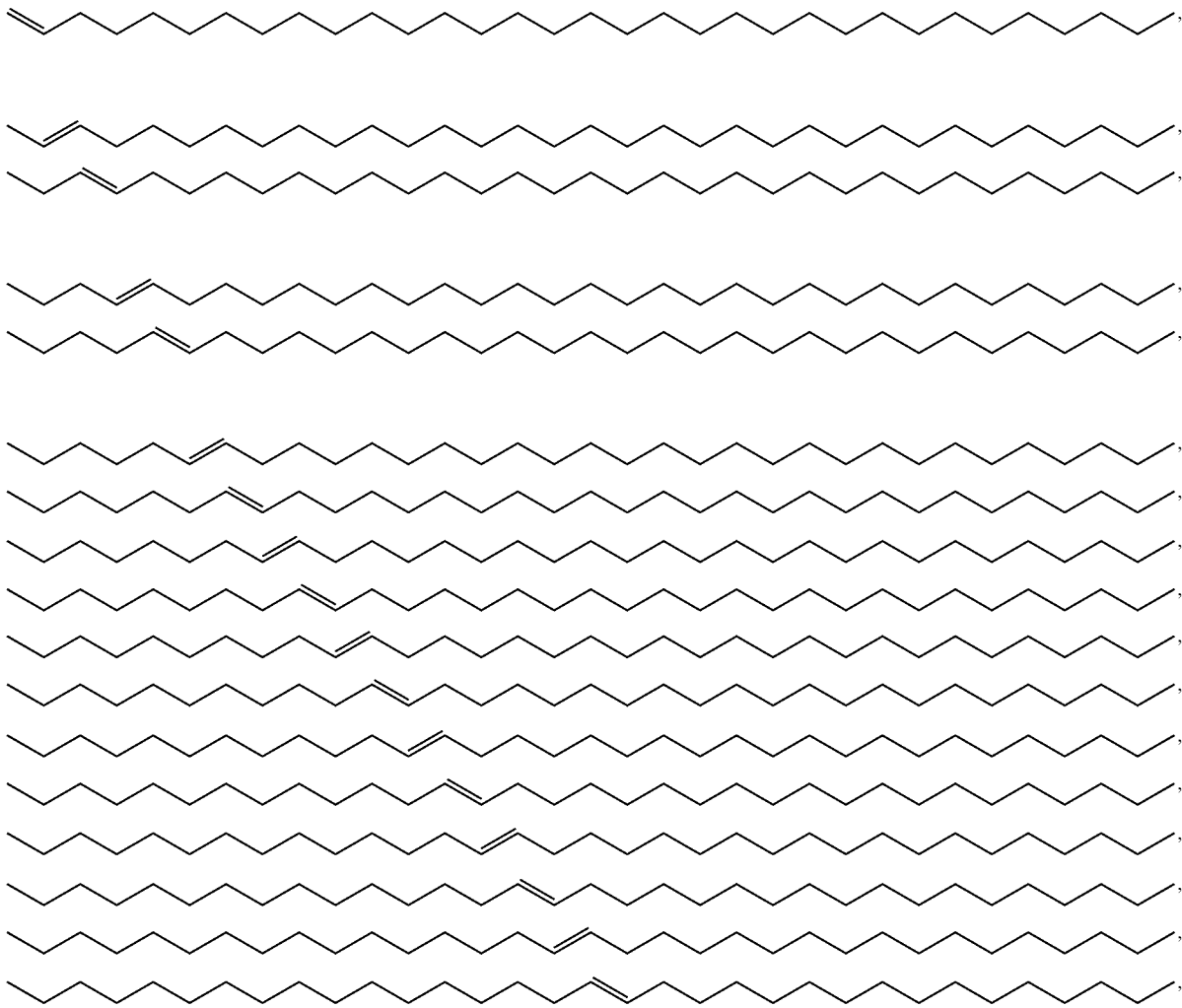

or agriculturally acceptable derivatives thereof. In one embodiment, the tritriacontene is a cis-isomer. In one embodiment, the tritriacontene is of the structure:

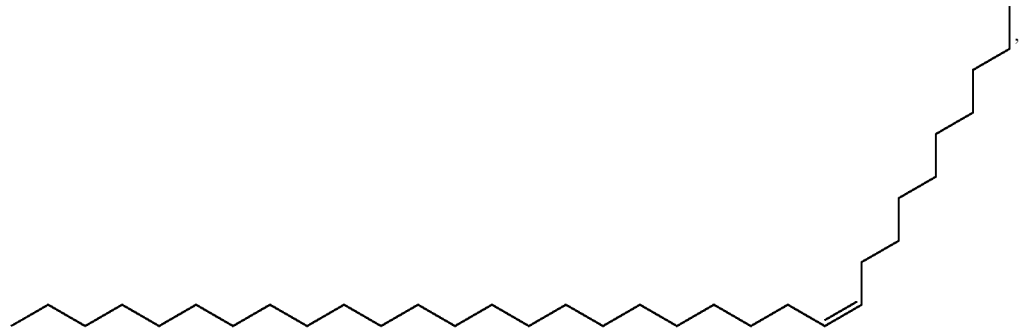 [SMILES: CCCCCCCCC/C=C\CCCCCCCCCCCCCCCCCCCCCC]

or an agriculturally acceptable derivative thereof.

In other embodiments, the presently disclosed subject matter is directed to a method for assessing the degree of hygienic behavior within a honey bee colony comprising a) applying a mite-infested brood extract composition to a set of capped hive cells; b) exposing the set of capped hive cells to a honey bee colony; and c) determining the amount of uncapped and/or recapped hive cells in the set of capped hive cells: wherein a higher amount of the set of hive cells that are uncapped and/or recapped is associated with a greater degree of hygienic behavior. In further embodiments, the set of capped hive cells contains a diseased brood, diseased honey bees, or pests or parasites. In another embodiment, the set of capped hive cells is empty. In another embodiment, the mite-infested brood extract composition comprises a mite-infested brood extract and an agriculturally acceptable diluent or carrier, wherein the mite-infested brood extract is in an effective amount for inducing hygienic behavior in honey bees.

Certain aspects of the presently disclosed subject matter having been stated above, which are addressed in whole or in part by the presently disclosed subject matter, other aspects will become evident as the description proceeds when taken in connection with the accompanying Examples and Figures as best described below.

BRIEF DESCRIPTION OF THE FIGURES

Figure 1:
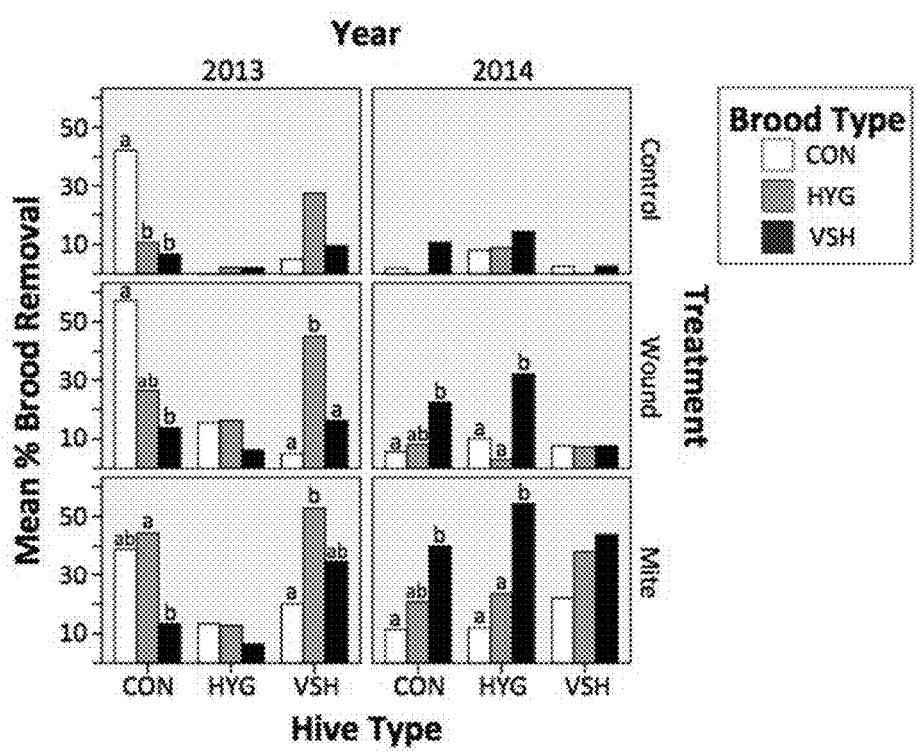

Having thus described the presently disclosed subject matter in general terms, reference will now be made to the accompanying Figures, which are not necessarily drawn to scale, and wherein:

FIG. 1 shows 2013 and 2014 data for treatment, hive type and brood type effects on mean percent brood removal. White, gray and black bars represent control (CON), HYG and VSH brood, respectively. Different letters indicate significant differences from Chi-square analysis after Bonferroni correction (p<0.0167) within each Treatment by Hive Type by Year combination.

Figure 2:
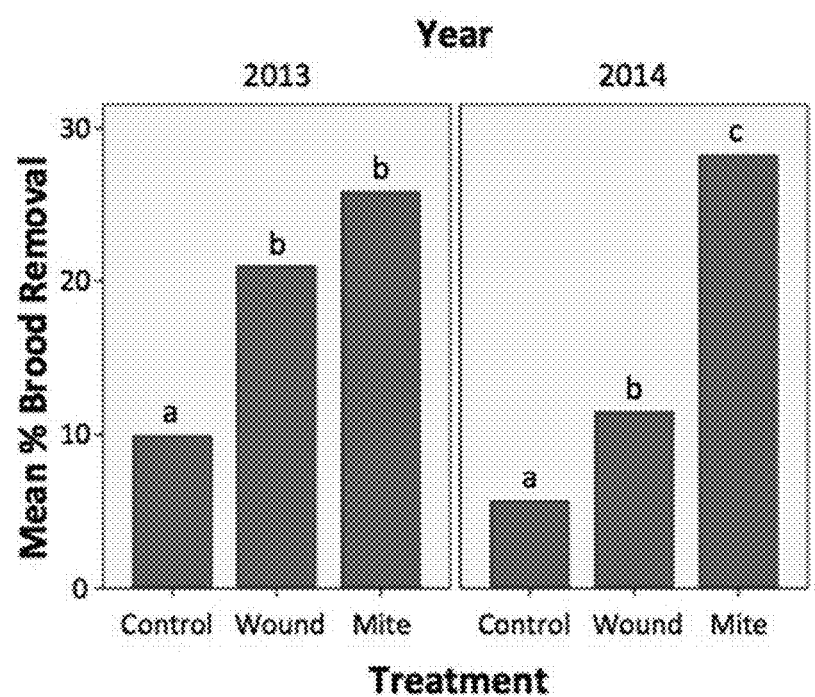

FIG. 2 shows treatment effects on mean percent brood removal. Different letters indicate significant differences from Chi-square analysis (p<0.05).

Figure 3:
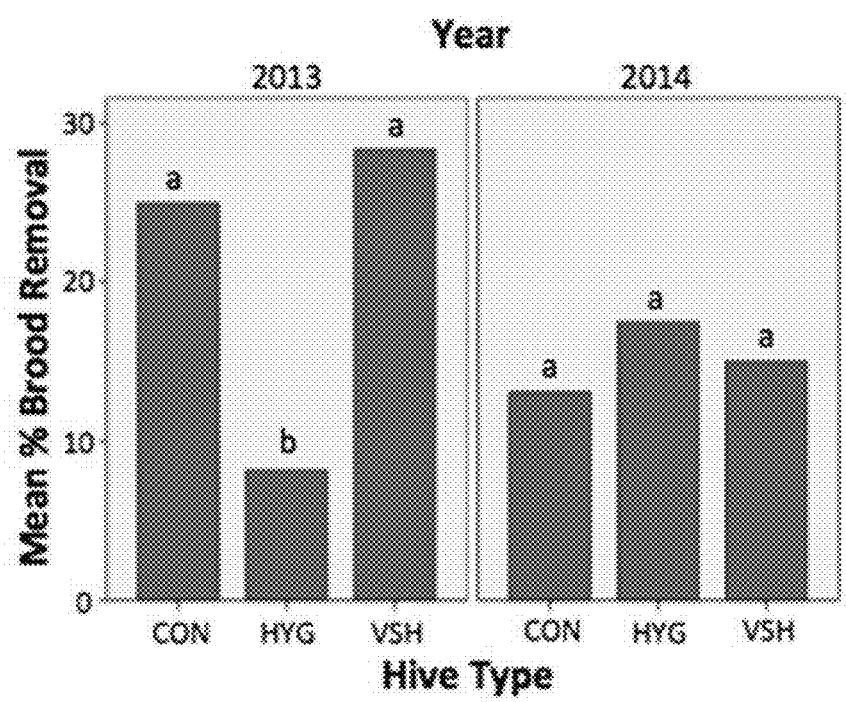

FIG. 3 shows hive type effects on mean percent brood removal. Different letters indicate significant differences from Chi-square analysis (p<0.05).

Figure 4:
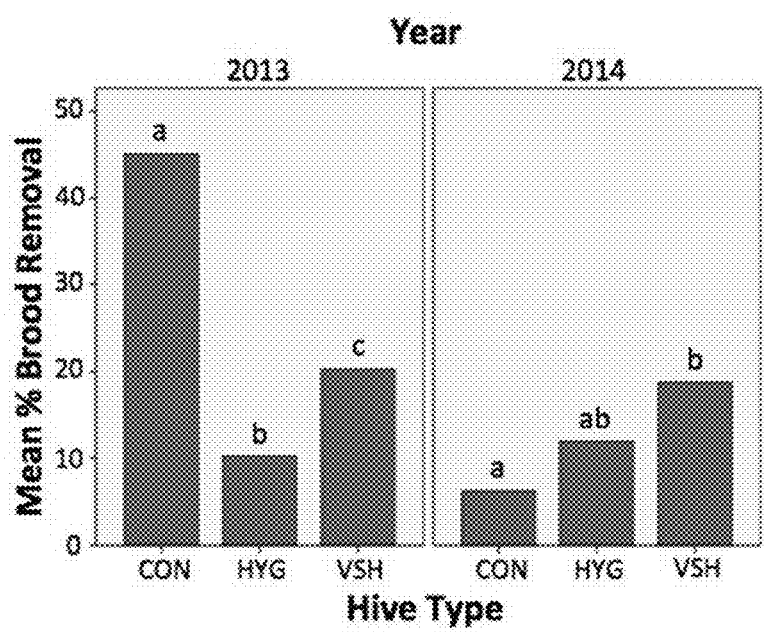

FIG. 4 shows hive type effects on mean percent brood removal for the subset of data in which hive type was the same as brood type. Different letters indicate significant differences from Chi-square analysis (p<0.05).

Figure 5:
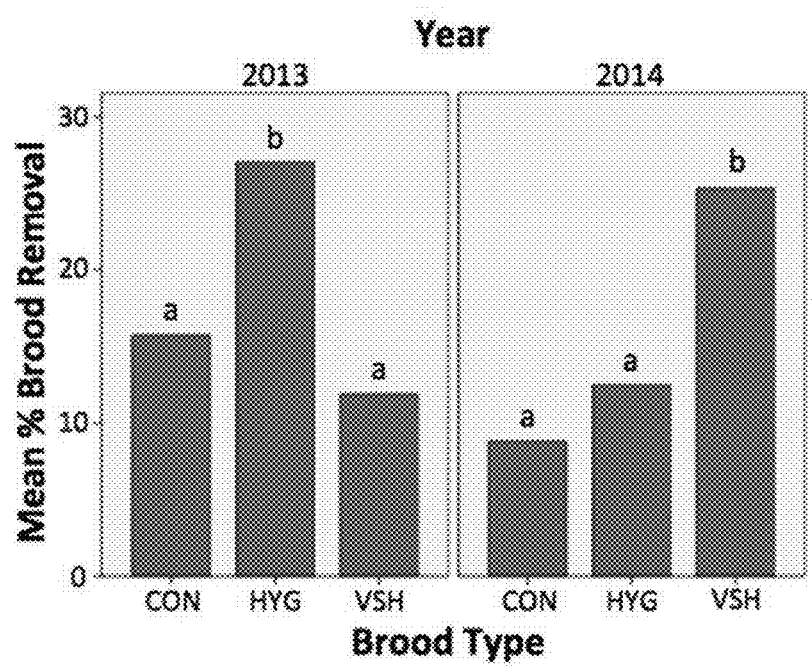

FIG. 5 shows brood type effects on mean percent brood removal. Different letters indicate significant differences from Chi-square analysis (p<0.05).

Figure 6A:
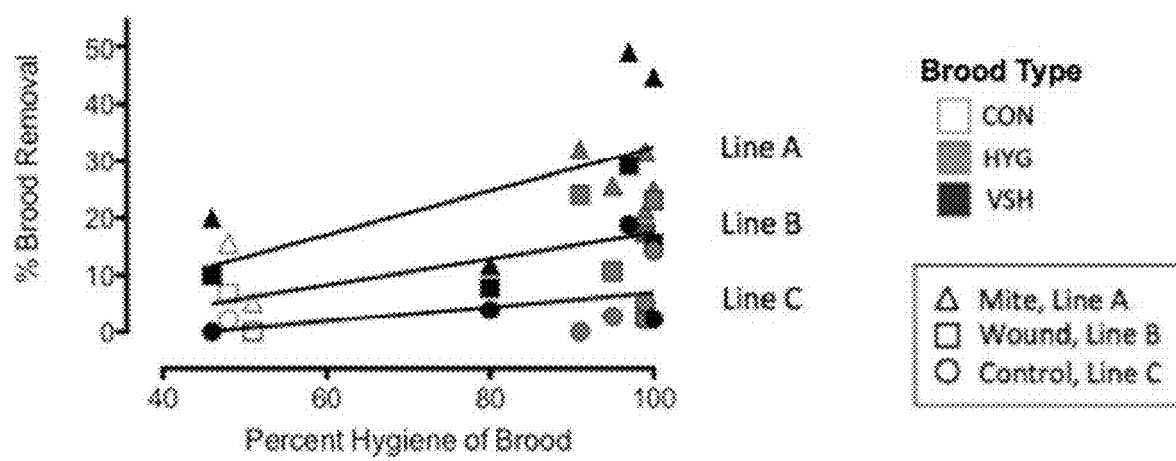

FIG. 6A shows average percent brood removal plotted against the level of hygiene of the brood's hive of origin. White, gray and black symbols represent control (CON), HYG and VSH brood, respectively. Circular, square and triangular markers represent control, wound and mite treatments, and are represented by lines of best fit C, B and A, respectively.

Figure 6B:
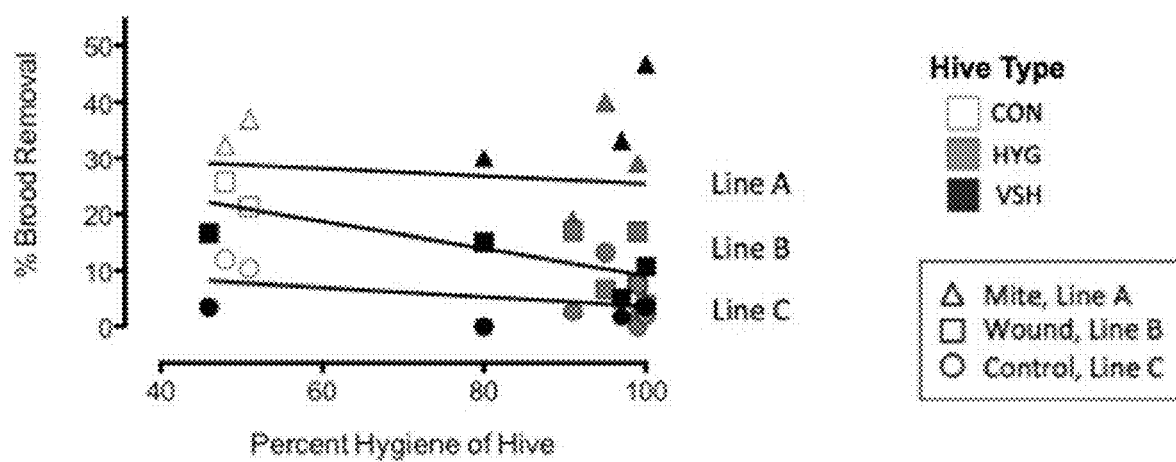

FIG. 6B shows average percent brood removal plotted against the level of hygiene of the brood's host hive. White, gray and black symbols represent control (CON), HYG and VSH hives, respectively. Circular, square and triangular markers represent control, wound and mite treatments, and are represented by lines of best fit C, B and A, respectively.

Figure 7:
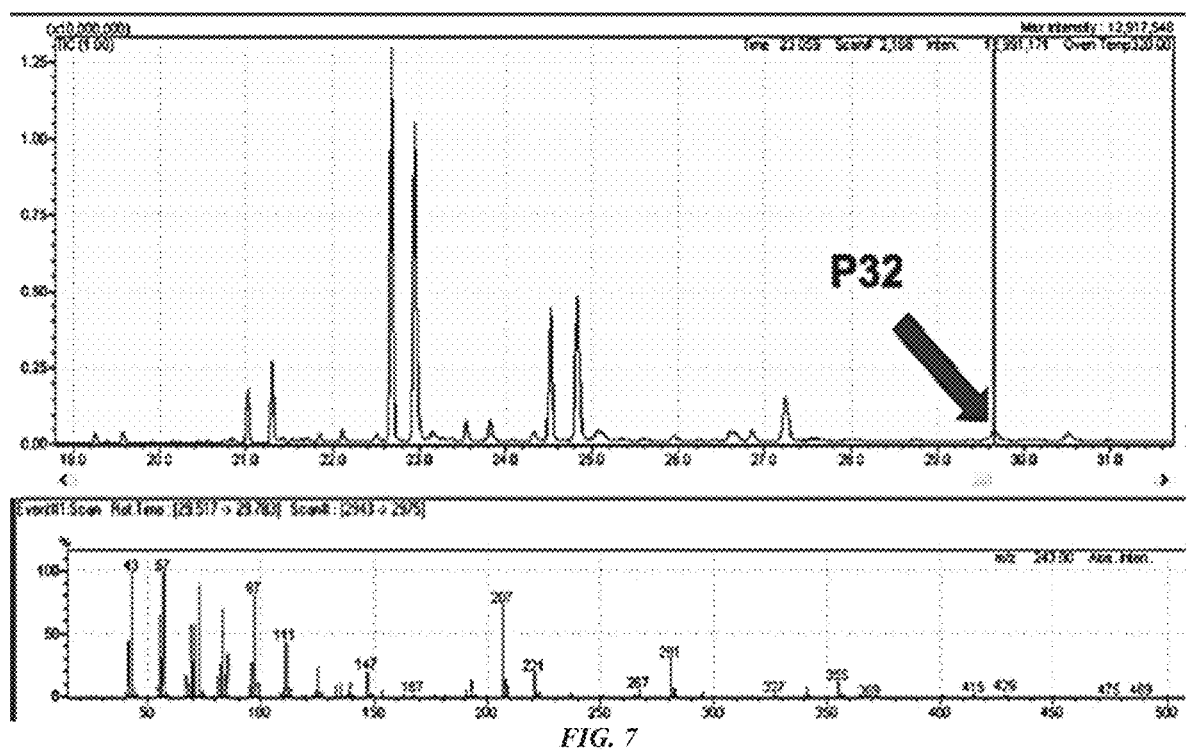

FIG. 7 shows the GCMS output from a single, mite-infested honey bee, illustrating the location of the P32 peak (top) and the mass-to-charge ratio for P32 (bottom).

Figure 8A:
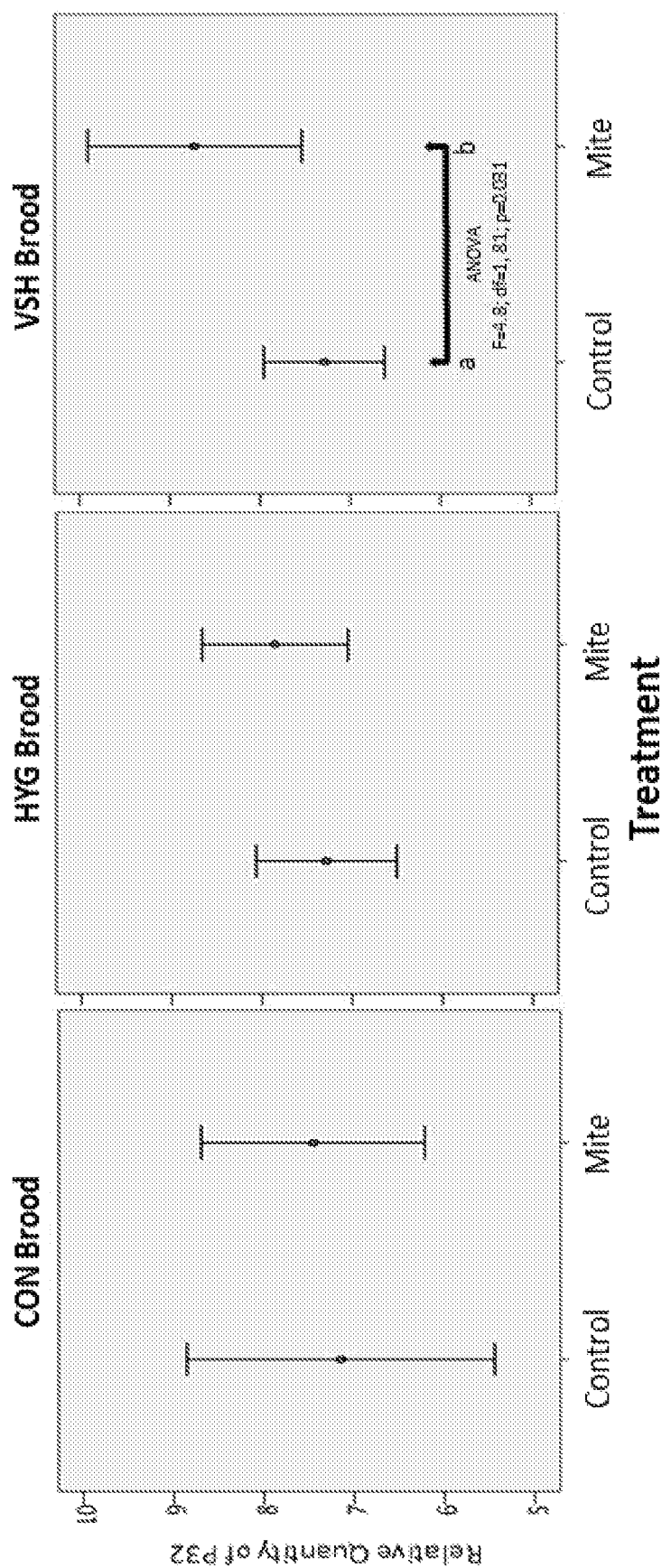
Figure 8B:
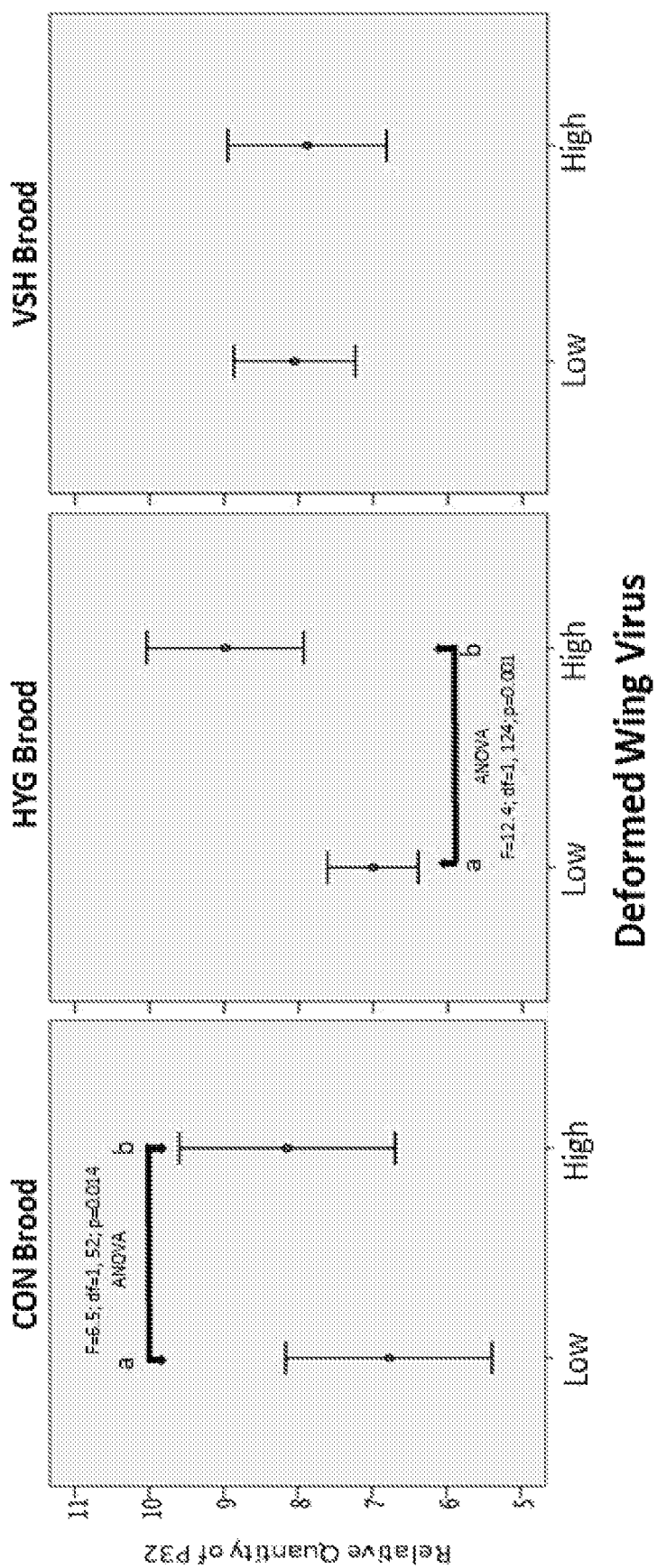

FIG. 8A and FIG. 8B shows the relative quantity of peak number 32 (P32) (a tritriacontene) in a control treatment brood subset versus a Varroa mite-treated brood subset in three types of brood (control (CON) Brood, HYG Brood, and VSH brood), based on averages of samples of each type of brood; and the relative quantity of P32 in a brood subset with low levels of Deformed Wing Virus versus a brood subset with high levels of Deformed Wing Virus in three types of brood (control (CON) Brood, HYG Brood, and VSH Brood), based on averages of samples of each type of brood. All relative quantities of P32 are based on brood extract analysis using Gas Chromatography Mass Spectrometry (GCMS). From ANOVAs: p=0.031 for VSH mite-treated brood subset vs. VSH control brood subset; p=0.014 for Control brood subset with high levels of Deformed Wing Virus vs. Control brood subset with low levels of Deformed Wing Virus; p=0.001 for HYG brood subset with high levels of Deformed Wing Virus vs. Control brood subset with low levels of Deformed Wing Virus.

Figure 9A:
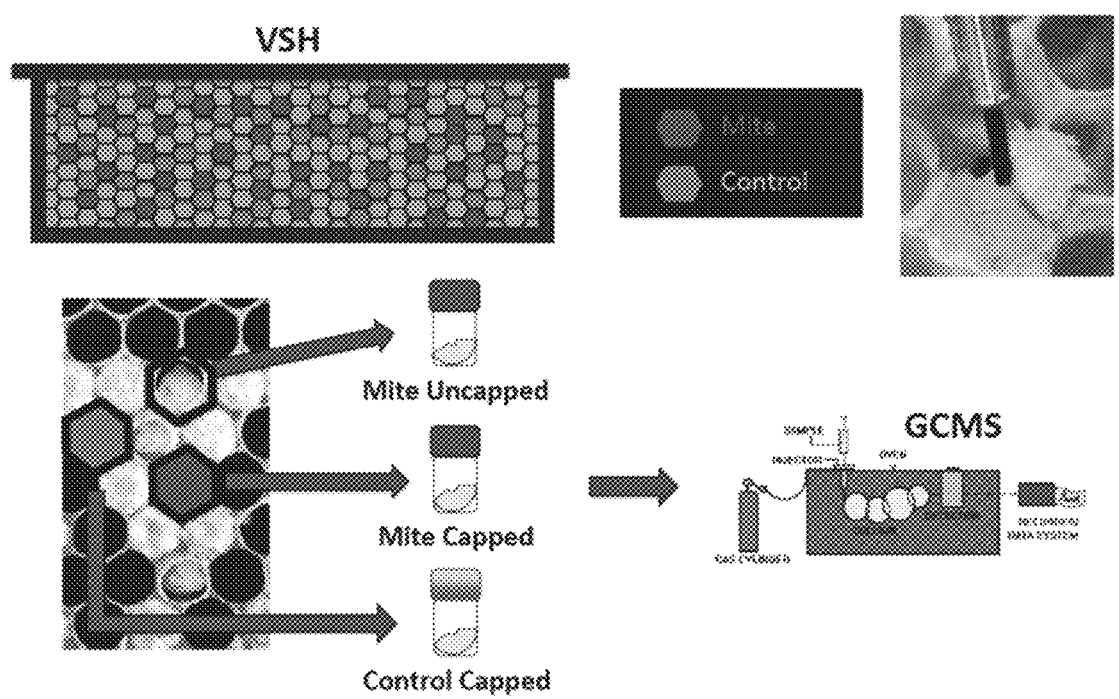

FIG. 9A shows a graphic depicting a set of hive cells with Varroa-infested brood (dark shading) and control brood (medium shading); an image depicting a fine-tipped paint brush introducing Varroa to an opened hive cell that had been recently capped; a graphic depicting an uncapped hive cell with Varroa-infested brood, a capped hive cell with Varroa-infested brood, and a capped hive cell with control brood; and a graphic depicting the Gas Chromatography—Mass Spectrometry (GCMS) setup to determine relative P32 quantities from the brood extracts.

Figure 9B:
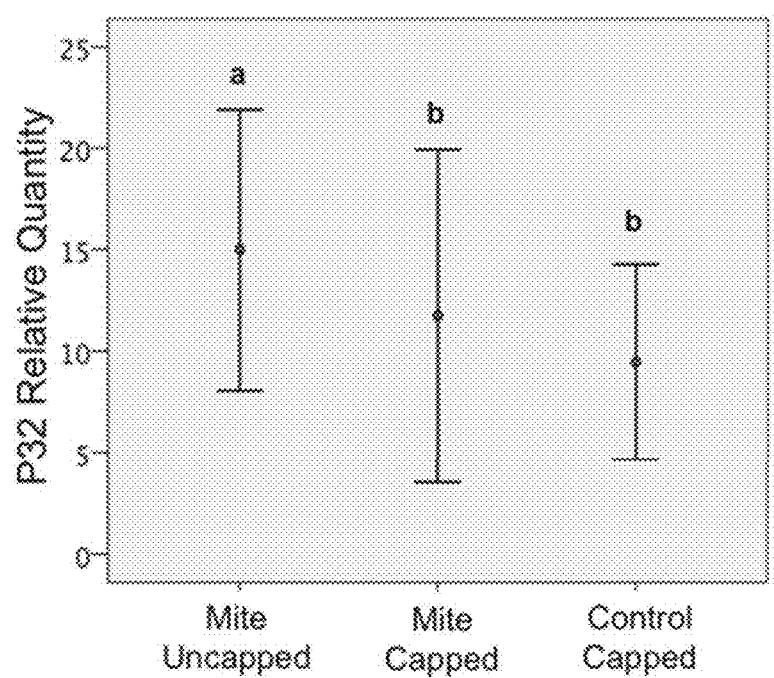

FIG. 9B shows the relative quantity of P32 of the brood extract from uncapped hive cells with *Varroa*-infested brood, the brood extract from capped hive cells with *Varroa*-infested brood, and the brood extract from capped hive cells with control brood. Each relative quantity of P32 is based on an average of six samples for each cell type. Different letters indicate statistically significant differences ($p<0.05$) as determined from a paired-sample t-test.

Figure 9C:
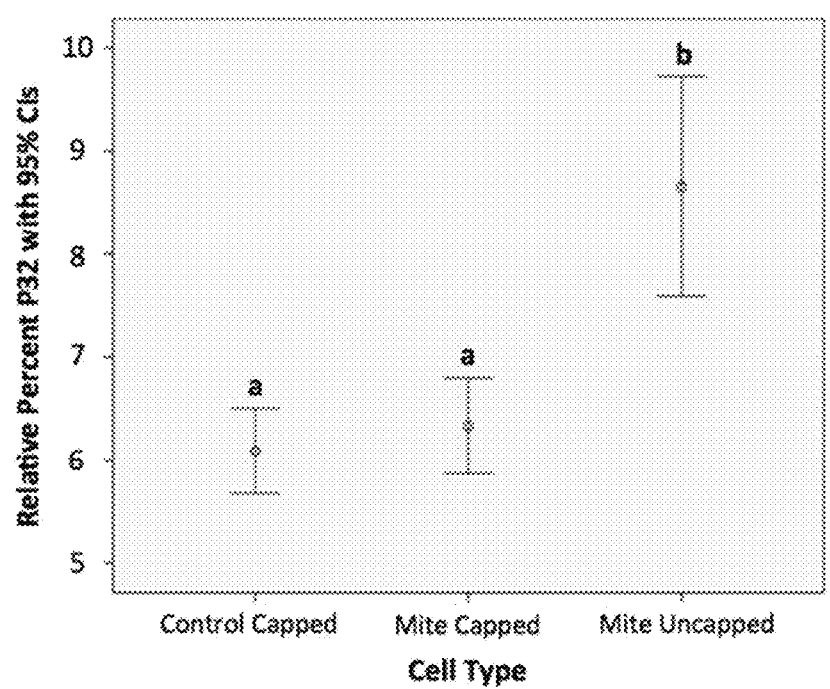

FIG. 9C shows the relative quantity of P32 quantity of the brood extract from uncapped hive cells with *Varroa*-infested brood, the brood extract from capped hive cells with *Varroa*-infested brood, and the brood extract from capped hive cells with control brood. For each mean, 95% CI intervals are provided. Different letters indicate a statistically significant difference ($p<0.0167$) in mean P32 quantity between cell types as determine by ANOVA. Each relative quantity of P32 is based on an average of 24 samples for each cell type.

Figure 10:
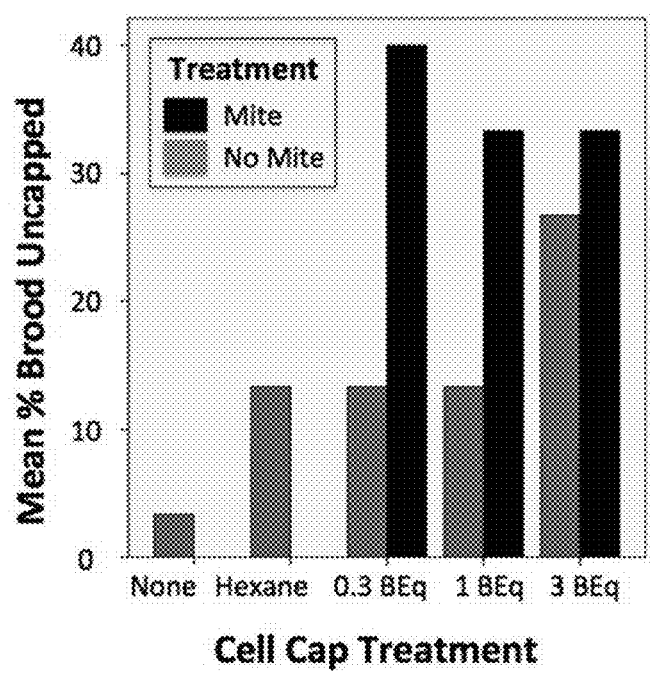

FIG. 10 shows the mean percent of brood cells uncapped 8 hours after no treatment (none), treatment with hexane, treatment with control (not mite-infested) brood extract (at three concentrations: 3, 1 or 0.3 brood equivalents (BEqs)), and treatment with mite-infested brood extract (at three concentrations: 3, 1 or 0.3 BEqs). Mean percent of brood cells uncapped is based on a sample size of 30 cells each for no treatment and hexane treatment, and 15 cells for each brood extract concentration.

Figure 11:
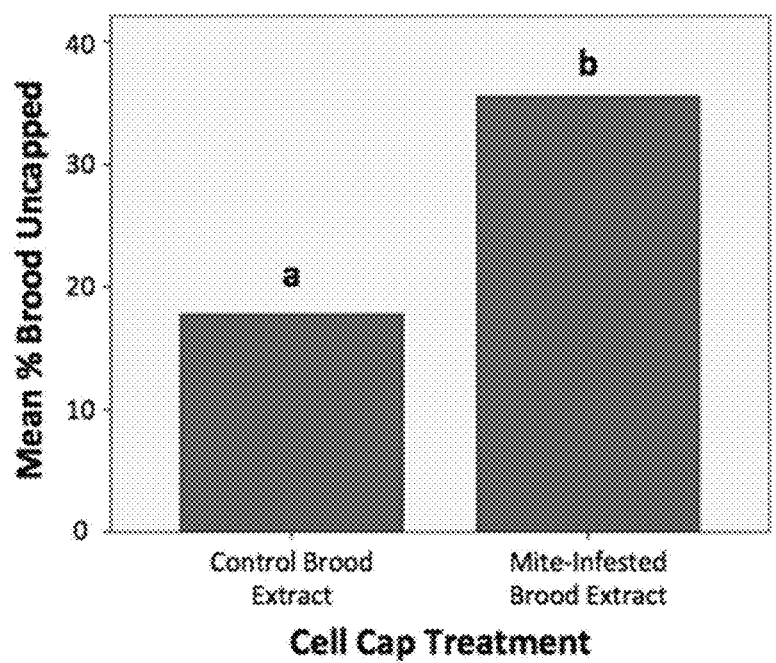

FIG. 11 shows the mean percent of brood cells uncapped 8 hours after treatment with control (not mite-infested) brood extract from control and treatment with mite-infested brood extract. Each bar represents a combination of data from like treatments for all three brood extract concentrations as shown in FIG. 10. Thus each bar is based on a sample size of 45 cells. Different letters indicate a statistically significant difference ($p<0.05$) as determined from a Chi-square test.

Figure 12:
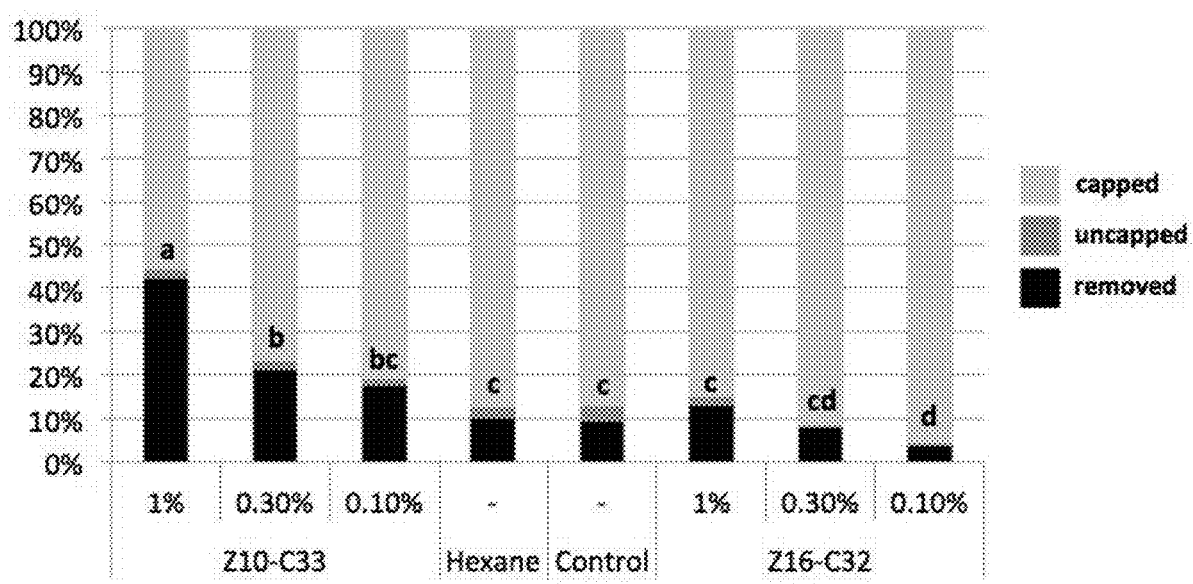

FIG. 12 shows the percent uncapping and removal of brood underneath treated wax caps after 24 hours. Using the airbrushing method, approximately 10 µl of solvent were applied to each chemically treated cell. Different letters indicate a statistically significant difference ($p<0.0018$) as determined from Chi-square tests with Bonferroni correction.

Figure 13:
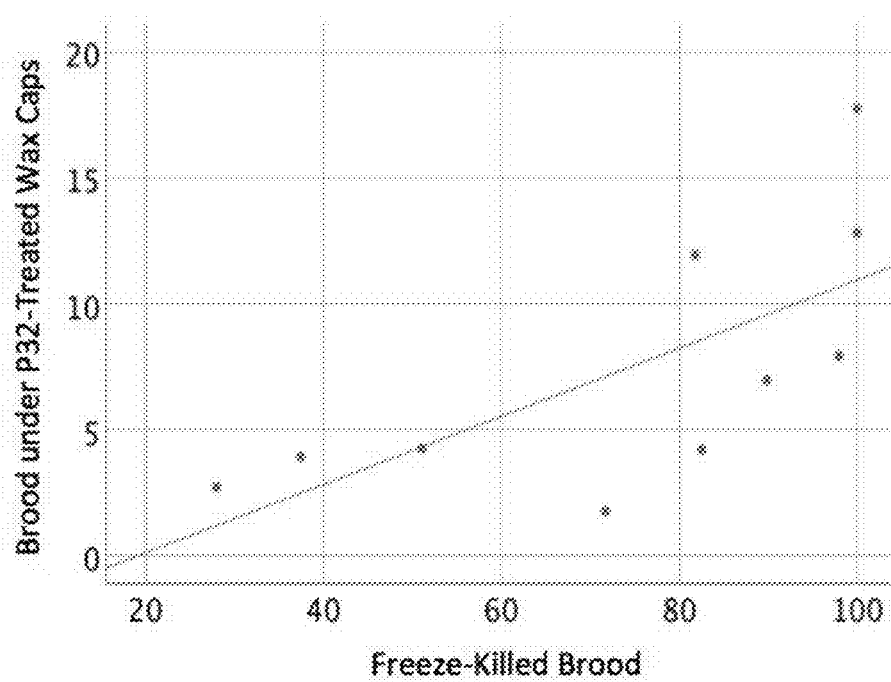

FIG. 13 shows a significant positive correlation between the complete removal of brood treated with P32 at 24 hours and brood treated with liquid nitrogen (FKB assay).

BRIEF DESCRIPTION OF THE SEQUENCE LISTING

SEQ ID NO: 1 represents the DWV forward primer.
SEQ ID NO: 2 represents the DWV reverse primer.
SEQ ID NO: 3 represents the Actin forward primer.
SEQ ID NO: 4 represents the Actin reverse primer.
SEQ ID NO: 5 represents the RPSS forward primer.
SEQ ID NO: 6 represents the RPSS reverse primer.

DETAILED DESCRIPTION

The presently disclosed subject matter now will be described more fully hereinafter with reference to the accompanying Figures, in which some, but not all embodiments of the presently disclosed subject matter are shown. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Figures. Therefore, it is to be understood that the presently disclosed subject matter is not to be limited to the specific embodiments disclosed and that modifications and other embodiments are intended to be included within the scope of the appended claims.

Unless defined otherwise, all technical and scientific terms used herein have the same meanings as commonly understood by one of ordinary skill in the art to which this disclosure belongs. Preferred methods, devices, and materials are described, although any methods and materials similar or equivalent to those described herein can be used in the practice or testing of the present disclosure.

Throughout the present specification, numerical ranges are provided for certain quantities. It is to be understood that these ranges comprise all subranges therein. Thus, the range "from 50 to 80" includes all possible ranges therein (e.g., 51-79, 52-78, 53-77, 54-76, 55-75, 60-70, etc.). Furthermore, all values within a given range may be an endpoint for the range encompassed thereby (e.g., the range 50-80 includes the ranges with endpoints such as 55-80, 50-75, etc.).

The presently disclosed subject matter provides tritriacontene compositions for inducing hygienic behavior in honey bees; mite-infested brood extract compositions for inducing hygienic behavior in honey bees; methods of inducing hygienic behavior in honey bees: methods of selecting one or more honey bee(s) exhibiting hygienic behavior, and methods for assessing the degree of hygienic behavior within a honey bee colony. As described more fully below, the presently disclosed subject matter relates to the finding that a tritriacontene compound triggers hygienic behavior in honey bees I. Compositions In some embodiments, the presently disclosed subject matter is directed to a composition for inducing hygienic behavior in honey bees comprising a tritriacontene and an agriculturally acceptable diluent or carrier, wherein the tritriacontene is in an effective amount for inducing hygienic behavior in honey bees. As used herein, the term "tritriacontene" refers to a compound with the molecular formula $C_{33}H_{66}$. In a further embodiment, the tritriacontene is a stereoisomer, racemic mixture or optically active mixture. The various stereoisomers include geometric isomers/diastereomers (e.g. cis-isomers and trans-isomers, also referred to as Z-isomers and E-isomers) and enantiomers: and refers to isomers that differ only in the way the atoms are arranged in space. In one embodiment, the tritriacontene is a trans-isomer. In one embodiment, the tritriacontene is of the structure:

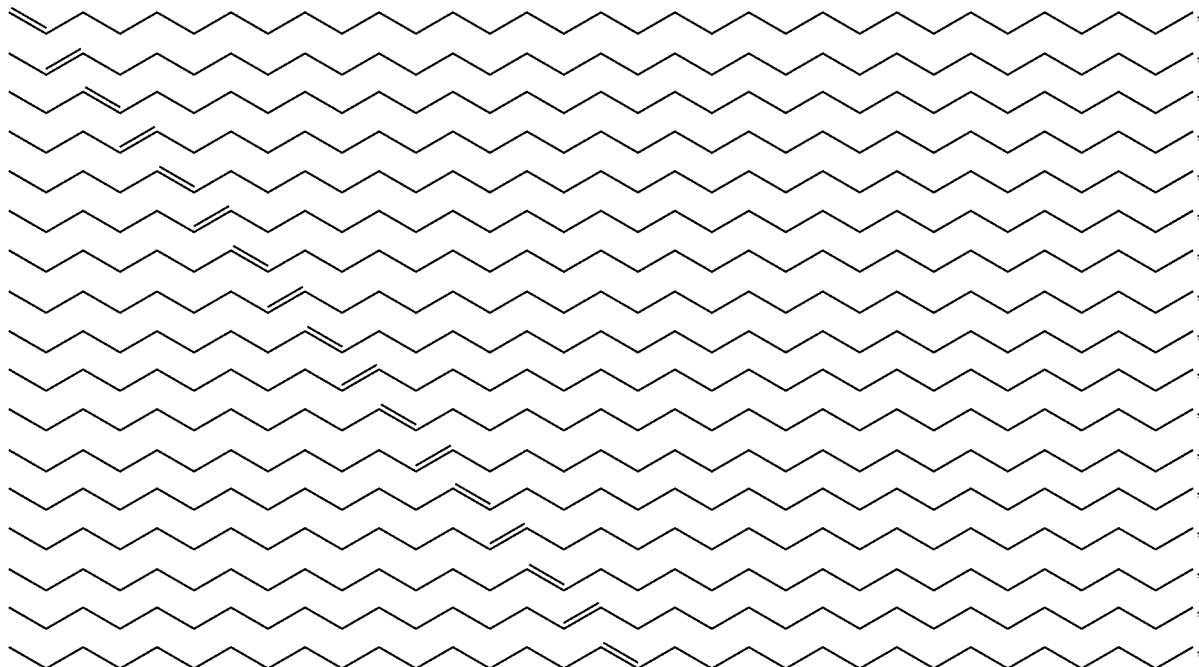

or agriculturally acceptable derivatives thereof. In one embodiment, the tritriacontene is a cis-isomer. In one embodiment, the tritriacontene is of the structure:

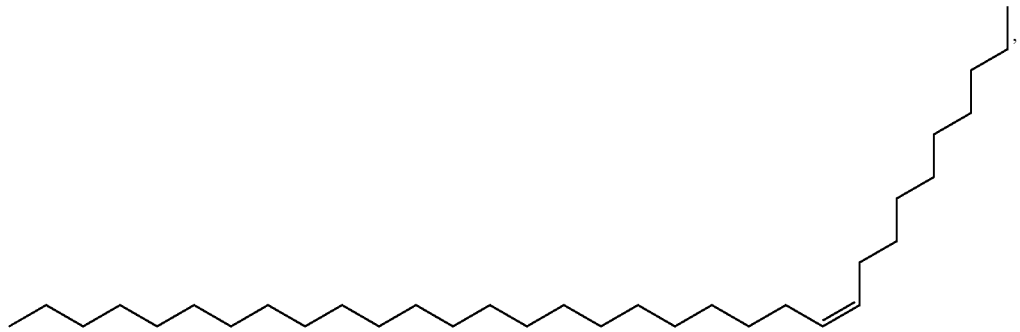 [SMILES: CCCCCCCCC/C=C\CCCCCCCCCCCCCCCCCCCCCC]

or an agriculturally acceptable derivative thereof. It will be appreciated by those skilled in the art that one stereoisomer may be more active than the others. Individual stereoisomers and optically active mixtures may be obtained by selective synthetic procedures, by conventional synthetic procedures using resolved starting materials, or by conventional resolution procedures.

As used herein, the term "agriculturally acceptable derivative" refers to any agriculturally acceptable salt, ester, or salt of such ester, of such compound, or any other adduct or derivative which, upon administration, is capable of providing (directly or indirectly) a compound as otherwise described herein, or residue thereof. Materials and methods for derivatizing the parent compounds are known and may be adapted to the present invention. Certain exemplary pharmaceutical compositions and pharmaceutically acceptable derivatives will be discussed in more detail herein below.

As used herein, the term "agriculturally acceptable salt," refers to salts of a free acid or a free base which are not biologically undesirable and are generally prepared by reacting the free base with a suitable organic or inorganic acid or by reacting the acid with a suitable organic or inorganic base. Agriculturally acceptable salts include salts, the cations or anions of which are known in the art for the formation of salts for agricultural or apicultural use. In some embodiments the salts are water-soluble. Suitable cations include the ions of the alkali metals (such as lithium, sodium and potassium), alkaline earth metals (such as calcium, magnesium and barium) and transition metals (such as manganese, copper, zinc and iron), and amines. Suitable anions of acid addition salts are primarily chloride, bromide, fluoride, hydrogen sulfate, sulfate, dihydrogen phosphate, hydrogen phosphate, phosphate, nitrate, hydrogen carbonate, carbonate, hexafluorosilicate, hexafluorophosphate, benzoate, and the anions of $C_1$-$C_4$-alkanoic acids, such as formate, acetate, propionate and butyrate. The term "agriculturally acceptable ester" refers to those that are or can by hydrolyzed, oxidized, metabolized, or otherwise converted, e.g., in plants, water, or soil, to the corresponding carboxylic acid which, depending on the pH, may be in the dissociated or un-dissociated form. Exemplary esters include those derived from $C_1$-$C_{12}$ alkyl, $C_3$-$C_{12}$ alkenyl, $C_3$-$C_{12}$ alkynyl or $C_7$-$C_{10}$ aryl-substituted alkyl alcohols. Esters can be prepared by coupling of the acid with the alcohol using any number of suitable activating agents such as those used for peptide couplings such as dicyclohexylcarbodiimide (DCC) or carbonyl diimidazole (CDI); by reacting the acid with alkylating agents such as alkylhalides or alkylsulfonates in the presence of a base such as triethylamine or lithium carbonate: by reacting the corresponding acid chloride of an acid with an appropriate alcohol; by reacting the corresponding acid with an appropriate alcohol in the presence of an acid catalyst or by transesterification.

In some embodiments, the tritriacontene can form stable complexes with solvent molecules that remain intact after the non-complexed solvent molecules are removed from the compound. These complexes are often referred to as "solvates."

In some embodiments, the presently disclosed subject matter is directed to a composition for inducing hygienic behavior in honey bees comprising a mite-infested brood extract and an agriculturally acceptable diluent or carrier, wherein the mite-infested brood extract is in an effective amount for inducing hygienic behavior in honey bees. As used herein, the term "mite-infested brood extract" refers to extract derived from mite-infested honey bee brood and comprising cuticular chemicals; or extract derived from honey bee brood and comprising cuticular chemicals and artificially added tritriacontene. In one embodiment, the mite-infested brood extract has a concentration of 3, 1, or 0.3 brood equivalents. Mite-infested brood extract may be derived from an individual brood; multiple brood; whole or part of individual brood(s); and living, dead, or damaged brood. Mite-infested brood extract may be obtained using conventional methods, including, but not limited to solvent extraction. Any of a variety of solvents including polar solvents, non-polar solvents, or combinations of two or more thereof may be used in solvent extraction. Suitable non-polar solvents include non-polar organic solvents such as alkanes, including $C_1$-$C_8$ alkanes, cycloalkanes, including $C_1$-$C_8$ alkanes, alkyl ethers, including $C_1$-$C_8$ alkyl ethers, Petroleum ethers, ketones, including $C_1$-$C_8$ ketones, methylene chloride, ethyl acetate, xylene, toluene, chloroform, vegetable oil, mineral oil and the like. In one embodiment, the mite-infested brood extract is obtained from mite-infested honey bee brood by solvent extraction using a hexane solvent. Suitable polar solvents include polar inorganic solvents such as water and the like, polar organic solvents such as alcohols and corresponding organic acids, for example $C_1$-$C_8$ alcohols including methanol, ethanol, propanol, butanol, and the like and organic acids, including acetic acid, formic acid, propanoic acid, and the like, polyols and glycols, including $C_1$-$C_8$ polyols/glycols and the like, and combinations of two or more thereof.

As used herein, the term "agriculturally acceptable diluent or carrier," refers to organic or inorganic material, natural or synthetic, that facilitates application and is agriculturally or apiculturally acceptable on the application surface; such as, adjuvants, mixers, enhancers, or combinations thereof suitable for application of the composition. Examples of suitable liquid agriculturally acceptable carriers include hexane, pentane, water, toluene, xylene, petroleum naphtha, crop oil, acetone, methyl ethyl ketone, cyclohexanone, trichloroethylene, perchloroethylene, ethyl acetate, amyl acetate, butyl acetate, propylene glycol monomethyl ether and diethylene glycol monomethyl ether, methanol, ethanol, isopropanol, amyl alcohol, ethylene glycol, propylene glycol, and glycerine. Exemplary solid agriculturally acceptable carriers include talc, pyrophyllite clay, silica, attapulgus clay, kieselguhr, chalk, diatomaceous earth, lime, calcium carbonate, bentonite clay, Fuller's earth, cotton seed hulls, wheat flour, soybean flour, pumice, wood flour, walnut shell flour, and lignin. Additional adjuvants include antifoam agents, neutralizing agents, buffers, dispersing agents, thickening agents, sequestering agents, and so on.

The presently disclosed subject matter contemplates all vehicles by which the composition of the presently disclosed subject matter can be formulated for delivery and use as solutions, suspensions, emulsions, wettable powders and water dispersible granules, dry flowables, emulsifiable concentrates, granules, dusts, fumigants, gels, microencapsulations, and the like. The compositions can be manufactured in a manner known in the art; for example, without limiting the foregoing, by means of conventional mixing, dissolving, granulating, or emulsifying processes.

Formulations for application to hive cells may be applied following dilution of the concentrated formulation with water as aqueous solutions, suspensions or emulsions, or combinations thereof. Such solutions, suspensions or emulsions are produced from water-soluble, water-suspended or water-suspendable, water-emulsified or water-emulsifiable formulations or combinations thereof which are solids, including wettable powders or water dispersible granules; or liquids including emulsifiable concentrates, aqueous suspensions or suspension concentrates, and aqueous emulsions or emulsions in water, or mixtures thereof such as suspension-emulsions.

Wettable powders, which may be compacted to form water dispersible granules, comprise a mixture of the active ingredient, an inert carrier, and surfactants. The concentration of the active ingredient in the wettable powder is usually from about 10 percent to about 90 percent by weight based on the total weight of the wettable powder, more preferably about 25 weight percent to about 75 weight percent. In the preparation of wettable powder formulations, the active ingredients can be compounded with any finely divided solid, such as prophyllite, talc, chalk, gypsum, Fuller's earth, bentonite, attapulgite, starch, casein, gluten, montmorillonite clays, diatomaceous earths, purified silicates or the like. In such operations, the finely divided carrier and surfactants are typically blended with the compound(s) and milled.

Emulsifiable concentrates of the active ingredient comprise a concentration, such as from about 10 weight percent to about 50 weight percent of the active ingredient, in a suitable liquid, based on the total weight of the concentrate. The active ingredients are dissolved in an inert carrier, which is either a water miscible solvent or a mixture of water-immiscible organic solvents, and emulsifiers. The concentrates may be diluted with water and oil to form spray mixtures in the form of oil-in-water emulsions. Useful organic solvents include aromatics, especially the high-boiling naphthalenic and olefinic portions of petroleum such as heavy aromatic naphtha. Other organic solvents may also be used, such as, for example, terpenic solvents, including rosin derivatives, aliphatic ketones, such as cyclohexanone, and complex alcohols, such as 2-ethoxyethanol.

Emulsifiers which can be advantageously employed herein can be readily determined by those skilled in the art and include various nonionic, anionic, cationic and amphoteric emulsifiers, or a blend of two or more emulsifiers. Examples of nonionic emulsifiers useful in preparing the emulsifiable concentrates include the polyalkylene glycol ethers and condensation products of alkyl and aryl phenols, aliphatic alcohols, aliphatic amines or fatty acids with ethylene oxide, propylene oxides such as the ethoxylated alkyl phenols and carboxylic esters esterified with the polyol or polyoxyalkylene. Cationic emulsifiers include quaternary ammonium compounds and fatty amine salts. Anionic emulsifiers include the oil-soluble salts (e.g., calcium) of alkylaryl sulfonic acids, oil-soluble salts of sulfated polyglycol ethers and appropriate salts of phosphated polyglycol ether.

Representative organic liquids which can be employed in preparing emulsifiable concentrates are the aromatic liquids such as xylene, propyl benzene fractions; or mixed naphthalene fractions, mineral oils, substituted aromatic organic liquids such as dioctyl phthalate; kerosene; dialkyl amides of various fatty acids, particularly the dimethyl amides; and glycol ethers such as the n-butyl ether, ethyl ether or methyl ether of diethylene glycol, and the methyl ether of triethylene glycol and the like. Mixtures of two or more organic liquids may also be employed in the preparation of the emulsifiable concentrate. Surface-active emulsifying agents are typically employed in liquid formulations and in an amount of from 0.1 to 20 percent by weight based on the combined weight of the emulsifying agents.

Aqueous suspensions comprise suspensions of one or more water-insoluble active ingredients dispersed in an aqueous vehicle at a concentration in the range from about 5 to about 50 weight percent, e.g., about 0.1 weight percent, and intermediate ranges, based on the total weight of the aqueous suspension. Suspensions are prepared by finely grinding one or more of the active ingredients, and vigorously mixing the ground material into a vehicle comprised of water and surfactants chosen from the same types discussed above. Other components, such as inorganic salts and synthetic or natural gums, may also be added to increase the density and viscosity of the aqueous vehicle. It is often most effective to grind and mix at the same time by preparing the aqueous mixture and homogenizing it in an implement such as a sand mill, ball mill, or piston-type homogenizer.

Aqueous emulsions comprise emulsions of one or more water-insoluble active ingredients emulsified in an aqueous vehicle at a concentration typically in the range from about 5 to about 50 weight percent, based on the total weight of the aqueous emulsion. If the active ingredient is a solid it must be dissolved in a suitable water-immiscible solvent prior to the preparation of the aqueous emulsion. Emulsions are prepared by emulsifying the liquid active ingredient or water-immiscible solution thereof into an aqueous medium typically with inclusion of surfactants that aid in the formation and stabilization of the emulsion as described above. This is often accomplished with the aid of vigorous mixing provided by high shear mixers or homogenizers.

Granular formulations usually contain from about 0.5 to about 10 weight percent, based on the total weight of the granular formulation of the active ingredient(s), dispersed in an inert carrier which consists entirely or in large part of coarsely divided inert material such as attapulgite, bentonite, diatomite, clay or a similar inexpensive substance. Such formulations are usually prepared by dissolving the active ingredients in a suitable solvent and applying it to a granular carrier which has been preformed to the appropriate particle size, in the range of from about 0.5 to about 3 mm. A suitable solvent is a solvent in which the compound is substantially or completely soluble. Such formulations may also be prepared by making a dough or paste of the carrier and the compound and solvent, and crushing and drying to obtain the desired granular particle.

Dusts can be prepared by intimately mixing one or more of the active ingredients in powdered form with a suitable dusty agricultural carrier, such as, for example, kaolin clay, ground volcanic rock, and the like. Dusts can suitably contain from about 1 to about 10 weight percent of the compounds, based on the total weight of the dust.

The formulations may additionally contain adjuvant surfactants to enhance deposition, wetting and penetration of the active ingredients onto the target site such as a crop or organism. These adjuvant surfactants may optionally be employed as a component of the formulation or as a tank mix. The amount of adjuvant surfactant will typically vary from 0.01 to 1.0 percent by volume, based on a spray-volume of water, preferably 0.05 to 0.5 volume percent. Suitable adjuvant surfactants include, but are not limited to ethoxylated nonyl phenols, ethoxylated synthetic or natural alcohols, salts of the esters of sulfosuccinic acids, ethoxylated organosilicones, ethoxylated fatty amines and blends of surfactants with mineral or vegetable oils.

The formulations may optionally include combinations that contain one or more fungicides or pesticidal compounds. Pesticidal compounds may be insecticides, nematicides, miticides, arthropodicides, bactericides or combinations thereof that are compatible or synergistic with the compounds of the presently disclosed subject matter in the medium selected for application, and not antagonistic to the activity of the ritriacontene or toxic to honey bees. The tritriacontene of the presently disclosed subject matter and the pesticidal compound or fungicide in the combination can generally be present in a weight ratio of from 1:100 to 100:1.

As used herein, in relation to compositions comprising a tritriacontene, the term "an effective amount for inducing hygienic behavior in honey bees," refers to the amount of the tritriacontene necessary to induce hygienic behavior in honey bees. As used herein, in relation to compositions comprising mite-infested brood extract, the term "an effective amount for inducing hygienic behavior in honey bees," refers to the amount of the mite-infested brood extract necessary to induce hygienic behavior in honey bees.

The compositions of the presently disclosed subject matter herein may have broad ranges of uses to treat a hive or control against pests, diseases, pathogens, or infestations harmful to honey bees. The compositions of the presently disclosed subject matter herein may have broad ranges of uses as a prophylactic treatment of a hive; particularly, wherein the hygienic behavior results in inspection of the hive. In one embodiment, the prophylactic treatment is to reduce the likelihood of colony collapse disorder or severe *Varroa* mite infestation. In another embodiment, the hygienic behavior comprises eating diseased brood or diseased honey bees, removing diseased brood or diseased honey bees from hive cells, removing pests or parasites, uncapping hive cells, or uncapping and recapping hive cells. In a further embodiment, the hygienic behavior results in survival of a honey bee colony. In another embodiment, the hygienic behavior results in suppression of mite reproduction, decreased mite survival, or suppression of a mite infestation.

The exact amount of the active material to be applied can be dependent on several factors including, but not limited to, the specific active material being applied; the particular action desired; the pathogen, disease, or pest to be controlled or treated against; the stage of growth thereof the number of honey bees to be induced; the particular honey bee species; the particular honey bee breed; thresholds to avoid toxicity to the brood or hive generally; the type of formulation employed; and the method of application including, for example, dilution and rate of application and equipment employed; climate conditions. The effective amount of the tritriacontene can readily be determined by those skilled in the art. This amount will generally be from about 0.1 to about 1000 parts per million (ppm), with 1 to 500 ppm being preferred. In another embodiment, the effective amount of the tritriacontene is within the range of 1 nanogram to 1 gram per hive cell; more particularly, within the range a single tritriacontene molecule to 1 gram per hive cell. The effective amount of the mite-infested brood extract can readily be determined by those skilled in the art. This amount will generally be from about 10,000 to about $1 \times 10^{-7}$ parts per million (ppm), with $1 \times 10^{-2}$ to $1 \times 10^{-4}$ ppm being preferred.

Generally, when the compositions disclosed in this document are used in a formulation, such formulation can also contain other components. These components include, but are not limited to, (this is a non-exhaustive and non-mutually exclusive list) wetters, spreaders, stickers, penetrants, buffers, sequestering agents, drift reduction agents, compatibility agents, anti-foam agents, cleaning agents, rheology agents, stabilizers, dispersing agents and emulsifiers. A few components are described forthwith.

A wetting agent is a substance that when added to a liquid increases the spreading or penetration power of the liquid by reducing the interfacial tension between the liquid and the surface on which it is spreading. Wetting agents are used for two main functions in agrochemical formulations: during processing and manufacture to increase the rate of wetting of powders in water to make concentrates for soluble liquids or suspension concentrates; and during mixing of a product with water in a spray tank to reduce the wetting time of wettable powders and to improve the penetration of water into water-dispersible granules. Examples of wetting agents used in wettable powder, suspension concentrate, and water-dispersible granule formulations are: sodium lauryl sulphate; sodium dioctyl sulphosuccinate; alkyl phenol ethoxylates; and aliphatic alcohol ethoxylates.

A dispersing agent is a substance which adsorbs onto the surface of particles and helps to preserve the state of dispersion of the particles and prevents them from reaggregating. Dispersing agents are added to agrochemical formulations to facilitate dispersion and suspension during manufacture, and to ensure the particles redisperse into water in a spray tank. They are widely used in wettable powders, suspension concentrates and water-dispersible granules. Surfactants that are used as dispersing agents have the ability to adsorb strongly onto a particle surface and provide a charged or steric barrier to reaggregation of particles. The most commonly used surfactants are anionic, non-ionic, or mixtures of the two types. For wettable powder formulations, the most common dispersing agents are sodium lignosulphonates. For suspension concentrates, very good adsorption and stabilization are obtained using polyelectrolytes, such as sodium naphthalene sulphonate formaldehyde condensates. Tristyrylphenol ethoxylate phosphate esters are also used. Non-ionics such as alkylarylethylene oxide condensates and EO-PO block copolymers are sometimes combined with anionics as dispersing agents for suspension concentrates. In recent years, new types of very high molecular weight polymeric surfactants have been developed as dispersing agents. These have very long hydrophobic 'backbones' and a large number of ethylene oxide chains forming the 'teeth' of a 'comb' surfactant. These high molecular weight polymers can give very good long-term stability to suspension concentrates because the hydrophobic backbones have many anchoring points onto the particle surfaces. Examples of dispersing agents used in agrochemical formulations are: sodium lignosulphonates; sodium naphthalene sulphonate formaldehyde condensates; tristyrylphenol ethoxylate phosphate esters; aliphatic alcohol ethoxylates; alky ethoxylates; EO-PO block copolymers; and graft copolymers.

An emulsifying agent is a substance which stabilizes a suspension of droplets of one liquid phase in another liquid phase. Without the emulsifying agent the two liquids would separate into two immiscible liquid phases. The most commonly used emulsifier blends contain alkylphenol or aliphatic alcohol with 12 or more ethylene oxide units and the oil-soluble calcium salt of dodecylbenzene sulphonic acid. A range of hydrophile-lipophile balance ("HLB") values from 8 to 18 will normally provide good stable emulsions. Emulsion stability can sometimes be improved by the addition of a small amount of an EO-PO block copolymer surfactant.

A solubilizing agent is a surfactant which will form micelles in water at concentrations above the critical micelle concentration. The micelles are then able to dissolve or solubilize water-insoluble materials inside the hydrophobic part of the micelle. The types of surfactants usually used for solubilization are non-ionics: sorbitan monooleates; sorbitan monooleate ethoxylates; and methyl oleate esters.

Surfactants are sometimes used, either alone or with other additives such as mineral or vegetable oils as adjuvants to spray-tank mixes to improve the biological performance of the composition on the target. The types of surfactants used for bioenhancement depend generally on the nature and mode of action of the composition. However, they are often non-ionics such as: alky ethoxylates; linear aliphatic alcohol ethoxylates; aliphatic amine ethoxylates.

Organic solvents are used mainly in the formulation of emulsifiable concentrates, ULV formulations, and to a lesser extent granular formulations. Sometimes mixtures of solvents are used. The first main groups of solvents are aliphatic paraffinic oils such as kerosene or refined paraffins. The second main group and the most common comprises the aromatic solvents such as xylene and higher molecular weight fractions of C9 and C10 aromatic solvents. Chlorinated hydrocarbons are useful as cosolvents to prevent crystallization of the compositions when the formulation is emulsified into water. Alcohols are sometimes used as cosolvents to increase solvent power.

Thickeners or gelling agents are used mainly in the formulation of suspension concentrates, emulsions and suspoemulsions to modify the rheology or flow properties of the liquid and to prevent separation and settling of the dispersed particles or droplets. Thickening, gelling, and anti-settling agents generally fall into two categories, namely water-insoluble particulates and water-soluble polymers. It is possible to produce suspension concentrate formulations using clays and silicas. Examples of these types of materials, include, but are limited to, montmorillonite, e.g. bentonite; magnesium aluminum silicate; and attapulgite. Water-soluble polysaccharides have been used as thickening-gelling agents for many years. The types of polysaccharides most commonly used are natural extracts of seeds and seaweeds are synthetic derivatives of cellulose. Examples of these types of materials include, but are not limited to, guar gum; locust bean gum; carrageenam; alginates; methyl cellulose; sodium carboxymethyl cellulose (SCMC); hydroxyethyl cellulose (HEC). Other types of anti-settling agents are based on modified starches, polyacrylates, polyvinyl alcohol and polyethylene oxide. Another good anti-settling agent is xanthan gum.

Microorganisms cause spoilage of formulated products. Therefore preservation agents are used to eliminate or reduce their effect. Examples of such agents include, but are not limited to: propionic acid and its sodium salt; sorbic acid and its sodium or potassium salts; benzoic acid and its sodium salt; p-hydroxy benzoic acid sodium salt; methyl p-hydroxy benzoate; and 1,2-benzisothiazalin-3-one (BIT).

The presence of surfactants, which lower interfacial tension, often causes water-based formulations to foam during mixing operations in production and in application through a spray tank. In order to reduce the tendency to foam, anti-foam agents are often added either during the production stage or before filling into bottles. Generally, there are two types of anti-foam agents, namely silicones and non-silicones. Silicones are usually aqueous emulsions of dimethyl polysiloxane while the non-silicone anti-foam agents are water-insoluble oils, such as octanol and nonanol, or silica. In both cases, the function of the anti-foam agent is to displace the surfactant from the air-water interface.

"Green" agents (e.g., adjuvants, surfactants, solvents) can reduce the overall environmental footprint of crop protection formulations. Green agents are biodegradable and generally derived from natural and/or sustainable sources, e.g. plant and animal sources. Specific examples are: vegetable oils, seed oils, and esters thereof, also alkoxylated alkyl polyglucosides.

For further information see "CHEMISTRY AND TECHNOLOGY OF AGROCHEMICAL FORMULATIONS" edited by D. A. Knowles, copyright 1998 by Kluwer Academic Publishers.

II. Methods for Inducing Hygienic Behavior

In other embodiments, the presently disclosed subject matter is directed to a method of inducing hygienic behavior in honey bees, the method comprising contacting hive cells with a composition comprising a tritriacontene and an agriculturally acceptable diluent or carrier, wherein the tritriacontene is in an effective amount for inducing hygienic behavior in honey bees. In other embodiments, the presently disclosed subject matter is directed to a method of inducing hygienic behavior in honey bees, the method comprising contacting hive cells with a composition comprising a mite-infested brood extract and an agriculturally acceptable diluent or carrier, wherein the mite-infested brood extract is in an effective amount for inducing hygienic behavior in honey bees. In further embodiments, the composition, the tritriacontene, the mite-infested brood extract, the agriculturally acceptable diluent or carrier, the effective amount for inducing hygienic behavior in honey bees, and other terms may be as described herein. The methods of the presently disclosed subject matter may have broad ranges of uses to treat a hive or control against pests, diseases, pathogens, or infestations harmful to honey bees. In another embodiment, the hygienic behavior results in suppression of mite reproduction, decreased mite survival, or suppression of a mite infestation. In another embodiment, the hygienic behavior results in survival of a honey bee colony. In another embodiment, the hive cells are capped hive cells or uncapped hive cells. In another embodiment, the hive cells are worker-brood cells, drone-brood cells, or queen bee cells. In a further embodiment, the honey bees are of the species *Apis mellifera* or *Apis cerana*.

As social insects, honey bees complement individual immunity with mechanisms of social immunity for defense against pathogens and parasites. Honey bees are able to reduce parasite and pathogen loads through age-specific sanitary activities such as hygienic behavior. The complete mechanism for hygienic behavior is not completely understood, but can be measured, for instance, by frequency of certain behaviors in honey bees, such as eating diseased brood or diseased honey bees, removing diseased brood or diseased honey bees from hive cells, removing pests or parasites, uncapping hive cells, or uncapping and recapping hive cells. See for example. [8, 9, 11] Hygienic behavior has been described by some as the detection, uncapping and/or removal of diseased brood from the hive. [182] As used herein, the term "hygienic behavior" includes those described herein and known in the art; for example, without limiting the foregoing, as described in Spivak, M., (1996) Honey bee hygienic behavior and defense against *Varroa jacobsoni*. Apidologie 27: 245-260.

In one embodiment, the hygienic behavior comprises eating diseased brood or diseased honey bees, removing diseased brood or diseased honey bees from hive cells, removing pests or parasites, uncapping hive cells, or uncapping and recapping hive cells. In another embodiment, the hygienic behavior comprises uncapping a hive cell, removing pests or parasites, and recapping the hive cell. In a further embodiment, the diseased brood or diseased honey bees are infested with a pest or parasite; infected with a pathogen; or damaged. In yet another embodiment the diseased brood are eggs, larvae, or pupae.

In a further embodiment, the pests or parasites are mites, wax moth, small hive beetle, or *Nosema*. In a further embodiment, the mites are mites of the genus *Varroa*; particularly wherein the mites are mites of the species *Varroa destructor* or *Varroa jacobsoni*. In a further embodiment, the mites are mites of the genus *Acarapis*; particularly wherein the mites are mites of the species *Acarapis woodi* (also known as tracheal mite). In another embodiment, the mites are mites of the genus *Tropilaelaps*.

*Varroa destrutctor* is an obligate, ectoparasitic honey bee mite, arguably the most important threat to honey bee health and apiculture today. [31-32] During their reproductive stage, female foundress mites enter honey brood cells just before capping and bury themselves in the brood food at the base of the cell. After about six hours when the food has been consumed by the bee brood, the mite emerges and establishes a feeding site on the brood, from which it sucks hemolymph. [198] Approximately 70 hours after cell capping the foundress mite begins to lay eggs, the first of which is haploid and develops into a male. Diploid eggs are then laid at approximately 30-hour intervals. These develop into females which mate with the waiting male such that by the end of honey bee development up to four (worker cell) or five (drone cell) fertilized female *Varroa* may emerge with the emerging honey bee to repeat the cycle. [31] *Varroa* act as a physical burden to the bee, reducing body weight and protein levels primarily through the sucking of hemolymph. [44, 199, 200, 201, 202]

While the physical burden of *Varroa* is problematic to honey bee health, it is merely one of many honey bee threats associated with *Varroa*. *Varroa* transmit diseases to honey bees [60, 135, 159, 161] and have been associated with both viral amplification and honey bee disease susceptibility. [51, 60] *Varroa* mites enter honey bee colonies as adults, presumably with returning foragers or drifting workers from other colonies. Inside the nest, the mature, fertilized *Varroa* females enter a brood cell that contains a worker or drone larvae that is about to be closed with a wax cap. After the cell is sealed, the mite emerges from hiding and establishes a feeding site that it will share with its offspring. [35] While the host is undergoing its final molt from the $5^{th}$ larval instar to pupae, the *Varroa* foundress initiates egg-laying, first producing an unfertilized male egg and then subsequently fertilized female eggs every 30 hours. These offspring develop and sib-mate before leaving the cell when the adult honey bee opens the wax capping to emerge. [36, 37]

*Varroa* mites only reproduce on drone brood in *A. cerana* honey bee hosts but are able to utilize worker and drone brood to complete their life cycle in *A. mellifera* honey bees. This difference in host utilization is presumably due to longer development and less hygienic behavior of *A. mellifera* honey bees. [38, 39] *Varroa* directly impairs colony function in *A. mellifera* honey bees, while only curtailing the drone production of *A. cerana* honey bees. Moreover, the persistent worker brood production allows for the build-up of higher *Varroa* population densities in *A. mellifera* colonies. [40]

Varroatosis is caused by the mite parasitizing honey bees, e.g. drones and queen bees, larvae and pupae. Although *Varroa* causes physical and physiological damage when feeding on the honey bee hemolymph [44], its most serious impact on honey bee health is caused by enabling viral diseases. [45] Varroatosis produces great damage in apiculture due to the acute debilitation and high mortality of the members of the honey bee colony. Also, *Varroa* is an effective vector of viruses [30, 31] and possibly other microorgansms. [43] *V. destructor* increases the virulence of viruses [46] and may lead to fatal outbreaks. [47, 48] Specifically, more virulent, strains of viruses are selectively favored. [49] *Varroa* feeding may also activate latent viruses. [31, 50]

Small hive beetle reproduces in a hive and is a damaging pest of beeswax combs, comb honey and bee-collected pollen. The females will lay egg masses in protected crevasses in the hive. The larva feed on the honey and pollen. If the infestation is severe enough the bees will abandon the hive. As the beetles move about the hive they defecate forming a slimy mess that results in the honey fermenting.

Wax moth larvae are very destructive and can quickly destroy stored beeswax combs. They tunnel and chew through combs, particularly combs that have contained brood and pollen. Developing honey bee pupae are exposed when wax moth larvae partly remove the cell caps, a condition known as bald brood. Worker bees chew the remainder of the capping thereby fully exposing the heads of the pupae that continue to develop normally. The lines of bald brood follow the direction of the wax moth's travel. Some honey bee pupae nearing maturity may have deformed legs or wings. One of the causes of this deformity is a result of wax moth excreta affecting the final molt of the pupa before its emergence from the cell.

*Nosema* is a parasitic protozoa, caused by the microsporidian *Nosema apis* or *Nosema ceranae* that resides in the gut of the bee. The parasites damage the hosts by destroying internal organs. Inside the cell of the bee's gut, *Nosema* reproduces by forming spores, which are passed within the bee's waste. Bees will begin to expel waste in the hive and on the outside; and can cause rapid colony decline.

In another embodiment, the pathogen is a bacterium, fungus, or virus. In one embodiment the pathogen is *Ascosphaera apis*; particularly wherein *Ascosphaera apis* causes chalkbrood. In one embodiment, the pathogen is *Aspergillus fumigatus, Aspergillus flavus*, or *Aspergillus niger*; more particularly wherein *Aspergillus fumigatus, Aspergillus flavus*, or *Aspergillus niger* causes stonebrood. In one embodiment, the bacterium is *Paenibacillus* larvae (formerly classified as *Bacillus* larvae and *Paenibacillus* larvae ssp larvae/pulvifaciens); more particularly wherein *Paenibacillus* larvae causes American foulbrood. In one embodiment, the bacterium is *Melissococcus plutonius*; more particularly wherein *Melissococcus plutonius* causes European foulbrood. In one embodiment, the virus is of the family of cripaviridae viruses; more particularly, wherein the virus is chronic paralysis virus. In one embodiment, the virus is of the family of dicistroviridae viruses; more particularly, wherein the virus is acute bee paralysis virus, Israeli acute paralysis virus, Kashmir bee virus, or Black queen cell virus. In one embodiment, the virus is Cloudy wing virus, Sacbrood virus, or *Perina nuda*. In another embodiment, the virus is *Morator aetatulas*; more particularly, wherein *Morator aetatulas* causes sacbrood disease. In one embodiment, the virus is of the family flaviridae; more particularly, wherein the virus is Deformed wing virus. In one embodiment, the virus is of the family Iridovzridae; more particularly, wherein the virus is invertebrate iridescent virus type 6 (IIV-6). In one embodiment, the virus is of the family Secoviridae; more particularly, wherein the virus is tobacco ringspot virus. In one embodiment, the virus is slow paralysis virus.

Deformed wing virus (DWV), Kashmir bee virus (KBV), sacbrood virus (SBV), acute bee paralysis virus (ABPV), slow paralysis virus (SPV), and Israeli acute paralysis virus (IAPV) have been associated with *Varroa*. [42, 57, 58] Many of these viruses have presumably alternative modes of transmission [59] but the effective horizontal transmission by the *Varroa* vector has profound implications for the viruses that are found in the honey bee hosts. [60]

Chalkbrood is a disease caused by the fungus *Ascosphaera apis* that turns the body of an infected bee larva into fungal cells which eventually produce millions of spores. Infected larvae become overgrown with a white cotton-like mycelium and eventually dry to a hard, white or gray shrunken mass (thus the name Chalkbrood) referred to as a mummy. The fruit-bodies of the fungus develop on the gray-colored mummies, and the spores released from the spore capsules can enter the air of the beehive. The disease is spread through local populations by adult bees emerging from contaminated media. It has been shown that a single adult bee may carry from 50 to 300 million spores on its body surface after having chewed through a single diseased cadaver as it extracts itself from the cell or nesting material. Once the disease becomes established in an area it increases rapidly because of the reuse of contaminated nesting media in successive years. As a result of infection, the colonies fail to grow to a sufficiently large size, their resistance becomes impaired and their honey-producing capacity decreases to a degree depending on the severity of the mycotic infection. Over the past several years various control measures have been developed but none have been completely effective or economically practical. Sterilization of nesting media has been attempted by use of dry chlorine or bleach, convection heat, and microwave exposure. Also, surface sterilization of adult bees consisting of a bee bath in sodium hypochlorite or iodine has been employed. Dusting with general antibiotics and fungicides in such a manner that they are ingested by the adult bee also has met with little success. A related infection, Stonebrood disease (forming stone-hard larvae) is caused by the fungus *Aspergillus flavus* and related species.

American foulbrood is caused by the bacterium *Paenibacullus* larvae, which can remain viable indefinitely on beekeeping equipment. It infects the gut of worker, drone and queen larvae and, while it may not destroy a colony in the first year, if left unchecked may ultimately lead to the death of the colony. The main method of treatment is with the antibiotic oxytetracycline, administered in various forms with a sugar carrier. However, there are many problems associated with administration of oxytetracycline, including problems related to stability, antibiotic contamination of the honey, the possibility of killing open brood on the face of brood combs, and unevenness of dosing.

European Foulbrood disease is caused by the bacterium *Melissococcus pluton*, which is fed to the worker, drone and queen larvae by nurse bees. Diseased colonies fail to increase normally so that no surplus honey, in excess of that needed by the colony to survive, is available for the beekeeper. Oxytetracycline is also used for treating such diseased colonies.

"Damaged" refers to physically damaged, physiologically damaged, health-compromised, and/or immune system-compromised, or dead. The foregoing types of damage can be the result of, without limiting the foregoing, a parasite, pest, pathogen, environmental change-related stresses, malnutrition, or exposure to contaminated food (e.g. for example to pesticide laden pollen), pesticides (e.g. neonicotinoids such as imidacloprid, clothianidin, and thiamethoxam; neonicotinamides; carbamates), insecticides (e.g. organophosphates), ftimungicides, miticides (e.g. acaricides, such as coumaphos, tau-fluvalinate, flumethrin, and anitraz), or other toxic chemicals.

For example, without limiting the foregoing, honey bees with Varroatosis or dysentery are damaged. For example, without limiting the foregoing, chilled brood or bald brood are damaged. Removal rates that correspond to the level of brood health support the existence of the evolution of a damage-dependent hygienic response. [93, 156] Damage-dependent hygiene is also supported by evidence that immune response affects honey bee cuticular chemicals. [112] Existence of a damage-dependent response to *Varroa* has recently been supported by evidence of mite-virulence dependent hygienic removal. [179]

Miticides used to control *Varroa* infestations, such as fluvalinate and coumaphos, have been found to have lethal and sublethal effects on honey bee queens, workers, and drones. [2, 66, 132, 154, 162, 177, 181] For example, moderate doses of fluvalinate in the hive have been associated with reduced queen weight [68] and reduced drone weight and number of spermatozoa. [203] Even low doses of coumaphos have been associated with increased queen mortality, physical deformities, reduced body and ovary weight, and atypical behavior [68, 133, 177] and moderate coumaphos exposure has been linked to reduction of drone sperm vitality. [204] Synergistic effects of fluvalinate and coumaphos have been measured, where the toxicity of each chemical is significantly increased in bees previously exposed to the other. [172] The lipophilic nature of both the synthetic pyrethroid fluvalinate and the organophosphate coumaphos leads to high absorption and accumulation of the chemicals in hives, especially in wax, meaning that exposure of bees to these and similar compounds increases with time and number of chemical treatments. A 2007 study of residues in honey bee hives found 46 pesticides in 108 pollen samples, and 20 pesticides in 88 wax samples, with over 55% of pollen and 100% of wax samples containing the most concentrated pesticides: the miticides fluvalinate and coumaphos. [62] Furthermore, immunosuppression caused by chemical exposure makes honey bees more susceptible to parasites like *Varroa*, as well as to the pathogens they vector. [64, 70, 181, 184]

In another embodiment, the hygienic behavior comprises uncapping hive cells of healthy brood or diseased brood; more particularly, wherein the hygienic behavior further comprises recapping the hive cells of healthy brood; particularly, wherein the hygienic behavior further comprises removing diseased brood or pests or parasites; particularly, wherein the hygienic behavior further comprises removing diseased brood or pests or parasites, and recapping the hive cells. The methods of the presently disclosed subject matter herein may have broad ranges of uses as a prophylactic treatment of a hive; particularly, wherein the hygienic behavior results in inspection of the hive. For example, without limiting the foregoing, nurse bees will remove *Varroa*-infested brood but simply recap healthy brood. [96] In one embodiment, the prophylactic treatment is to reduce the likelihood of colony collapse disorder or severe *Varroa* mite infestation.

In another embodiment, contacting hive cells with a composition comprises spraying, dusting, dipping, spotting, or fumigating. In another embodiment, the contacting of the hive cells is on one or more days after the hive cells are capped. In another embodiment, the contacting of the hive cells is on one or more days before the hive cells are capped. The hive cells may be artificial or natural compartments. The hive cells may be part of combs that are natural or artificial (including combs made of wax, resin, plastic, metal, wax-coated plastic). The hive cells are not necessarily part of a hive.

III. Methods for Selecting Bees Exhibiting Hygienic Behavior

Current methods for selectively breeding bees for hygienic behavior result in bees that have varying degrees of sensitivity to diseased broods. Reasons for lack of efficacy include non mite-specificity of selection processes. [92, 95, 183] For example, the olfactory trigger for hygienic removal of mite-infested and other live brood may be significantly lower than that of dead brood. [156, 100, 183] As a result, the threshold for olfactory response needs to be lower for mite-removal than it does for removal of freeze-killed brood or brood infected with more virulent honey bee diseases such as Chalkbrood or American Foulbrood (caused by the fungus *Ascosphaera apis* and the bacterium *Paenibacullus larvae*, respectively). Also, existence of the evolution of a damage-dependent hygienic response is supported by removal rates that correspond to the level of brood health. [156, 93]

The presently disclosed subject matter provides methods for selecting bees exhibiting hygienic behavior as described more fully below and relates to findings that a tritriacontene compound triggers hygienic behavior in honey bees, and mite-infested brood extract triggers hygienic behavior in honey bees.

In additional embodiments, the presently disclosed subject matter is directed to a method for selecting one or more honey bee(s) exhibiting hygienic behavior comprising a) applying a tritriacontene composition to a set of hive cells; b) performing an assay to identify a hygienic colony, wherein the assay comprises exposing the set of hive cells to a test colony; and c) selecting one or more honey bee(s) from an identified hygienic colony, wherein the selected one or more honey bee(s) exhibit hygienic behavior.

In additional embodiments, the presently disclosed subject matter is directed to a method for selecting one or more honey bee(s) exhibiting hygienic behavior comprising a) applying a mite-infested brood extract composition to a set of hive cells; b) performing an assay to identify a hygienic colony, wherein the assay comprises exposing the set of hive cells to a test colony; and c) selecting one or more honey bee(s) from an identified hygienic colony, wherein the selected one or more honey bee(s) exhibit hygienic behavior.

In further embodiments, the set of hive cells contains a diseased brood, diseased honey bees, or pests or parasites. In another embodiment, the identified hygienic colony comprises honey bees exhibiting hygienic behavior; more particularly wherein the hygienic behavior comprises eating diseased brood or diseased honey bees, removing diseased brood or diseased honey bees from hive cells, removing pests or parasites, uncapping hive cells, or uncapping and recapping hive cells.

In one embodiment, each of the selected honey bee(s) is a queen bee or drone bee. In further embodiments, the tritriacontene composition, the mite-infested brood extract, the diseased brood or diseased honey bees, pests or parasites, and other terms may be as described herein. In another embodiment, applying the tritriacontene composition or the mite-infested brood extract comprises spraying, dusting, dipping, spotting, or fumigating. In another embodiment, the hive cells are worker-brood cells, drone-brood cells, or queen bee cells.

In another embodiment, the assay further comprises i) determining the amount of emptied hive cells in the set of hive cells; and ii) identifying a hygienic colony, wherein a test colony is a hygienic colony if at least 85% of the set of hive cells are emptied; more particularly, wherein a test colony is a hygienic colony if at least 90% of the set of hive cells are emptied; more particularly, wherein a test colony is a hygienic colony if at least 95% of the set of hive cells are emptied. In another embodiment, the emptied hive cells have no eggs, larvae, or pupae, or contain partially eaten larvae or pupae. In another embodiment, the emptied hive cells have no diseased honey bees, or contain partially eaten diseased honey bees. In another embodiment, the emptied hive cells have no pests or parasites, or contain eaten pests or parasites. In another embodiment, the emptied hive cells are capped hive cells or uncapped hive cells.

In another embodiment, the hive cells are capped hive cells and the assay further comprises i) determining the amount of uncapped and/or recapped hive cells in the set of capped hive cells; and ii) identifying a hygienic colony, wherein a test colony is a hygienic colony if at least 85% of the set of capped hive cells are uncapped and/or recapped; more particularly, wherein a test colony is a hygienic colony if at least 90% of the set of capped hive cells are uncapped and/or recapped; more particularly, wherein a test colony is a hygienic colony if at least 95% of the set of capped hive cells are uncapped and/or recapped. In a further embodiment, the capped hive cells are empty.

In another embodiment, the method further comprises d) mating a selected honey bee with one or more honey bee(s) from at least one separately identified hygienic colony to produce offspring; more particularly wherein at least one separately identified hygienic colony was bred according to the same method; or more particularly wherein at least one separately identified hygienic colony was bred or identified by a method based on freeze-killed brood, suppression of mite reproduction, or removal of damaged brood. In another embodiment, a queen bee is selected and mated: (a) naturally with one or more drones from at least one separately identified hygienic colony; or (b) artificially inseminated with semen from one or more drones from at least one separately identified hygienic colony.

The bees may be mated in a manner known in the art; for example, without limiting the foregoing, by means of conventional breeding processes (e.g. open mating in drone congregation areas of breeds of specifically enriched traits) and mating equipment (e.g. artificial insemination devices).

In another embodiment, the method further comprises e) raising the offspring, f) applying a tritriacontene composition to a second set of hive cells, g) performing a second assay to identify whether the raised offspring is a hygienic colony, wherein the second assay comprises exposing the second set of hive cells to the raised offspring, and h) selecting one or more honey bee(s) from an identified hygienic colony, wherein the selected one or more honey bee(s) exhibit hygienic behavior.

In another embodiment, the method further comprises e) raising the offspring, f) applying a mite-infested brood extract composition to a second set of hive cells, g) performing a second assay to identify whether the raised offspring is a hygienic colony, wherein the second assay comprises exposing the second set of hive cells to the raised offspring, and h) selecting one or more honey bee(s) from an identified hygienic colony, wherein the selected one or more honey bee(s) exhibit hygienic behavior.

The offspring may be raised in a manner known in the art; for example, without limiting the foregoing, by means of conventional processes of queen rearing and drone rearing to propagate the trait.

In further embodiments, the second set of hive cells contains a diseased brood, diseased honey bees, or pests or parasites. In another embodiment, the identified hygienic colony comprises honey bees exhibiting hygienic behavior; more particularly wherein the hygienic behavior comprises eating diseased brood or diseased honey bees, removing diseased brood or diseased honey bees from hive cells, removing pests or parasites, uncapping hive cells, or uncapping and recapping hive cells. In further embodiments, the pests or parasites, the diseased brood, the diseased honey bees, and other terms may be as described herein.

In another embodiment, the second assay further comprises i) determining the amount of emptied hive cells in the second set of hive cells; and ii) identifying a hygienic colony, wherein the raised offspring is a hygienic colony if at least 85% of the second set of hive cells are emptied; more particularly, wherein the raised offspring is a hygienic colony if at least 90% of the second set of hive cells are emptied; more particularly, wherein the raised offspring is a hygienic colony if at least 95% of the second set of hive cells are emptied. In another embodiment, the emptied hive cells have no eggs, larvae, or pupae, or contain partially eaten larvae or pupae. In another embodiment, the emptied hive cells have no diseased honey bees, or contain partially eaten diseased honey bees. In another embodiment, the emptied hive cells have no pests or parasites, or contain eaten pests or parasites. In another embodiment, the emptied hive cells are capped hive cells or uncapped hive cells.

In another embodiment, the hive cells are capped hive cells and the second assay further comprises i) determining the amount of uncapped and/or recapped hive cells in the second set of capped hive cells; and ii) identifying a hygienic colony, wherein the raised offspring is a hygienic colony if at least 85% of the second set of capped hive cells are uncapped and/or recapped; more particularly, wherein the raised offspring is a hygienic colony if at least 90% of the second set of capped hive cells are uncapped and/or recapped; more particularly, wherein the raised offspring is a hygienic colony if at least 95% of the second set of capped hive cells are uncapped and/or recapped. In a further embodiment, the capped hive cells are empty, The assay and the second assay each independently may comprise steps known in the art for selective breeding of hygienic behavior, including those for augmenting hive resistance to *Varroa*. [75, 87, 92, 155, 183] For example, HYG breeds are selected for based on the removal of freeze-killed brood. In some embodiments, the assay and the second assay each independently may further comprise i)

freeze-killing a portion of a brood, ii) determining the amount of hive cells uncapped and containing no diseased brood; and iii) identifying a hygienic colony, wherein a test colony is a hygienic colony if at least 85% of the set of hive cells are uncapped and containing no diseased brood; more particularly, wherein a test colony is a hygienic colony if at least 90% of the set of hive cells are uncapped and containing no diseased brood; more particularly, wherein a test colony is a hygienic colony if at least 95% of the set of hive cells are uncapped and containing no diseased brood. In another embodiment, VSH breeds are selected for based on apparent suppression of mite reproduction. In some embodiments, the set of hive cells contains diseased brood infested with mites of the species *Varroa destructor*, and the assay and the second assay each independently may further comprises i) determining the amount of hive cells containing no diseased brood; and ii) identifying a hygienic colony, wherein a test colony is a hygienic colony if at least 85% of the set of hive cells contain no diseased brood; more particularly, wherein, a test colony is a hygienic colony if at least 90% of the set of hive cells contain no diseased brood; more particularly, wherein, a test colony is a hygienic colony if at least 95% of the set of hive cells contain no diseased brood.

In some embodiments, the identified hygienic colony as presently disclosed in the subject matter herein may have broad ranges of uses to treat a hive or control against pests, diseases, pathogens, or infestations harmful to honey bees. In some embodiments, the identified hygienic colony as presently disclosed in the subject matter herein may have broad ranges of uses as a prophylactic treatment of a hive; particularly, wherein the hygienic behavior results in inspection of the hive. In one embodiment, the prophylactic treatment is to reduce the likelihood of colony collapse disorder or severe *Varroa* mite infestation.

In some embodiments, the identified hygienic colony as presently disclosed in the subject matter herein may have broad ranges of uses to produce, for example, honey, nectar, beeswax, pollen, or propolis. In some embodiments, the identified hygienic colony as presently disclosed in the subject matter herein may have broad ranges of uses to pollinate plants and crops, for example without limiting the foregoing, insect-pollinated plants and crops; more particularly fruits, vegetables, or nuts. Non-limiting examples of plants and crops include acerola, adzuki bean, allspice, almond, almonds, apricot, apple, avocado, azarole, beet, black currant, blackberry, blueberry, boysenberry, broccoli, Brussels sprouts, buckwheat, cabbage, cantaloupe, caraway, cardamom, carrot, cashew, cauliflower, celery, chestnut, citrus tree, clover, coconut, coffee, coriander, cotton, crown-vetch, cucumber, elderberry, feijoa, fennel, flax, grape, green bean, guar bean, guava, haricot bean, hyacinth bean, jujube, kidney bean, kiwifruit, lemon, lima bean, lime, longan, loquat, lupine, lychee, macadamia, mango, melon, *mungo* bean, mustard, nectarine, okra, onion, papay a, peach, pear, pear, peas, peppers, persimmon, plum, pomegranate, quince, rambutan, rapeseed, raspberry, red currant, rose hips, rowanberry, safflower, sainfoin, scarlet runner bean, service tree, sesame, sour cherry, squash, starfruit, strawberry tree, strawberry, string bean, sunflower, sweet cherry, tamarind, tangelo, tomato, turnip, or watermelon.

IV. Assays

In some embodiments, the presently disclosed subject matter is directed to a method for assessing the degree of hygienic behavior within a honey bee colony comprising a) applying a tritriacontene composition to a set of hive cells; b) exposing the set of hive cells to a honey bee colony; and c) determining the amount of emptied hive cells in the set of hive cells; wherein a higher amount of the set of hive cells that are emptied is associated with a greater degree of hygienic behavior. In further embodiments, the set of hive cells contains a diseased brood, diseased honey bees, or pests or parasites. In another embodiment, the emptied hive cells are capped hive cells or uncapped hive cells.

In some embodiments, the presently disclosed subject matter is directed to a method for assessing the degree of hygienic behavior within a honey bee colony comprising a) applying a mite-infested brood extract composition to a set of hive cells; b) exposing the set of hive cells to a honey bee colony; and c) determining the amount of emptied hive cells in the set of hive cells; wherein a higher amount of the set of hive cells that are emptied is associated with a greater degree of hygienic behavior. In further embodiments, the set of hive cells contains a diseased brood, diseased honey bees, or pests or parasites. In another embodiment, the emptied hive cells are capped hive cells or uncapped hive cells.

In other embodiments, the presently disclosed subject matter is directed to a method for assessing the degree of hygienic behavior within a honey bee colony comprising a) applying a tritriacontene composition to a set of capped hive cells; b) exposing the set of capped hive cells to a honey bee colony; and c) determining the amount of uncapped and/or recapped hive cells in the set of capped hive cells; wherein a higher amount of the set of hive cells that are uncapped and/or recapped is associated with a greater degree of hygienic behavior. In further embodiments, the set of capped hive cells contains a diseased brood, diseased honey bees, or pests or parasites. In another embodiment, the set of capped hive cells is empty.

In other embodiments, the presently disclosed subject matter is directed to a method for assessing the degree of hygienic behavior within a honey bee colony comprising a) applying a mite-infested brood extract composition to a set of capped hive cells; b) exposing the set of capped hive cells to a honey bee colony; and c) determining the amount of uncapped and/or recapped hive cells in the set of capped hive cells; wherein a higher amount of the set of hive cells that are uncapped and/or recapped is associated with a greater degree of hygienic behavior. In further embodiments, the set of capped hive cells contains a diseased brood, diseased honey bees, or pests or parasites. In another embodiment, the set of capped hive cells is empty.

In further embodiments, the tritriacontene composition, the mite-infested brood extract composition, the diseased brood or diseased honey bees, pests or parasites, hive cells, emptied hive cells, hygienic behavior, and other terms may be as described herein.

V. EXAMPLES

1. Behavioral Study
Methods
Overview

Over two consecutive summers, sections of honey bee frames containing eggs from queens of various breeds, representing various levels of hygienic behavior, were grafted together. Grafted frames were placed into novel hives for rearing (such that no egg went back into its hive of origin). *Varroa* mite, wound and control treatments were applied. Removal status of each brood cell over a one week period was recorded. This experimental setup allowed comparison of removal 1) between brood types within each hive type, and 2) for each brood type across hive types.

Materials

Wooden frames, wax foundation, and unselected control (CON) queens were purchased from Triad Bee Supply in Trinity, N.C. Minnesota Hygienic (HYG) queens were donated by Jeff Hull and Amy Weeks in West Monroe, La. *Varroa* Sensitive Hygienic (VSH) queens were donated by the United States Department of Agriculture's Agricultural Research Center (USDA-ARC) in Baton Rouge, La. All queens were open mated and studied for one bee season only. Sample sizes for hives of CON, HYG and VSH origin were 2, 4 and 3, respectively for 2013, and 2, 2 and 2, respectively for 2014. Directly following the behavioral experiments, freeze-killed brood (FKB) assays were performed to determine the level of hygienic behavior exhibited by each hive. [100] However, due to missing queens and/or insufficient brood frames, successful results were only obtained for 11 of the 15 hives tested.

Methods

All behavioral assays were conducted at the University of North Carolina at Greensboro bee-yard during the summers of 2013 and 2014. Each year, medium wooden frames were sawed vertically into equal thirds and reassembled using metal brackets or staples. Reassembled frames were fitted with new wax foundation containing steel vertical wire stabilizers. Frames were placed into the top box of unselected CON hives, above queen excluders, so that the comb could be drawn out but the queen could not lay eggs in the cells.

Once combs were drawn out, frames were removed from unselected hives and fitted with wire cages constructed using mesh size 0.5 cm×0.5 cm, such that workers could move freely on and off both sides of each frame but queens, once introduced, could not leave. Single queens of unselected control (CON), Minnesota Hygienic (HYG), and *Varroa*-Sensitive Hygienic (VSH) breeds were placed on each frame. Caged experimental frames were returned to each queen's respective hive. Once eggs were present on >75% of both sides of a frame, frames were removed from their hives. A razor blade was used to cut combs into thirds (corresponding to the previous frame cuts) and metal brackets and staples were removed. Sections from different frames were then grafted together using metal brackets and staples such that each new frame contained eggs from different queens of VSH, HYG or CON origin. Frames were then redistributed into new hives, such that no brood was ever placed back into its hive of origin.

After allowing 5-7 days for development, the location of uncapped cells containing $5^{th}$ larval instars were marked using a permanent marker and transparent plastic sheet secured over each frame with thumb tacks. Cells along wires were avoided since wires are associated with increased brood removal rates. Frames were returned to their hives for 12 to 16 hours and then checked to ensure that they had been sealed with a wax cap for the initiation of pupation. This procedure ensured that treatments were administered to capped cells within 18 hours of capping, as is necessary to ensure initiation of mite oogenesis. [165] Mite, wound and control treatments were administered to recently capped cells in each section of frame corresponding to a different breed. To open the caps of experimental cells, one side of the cap was cut with the edge of a razor blade. The cell cap could then be lifted up, and resealed after treatment administration by pressing the cell cap against the cell wall with the edge of the razor. The treatments assigned to each cell were selected at random, and each cell received either one mite, one wound, or the control treatment. Mites were collected from non-experimental colonies at the UNCG bee-yard using the sugar shake method. [105, 187] Mites were shaken on to a damp paper towel, and were gently rinsed with a drop of clean water before being introduced to cells using a fine-tipped paintbrush within approximately one hour of collection. Mites that could not clutch the paintbrush bristles were considered to be unhealthy, and were not used. Wounds were inflicted using 50 µm diameter capillary needles on the dorsal side of the brood between the first abdominal segment and the second thoracic segment according to existing protocols that mimic *Varroa* mite feeding [186, 35] Control cells were opened and resealed just as mite and wound cells, but received neither mite nor wound treatment. In 2013, a total of 1,063 cells were included in the study (349 VSH, 462 HYG, and 252 CON), and in 2014, an additional 1,025 cells were included (320 VSH, 354 HYG, 351 CON).

Each day for one week following treatment administration, experimental frames were removed from their hives for no more than 30 minutes per day to allow monitoring of each experimental cell for uncapping and removal. Brood removed on the first day following treatment introductions was excluded to avoid experimental artifacts, such as removal triggered by poorly resealed cells.

Statistical Analysis

A full factorial logistic regression model was used to determine the effects of brood type, hive type, treatment and year on brood removal. This analysis revealed higher order interactions (see results) that made the full data set difficult to interpret. Thus, the data set was split and Chi-square tests were used to determine the effect of brood type on removal (the focus of our hypothesis) for each treatment by hive type by year combination. Bonferroni correction was used for pairwise comparisons to control the family-wise error rate within each treatment by hive type by year combination (using a corrected significance threshold of p≤0.0167). Overall effects of brood type, hive type and treatment were assessed independently of each other using separate Chi-square analyses for each year. For the 11 hives with FKB assay data, Pearson product-moment correlation coefficients were computed to assess the relationships between 1) average percentage removal of brood in relation to the level of hygiene of the brood's hive of origin (overall and for each treatment type: mite, wound, or control), and 2) average percentage removal of brood in relation to the level of hygiene of its host hive (overall and for each treatment type: mite, wound, or control). All statistical analyses were performed using IBM SPSS Statistics, Version 22.

Results

Effects of Brood Type, Hive Type and Treatment on Removal Rates

The full logistic regression model, including the effects of brood type, hive type, treatment, year and all interactions on brood removal, was statistically significant ($\chi^2$=328.1, df=53, p<0.001). The model achieved a correct classification of brood removal in 83.3% of the cases with an associated Nagelkerke's $R^2$ of 0.24. Multiple factors and interactions were statistically significant. (Table 1).

TABLE 1

Statistically significant factors and interactions from a full factorial logistic regression model on hive type, brood type, treatment and year.

| Factor | Wald | d.f. | Sig. | EXP (B) | 95% C.I. for EXP (B) Lower | 95% C.I. for EXP (B) Upper |
|---|---|---|---|---|---|---|
| VSH Hive | 5.436 | 1 | 0.020 | 0.072 | 0.008 | 0.658 |
| HYG Brood | 6.699 | 1 | 0.010 | 0.162 | 0.041 | 0.643 |
| VSH Brood | 7.165 | 1 | 0.007 | 0.098 | 0.018 | 0.537 |
| Year | 10.914 | 1 | 0.001 | 0.025 | 0.003 | 0.225 |
| HYG Brood × VSH Hive | 8.739 | 1 | 0.003 | 44.045 | 3.581 | 541.807 |
| VSH Brood × VSH Hive | 4.365 | 1 | 0.037 | 20.364 | 1.205 | 344.068 |
| HYG Brood × Mite Treatment | 4.996 | 1 | 0.025 | 7.771 | 1.287 | 46.922 |
| VSH Brood × Year | 8.482 | 1 | 0.004 | 64.684 | 3.910 | 1070.046 |
| VSH Brood × VSH Hive × Year | 4.211 | 1 | 0.040 | 0.008 | <0.001 | 0.807 |

In order to understand our results in detail, the effects of brood type on removal were evaluated for each treatment by hive type by year combination. These analyses revealed the importance of brood type on removal in most contexts when the brood was injured or mite parasitized, although effects varied between years (FIG. 1). To evaluate the overall effect of each individual factor (treatment, hive type, and brood type) on brood removal regardless of the other factors, data were pooled across factors to study average effects of one factor at a time. Chi-square analyses were used to determine the individual effects of treatment, hive type and brood type on removal for each year.

Treatment had a significant effect on brood removal rate in 2013 and 2014 (2013: $\chi^2=31.3$, d.f.=2, p<0.001; 2014: $\chi^2=73.4$, d.f.=2, p<0.001) (FIG. 2). In 2013, removal of mite-infested brood was not significantly higher than removal of wounded brood ($\chi^2=2.4$, d.f.=1, p=0.125) but was significantly higher than removal of control brood ($\chi^2=31.2$, d.f.=1, p<0.001). Removal of wounded brood was significantly higher than removal of control brood in 2013 ($\chi^2=16.6$, d.f.=1, p<0.001). In 2014 removal of mite-infested brood was significantly higher than removal of wounded brood ($\chi^2=30.3$, d.f.=1, p<0.001) and control brood ($\chi^2=61.9$, d.f.=1, p<0.001). Removal of wounded brood was significantly higher than removal of control brood in 2014 ($\chi^2=7.4$, d.f.=1, p=0.006).

Hive type had a significant effect on brood removal rate in 2013 but not in 2014 (2013: $\chi^2=61.1$, d.f.=2, p<0.001; 2014: $\chi^2=2.7$, d.f=0263) (FIG. 3). In 2013, removal of brood in VSH hives was significantly higher than removal of brood in HYG hives ($\chi^2=57.5$, d.f.=1, p<0.001), but not significantly different than removal of brood in CON hives ($\chi^2=0.8$, d.f.=1, p=0.359). Removal of brood in HYG hives was significantly lower than removal of brood in CON hives in 2013 ($\chi^2=37.8$, d.f.=1, p<0.001). In 2014, there was no significant difference between removal in CON and HYG hives ($\chi^2=2.6$, d.f.=1, p=0.104), CON and VSH hives ($\chi^2=0.5$, d.f.=1, p=0.480), or HYG and VSH hives ($\chi^2=0.8$, d.f.=1, p=0.378).

In the subset of data for which hive type was the same as brood type, hive type had a significant effect on brood removal rate in 2013 and 2014 (2013: $\chi^2 28.3$, d.f=2, p<0.001; 2014: $\chi^2=10.5$, d.f=2, p=0.005) (FIG. 4). In 2013, removal of brood in VSH hives was significantly higher than removal of brood in HYG hives ($\chi^2=5.26$, d.f=1, p=0,022), and significantly lower than removal of brood in CON hives ($\chi^2=11.269$, d.f=1, p=0.001). Removal of brood in HYG hives was significantly lower than removal of brood in CON hives in 2013 ($\chi^2=28.602$, d.f.=1, p<0.001). In 2014, removal of brood in VSH hives was significantly higher than removal of brood in CON hives ($\chi^2=10.548$, d.f.=1, p=0.001), but was not significantly different from removal of brood in HYG hives ($\chi^2=1.973$, d.f=1, p=0.160). Removal of brood in HYG hives was not significantly different than removal of brood in CON hives in 2014 ($\chi^2=2.594$, d.f.=1, p=0.107).

Brood type had a significant effect on brood removal rate in 2013 and 2014 (2013: $\chi^2=31.4$, d.f.=2, p<0.001; 2014: $\chi^2=42.1$, d.f.=2, p<0.001) (FIG. 5). In 2013, removal of VSH brood was significantly lower than removal of HYG brood ($\chi^2=27.6$, d.f.=1, p<0.001) but not significantly different than removal of CON brood ($\chi^2=2.0$, d.f.=1, p=0.155). Removal of HYG brood was significantly higher than removal of CON brood in 2013 ($\chi^2=129$, d.f.=1, p<0.001). In 2014, removal of VSH brood was significantly higher than removal of HYG brood ($\chi^2=15.2$, d.f=1, p<0.001) and CON brood ($\chi^2=38.3$, d.f=1, p<0.001). Removal of HYG brood was not significantly different than removal of CON brood in 2014 ($\chi^2=2.3$, d.f.=1, p=0.125).

Effects of Hygiene Level on Removal Rate

A significant, positive correlation was identified between removal of brood (regardless of hive breed and treatment) and the level of hygiene of the brood's hive of origin (r=0.680, n=11, p=0.021). No comparable correlation was identified between removal of brood and the level of hygiene of the brood's host hive across treatments and brood breeds (r=−0.414, n=11, p=0.205). There was a significant positive correlation between removal of brood and the level of hygiene of the brood's hive of origin for the mite treatment (r=0.658, n=11, p=0.028; FIG. 6A, Line A). No significant correlation was found for wound (r=0.563, n=11, p=0.072) or control (r=0.455, n=11, p=0.160) treatments (FIG. 6A, Lines B and C, respectively). There was a significant negative correlation between removal of brood and the level of hygiene of the host hive for the wound treatment (r=−0.766, n=1, p=0.006; FIG. 6B, Line B). No significant correlation was found for mite (r=−0.134, n=11, p=0.694) or control (r=−0.389, n=11, p=0.237) treatments (FIG. 6B, Lines A and C, respectively). FIGS. 6A and 6B do not include hives without % hygienic data (n=4).

2. Chemical Study

Methods a. Experiment 2-1

Sample Collection

This chemical study analyzed how cuticular profiles of Varroa-Sensitive Hygienic (VSH), Minnesota Hygienic (HYG) and unselected control (CON) honey bee brood of varying Varroa mite resistance are influenced by Varroa mite, wound and control treatments. All sample collection and analysis was conducted at the University of North Carolina at Greensboro during the summers of 2012, 2013 and 2014. Queens of VSH (n=6, 2 each in 2012, 2013 and 2014), HYG (n=8, 4 in 2012, and 2 each in 2013 and 2014), and control (CON) (n=6, 4 in 2012 and 2 in 2014) origin were caged on wax foundation frames (1 queen per frame). All frames had been drawn out in control (CON) hives immediately before the experiment and were inserted into to each queen's respective hive. In 2013, control (CON) queens did not perform as expected and therefore no data are available from that year for this group. Queen cages were removed once eggs were laid in greater than 75% of cells. After allowing 5 to 6 days for larval development, the locations of uncapped cells containing $5^{th}$ instar larvae were marked using transparent plastic sheets held in place above the experimental cells with thumb tacks. Frames were placed back in the hives for no more than 16 hours to be capped. These recently capped cells were used to ensure that the experimental treatments were all applied to larvae at the same age, within 16 hours of capping. This time window is critical for successful initiation of mite oogenesis. [165]

Within 16 hours of cell capping, mite, wound and control treatments were introduced into marked, capped cells in each frame, and the location of cells containing each treatment was marked on the transparent plastic sheets. Mites used were in the phoretic stage, collected from adult worker bees from control (CON) hives by sugar shake. [105, 187] The collected mites, were introduced to cells using a fine-tipped paintbrush within approximately one hour of collection. Wounds were inflicted using 50 µm diameter capillary needles that mimic mite-inflicted feeding sites [35] and were administered on the dorsal side of the brood between the first abdominal segment and the second thoracic segment according to existing protocols. [186] Control cells were opened and resealed just as mite and wound cells, but received neither mite nor wound treatment. Frames were returned to their hive of origin for 24 hours to allow bees to reseal the cell caps and were then transferred to an incubator maintained at 34° C. with 50% relative humidity (RH). One to four brood from each breed-by-treatment group were collected each day on days 4, 5, and 6 post-capping. These days were chosen because brood removal rates were highest on these three days in a preliminary behavioral study (data not shown). Each individual brood was placed inside a 2 mL screw top glass vial with silicone septa (Agilent, product number 5190-2278). Extraction of brood cuticular chemicals was performed within one hour of sample collection, and no brood that appeared to be damaged from the collection was used.

Cuticular Chemistry

Individual brood were submerged and soaked in hexane for 9 minutes in order to collect non-polar cuticular compounds. The volume of hexane used was varied between approximately 0.5 mL and 1.5 mL, depending on the volume needed to completely submerge each sample. After 9 minutes, the hexane extract was removed from the brood and stored in a separate 2 mL glass vial, Brood and hexane samples were stored at −80° C. until analysis. For extract analysis, hexane was evaporated overnight under a Fisher Hamilton SAFEAIRE® hood. Samples were reconstituted with 50 µL of heptane the following day, after complete evaporation. Heptane used for reconstitution was spiked with butyl butyrate (1 µL butyl butyrate per 10 mL heptane) as an internal standard. For reconstitution, heptane was added to each sample vial for 3 minutes, and the resulting sample transferred into a 400 µL glass flat bottom insert (Agilent product number 5181-3377) using a gas tight 100 µL syringe (Hamilton product number 81062). Glass inserts were used to facilitate operation of the Gas Chromatography Mass Spectrometry (GCMS) autosampler. Use of heptane rather than hexane prevented evaporation of the sample during operation of the autosampler. Samples were analyzed by GCMS to characterize qualitative and quantitative features of the chemical brood extracts. Samples were analyzed at the University of North Carolina at Greensboro on a Shimadzu GCMS-QP2010S (operating at 0.97 kV and acquiring m/z values from 40 to 650). Source and interface temperatures were 230° C. and 250° C. respectively. A 30 m ZebronZB-5MS column with 0.25-mm diameter, 0.5-µm stationary phase thickness was used with helium as the carrier gas (column head pressure 70.2 kPa, total flow rate of 18.1 ml/min, column flow rate of 1.05 ml/min, linear velocity 37.8 cm/sec, purge flow 0.5 mL/min, split ratio −1.0). Column oven temperature was 80° C., injection temperature was 280° C. and injection mode was splitless. After a 1 minute hold, the oven temperature rose from 80 to 165° C. at 15° C./min, and then from 165 to 320° C. at 10° C./min, with a final hold at 320° C. for 10 minutes.

Qualitative and quantitative data were collected for individual honey bee brood samples using GCMS. Since novel peaks were not expected, only the internal standard and cuticular chemicals (n=33) that were reproducibly quantifiable between the majority of samples were used for analysis. For qualitative analysis (peak identification) we used the mass spectral libraries NIST 2005 and WILEY 2007, including supplementary editions. GC-MS post-run analysis software calculated match percentage using an algorithm that compared spectra of the compounds of interest with ions from known library spectra. The length of saturated hydrocarbons was confirmed based on comparison with an external standard composed of Supelco n-hydrocarbon mix (even-numbered alkanes from C8 to C40, diluted 1000:1 with heptane) and spiked with pentadecane (C15). For quantitative analysis, we calculated the proportion of each chemical relative to the total chemicals measured. For each brood sample, we divided the area under each peak (individual peak area) by the sun of the area under all 34 peaks of interest (total peak area), including the 33 cuticular chemicals of interest and the internal standard butyl butyrate. Using the equation below, arcsin transformation was performed for normalization of the proportion data and stabilization of variance. [188]

$$RQ = \sin^{-1}\left(\sqrt{\frac{\text{individual peak area}}{\Sigma \text{ total peak areas}}}\right) \times (100)$$

Triplicate runs for n=2 samples indicated that error due to auto-sampler injection was minimal (average standard error for peak area between triplicate samples was ±0.002). Therefore repeated injections were deemed unnecessary, and each sample for the main analysis was run only one time.

Virus Quantification

After hexane extraction, the quantity of Deformed Wing Virus (DWV) for individual honey bee brood was analyzed. For each sample, RNA was extracted, cDNA was synthesized, and quantitative PCR (qPCR) was performed. For RNA extraction, brood were transferred from glass vials to 2 mL Eppendorf® tubes and homogenized with 0.5 mL TRIzol (ambion by Life Technologies) using a plastic pestle. Samples were incubated at room temperature for 10 minutes. After incubation, another 0.5 mL TRIzol was added to each sample, and then samples were vortexed for twenty seconds on the highest speed setting (#10) of a Fisher Scientific Mini Vortexer. Next, 0.2 mL chloroform was added to each sample, and samples were vortexed again.

Samples were incubated at room temperature for 3 minutes, and then centrifuged at 12,000 RCF for 15 minutes. The top layer of each sample was then pipetted into a 1.5 mL tube containing 0.5 mL of isopropanol. Samples were mixed and placed on ice for 15 minutes, and then centrifuged again at 12,000 RCF for 10 minutes. The supernatant was discarded, and 1 mL of 75% ethanol was added to each pellet, before centrifuging again at 7,500 RCF for 5 minutes. The supernatant was discarded again, and samples were allowed to air dry for 15 minutes. Next, 0.1 mL of molecular grade water (G Biosciences cat#786-72C) was added to each sample to resuspend the pellets. Samples were stored at −80° C. until used for cDNA synthesis.

To determine sample concentration and purity of the RNA extract for cDNA synthesis, a 1 µL RNA aliquot from each extract was analyzed using a Nanodrop ND-1000 Spectrophotometer. The amount of sample needed for 2,000 ng of RNA was then calculated and pipetted into 1.5 mL Eppendorf® tubes. Water was added such that each sample reached a total volume of 8 µL, and then 2.2 µL of DNAse solution containing 1 µL of DNAse 1 µL of DNAse buffer and 0.2 µL of RNAse Out was added to each sample. Samples were then heated to 37° C. for one hour, and then to 75° C. for 10 minutes. Next, for 2013 samples only, 1 µL of a solution containing 0.02 µL dT, 0.5 µL random hexamer, 0.2 µL dNTP, and 0.298 µL H2O was added to each sample. Samples were incubated at 65° C. for 5 minutes and then chilled on ice for 10 minutes. Next, for 2013 samples, 10 µL of a Master Mix containing 4 µL of First Strand buffer, 2 µL of DTT, 0.5 µL of Super Scriptase II, and 3.5 µL of molecular grade water was added to each sample. For 2014 samples, 9.8 µL of Master Mix containing 4 µL 5× TransAmp Buffer, 1 µL, Reverse Transcriptase and 4.8 µL of molecular grade water was added to each sample. Samples were incubated at 42° C. for 50 minutes, and then 70° C. for 15 minutes. Samples were stored at −20° C. until used for RT-qPCR analysis.

RT-qPCR was performed to determine the quantity of DWV in each sample. For each 2013 sample, 1 µL of cDNA, 10 µL Power SYBR Green Mix, 8 µL of water, 0.5 µL of forward primer (sequence: 5'-GAGATTGAAGCGCATGAACA-3')(SEQ ID NO. 1), and 0.5 µL of reverse primer (sequence: 5'-TGAATTCAGTGTCGCCCATA-3')(SEQ ID NO. 2) were added to 0.1 ml MicroAmrp Fast Optical 96-Well Reaction Plate tubes. For each 2014 sample, 2 µL of cDNA, 10 µL of 2× Sensifast SYBR Hi-ROX Mix, 7.2 µL of water, 0.4 µL of forward primer, and 0.4 µL of reverse primer were added to 0.1 ml MicroAmp Fast Optical 96-Well Reaction Plate tubes. Liquid was centrifuged to the bottom and samples were run through 45 cycles on an Applied Biosystems StepOne Plus qPCR machine set to SYBR as the passive agent. Samples were analyzed for DWV as well as for the two reference genes, Actin (forward primer sequence: 5'-TTGTATGCCAACACTGTCCTTT-3' (SEQ ID NO. 3); reverse primer sequence: TGGCGCGATGATCTTAATTT-3' (SEQ ID NO. 4)) and RPS5 (forward primer sequence: 5'-AATATTATTTGGTCGCTGGAATTG-3' (SEQ ID NO. 5); reverse primer sequence: 5'-TAACGTCCAGCAGAATGTGGTA-3' (SEQ ID NO. 6)). Each transcript for each sample was run in triplicate.

Based on RT-qPCR results, DWV was classified as either "low" or "high" for each sample. Samples were categorized as "low" for DWV if the cycle threshold ($C_T$) was undetermined in all three replicates, or if only one replicate contained a determined $C_T$ with a secondary peak at the correct melting temperature (Tm). Samples were categorized as "high" for DWV if at least one replicate contained a determined $C_T$ with the primary peak at the correct Tm, or if two or more replicates contained determined $C_T$ values with a secondary peaks at the correct Tm. DWV was also placed on a continuous scale by calculating an average Delta $C_T$ for each sample. Delta $C_T$ was calculated for each sample by taking the average of the Delta $C_T$ across all three replicates. When no $C_T$ value was determined, a $C_T$ of 45 (the number of cycles used for RT-qPCR) was used. Delta $C_T$ was calculated using the following equation, such that the higher the Delta $C_T$ value, the greater the amount of DWV in the sample:

$$\text{Delta } CT = CT(\text{Actin}) - CT(DWV)$$

Statistical Analysis

A full factorial MANOVA was used to determine whether treatment (mite, wound and control) affected chemical signatures of brood across brood type (control (CON), HYG and VSH) and age (days 4, 5, and 6 post-capping) age. The Wilks' Lambda statistic is reported. As a follow-up to MANOVA, ANOVAs were used to evaluate how certain chemicals of interest differed by treatment for each brood type. ANOVA was also used to determine the effects of DWV load on mean P32 quantity of brood. A significance level of 0.05 was used for all statistical tests. All statistical analyses were performed using IBM SPSS Statistics, Version 22.

b. Experiment 2-2

Sample Collection

A combined behavioral-chemical study analyzed how cuticular profiles of uncapped, mite infested honey bee brood differed from those of control brood that remained capped. As described above, mite and control treatments were introduced to recently capped cells in single frames from each of two VSH hives. The cells containing introduced mites were monitored periodically for uncapping from day 3 to day 6 post-capping. Each time one mite-infested brood was found to be uncapped and apparently unharmed (i.e.: removal by nurse bees had not yet begun), the brood was collected. Each time an uncapped, mite-infested brood was collected, two control brood were also collected at the same time—one from a capped, mite-infested cell, and one from a capped control cell (FIG. 9A). In total, six uncapped, mite-infested cells were collected, three from each hive. In the first hive, the 3 uncapped brood and their 6 controls were collected on days 3, 3, and 6 post-capping. In the second hive, the 3 uncapped brood and their six controls were collected on days 5, 6 and 6 post-capping. Each individual brood was placed inside a 2 mL screw top glass vial. Extraction of brood cuticular chemicals was performed within one hour of sample collection as described above, ensuring by visual inspection that no brood appeared to be damaged from the collection.

Cuticular Chemistry

As described above for Experiment 2-1, individual brood were submerged and soaked in hexane for 9 minutes in order to collect non-polar cuticular compounds. All methodology for chemical extraction and analysis in Experiment 2-2 was the same as that listed above for Experiment 2-1. However for each sample in Experiment 2-2, only the relative quantity of the six peaks that were found to differ significantly with treatment in Experiment 2-1 (P32, P28, P25, P18, P15, and PL4) were evaluated.

FIG. 7 shows the GCMS output from a single, mite-infested honey bee, illustrating the location of the P32 peak (top) and the mass-to-charge ratio for P32 (bottom).

Virus Quantification

As described above for Experiment 2-1, individual brood were analyzed for DWV content. All methodology for RNA extraction, cDNA synthesis, RT-qPCR, and RT-qPCR analysis in Experiment 2-2 was the same as that listed for 2014 in Experiment 2-1.

Statistical Analysis

Paired-sample t-tests were used to determine whether the mean quantity of each of the six peaks identified to be significantly affected by treatment in Experiment 2-1 differed for the following paired samples: uncapped, mite-infested honey bee brood vs. capped mite-infested brood; uncapped, mite-infested honey bee brood vs. capped mite-free controls; and capped mite-infested brood vs. capped mite-free controls. Paired-sample t-tests were chosen because uncapped samples were collected on different times and days. Because honey bee brood chemical are age dependent, samples could only be compared with those collected at the same time point. Since direction of the differences could be predicted before the tests based on results from Experiment 2-1, a one-tailed statistical test was used. A significance level of 0.05 was used for all statistical tests.

Results a. Experiment 2-1

A full factorial MANOVA was run to understand the effects of treatment, brood type, age, and their interactions on the quantities of the 33 honey bee cuticular chemicals. Significant effects on brood cuticular profiles were identified for treatment (F=1.61, d.f.=66,708, p=0.002), brood type (F=5.42, d.f.=66,708, p<0.001), and age (F=26.52, d.f.=66, 708, p<0.001). A treatment-by-age interaction (F=1.27, d.f.=132, 1411, p=0.026), and a brood type-by-age interaction (F=1.59, d.f=132, 1411, p<0.001) were also found. No significant effects were identified for the treatment-by-brood type interaction (F=0.74, d.f.=132, 1411, p=0.987) or the treatment-by-by-brood type-by-age interaction (F=0.53, d.f.=264, 2775, p=0.877).

Two-way ANOVAs indicated that of the 33 chemicals analyzed, 6 were significant for treatment effects, 18 were significant for brood type effects, 29 were significant for age effects, I was significant for treatment-by-age interaction effects, and 12 were significant for brood type-by-age interaction effects. Of the 6 chemicals significantly affected by treatment, the mean quantity of peak number 32 (P32) was found to be higher in mite-infested brood than in controls while the mean quantity of peaks numbered 28, 25, 18, 15, and 14 (P28, P25. P18, P15 and P14, respectively) were found to be lower in mite-infested brood than in controls (data not shown). Since the primary interest of this study was to explore the effects of interactions between treatment and brood type on cuticular chemicals, the 6 peaks significantly affected by treatment were explored in more depth using separate ANOVAs for each brood type. While the mean quantity of P32 was higher in mite-infested brood than control brood for all three brood breeds, the ANOVAs indicated that this difference was only significant for VSH brood (F=42.67, d.f.=1, p=0.031), and was not significant for HYG (F=1.06, d.f=1, p=0.307) or control (CON) (F=0.10, d.f.=1, p=0.760) brood (FIG. 8A ; sample size: control (CON) brood n=18 for both treatments; HYG brood n=41 for control and n=42 for mite-treated; VSH brood n=44 for control and n=39 for mite-treated). Since the effects of brood breed and virus levels on cuticular chemicals were also of interest, the effect of DWV on P32 was also explored using separate ANOVAs for each brood type. The virus data from 2012 brood was incomplete and much higher than that of the following years. We deemed those 2012 values unreliable and did not include them in the analysis. Thus, all virus data refers to brood from 2013 and 2014. The mean quantity of P32 was significantly higher in brood with high DWV levels than in those with low DWV levels for both control (CON) (F=6.52, d.f.=1, p=0.014) and HYG (F=12.45, d.f.=1, p=0.001) brood (FIG. 8B; sample size: control (CON) brood n=32 for low DWV levels and n=22 for high DWV levels; HYG brood n=96 for low DWV levels and n=30 for high DWV levels; VSH brood n=62 for low DWV levels and n=62 for high DWV levels). There was no significant effect of DWV level on P32 for VSH brood (F=0.17, d.f.=1, p=0.679). For the sake of comparison between the effects of treatment and virus levels on P32, results for the effect of treatment on the mean quantity of P32 for each brood type were also calculated using only the data from 2013 and 2014. As with the full data set, the mean quantity of P32 was higher in mite-infested brood than control brood for all three brood breeds, but the ANOVAs indicated that this difference was only significant for VSH brood (F=4.26, d.f.=2, p=0.016), and not for HYG (F=0.863, d.f=2, p=0.424) or control (CON) (F=0.069, d.f.=2, p=0.933) brood.

Individual ANOVAs suggested that the mean quantities of P28, P25, P18, P15 and P14 were not significantly different between treatment groups in any of the three brood types (data not shown). The mean quantity of P28 was significantly lower in brood with high DWV levels than in those with low DWV levels for both control (CON) (F=13.31, d.f=1, p=0.001) and HYG (F=14.90, d.f=1, p<0.001) brood. There was no significant effect of DWV level on P28 for VSH brood (F=1.93, d.f=1, p=0.167). The mean quantity of P25 was significantly lower in brood with high DWV levels than in those with low DWV levels for both control (CON) (F=11.32, d.f.=1, p=0.001) and HYG (F=8.45, d.f.=l, p=0.004) brood. There was a suggestive effect of DWV level on P25 for VSH brood (F=3.00, d.f.=1, p=0.086). The mean quantities of P18, P15 and P14 were not significantly different for DWV levels in any of the three brood types (data not shown).

b. Experiment 2-2

For each of the six peaks identified (P32, P28, P25, P18, P15, and P14) to be significantly affected by treatment in Experiment 2-1, paired-sample t-tests were used to compare the mean peak quantity of uncapped, mite-infested brood to either capped, mite-infested brood or capped mite-free controls. Paired-sample t-tests were also used to compare mean peak quantity of capped, mite-infested brood and capped, mite-free controls. Mean P32 quantity was significantly higher for uncapped, mite-infested brood than for either capped mite-infested (t=2.85, df=5, p=0.018) or capped mite-free (t=3.71, df=5, p=0.007) controls (FIG. 9B). Each relative quantity of P32 is based on an average of six samples. Each time collection from a mite-infested cell that had been uncapped was made (n=6), collection from two controls were also made, one with a mite (n=6) and one without (n=6).) As shown in FIG. 9B, there was no significant different in mean P32 quantity between capped mite-infested and capped mite-free controls (t=1.24, df=5, p=0.136).

Mean P28 quantity was significantly lower for uncapped, mite-infested brood than for the capped mite-free (t=2.17, df=5, p=0.041) control. There was no significant difference in mean P28 quantity between capped mite-infested and either the uncapped, mite-infested brood (t=1.16, df=5, p=0.150) or the capped mite-free control (t=0.99, df=5, p=0.184). Mean P25 quantity was not significantly different for uncapped, mite-infested honey bee brood and capped mite-infested brood (t=−0.63, df=5, p=0.279), uncapped, mite-infested honey bee brood and capped mite-free controls (t=−0.53, df=5, p=0.310), or capped mite-infested brood and capped mite-free controls (t=−0.10, df=5, p=0.464). Mean P18 quantity was not significantly different for uncapped, mite-infested honey bee brood and capped mite-infested brood (t=−1.i 42, df=5, p=0.108), uncapped, mite-infested honey bee brood and capped mite-free controls (t=−1.40, df=5, p=0.111), or capped mite-infested brood and capped mite-free controls (t=−0.84, df=5, p=0.220). Mean P15 quantity was not significantly different for uncapped, mite-infested honey bee brood and capped mite-infested brood (t=−0.14, df=5, p=0.449), uncapped, mite-infested honey bee brood and capped mite-free controls (t=1.00, df=5, p=0.182), or capped mite-infested brood and capped mite-free controls (t=1.00, df=5, p=0.182). Mean P14 quantity was not significantly different for uncapped, mite-infested honey bee brood and capped mite-infested brood (t=−1.64, df=5, p=0.082), uncapped, mite-infested honey bee brood and capped mite-free controls (t=−0.84, df=5, p=0.221), or capped mite-infested brood and capped mite-free controls (t=0.61, df=5, p=0.284), DWV was only detected in one sample: a capped, mite-infested control, so DWV is not thought to play a role in differences measured.

Consistent results were obtained with an increased sample size, wherein each relative quantity of P32 is based on an average of 24 samples (the previously analyzed 6 samples from 2014 and 18 samples from 2015). Each time collection from a mite-infested cell that had been uncapped was made (n=24), collection from two controls were also made, one with a mite (n=24) and one without (n=24). ANOVA was used to compare the mean peak quantity of uncapped, mite-infested brood to either capped, mite-infested brood or capped, mite-free controls. ANOVA was also used to compare mean peak quantity of capped, mite-infested brood and capped, mite-free controls. As shown in FIG. 9C, uncapped mite-infested brood had a significantly higher mean relative percent P32 than did capped mite-infested ($F_{(1,46)}$=16.956, p<0.001) or capped control ($F_{(1,46)}$=21.429, p<0.001) brood. There was no significant difference between the mean relative percent P32 for capped mite-infested and capped control brood ($F_{(1,46)}$=0.654, p=0.423).

Mean P28 quantity was not significantly different for uncapped, mite-infested honey bee brood and capped mite-infested brood ($F_{(1,46)}$=0.508, p=0.479), uncapped, mite-infested honey bee brood and capped mite-free controls ($F_{(1,46)}$=0.310, p=0.580), or capped mite-infested brood and capped mite-free controls ($F_{(1,46)}$=0.017, p=0.898). Mean P25 quantity was not significantly different for uncapped, mite-infested honey bee brood and capped mite-infested brood ($F_{(1,46)}$=0.073, p=0.788), uncapped, mite-infested honey bee brood and capped mite-free controls ($F_{(1,46)}$=0.784, p=0.380), or capped mite-infested brood and capped mite-free controls ($F_{(1,46)}$=0.304, p=0.584). Mean P18 quantity was not significantly different for uncapped, mite-infested honey bee brood and capped mite-infested brood ($F_{(1,46)}$=1.045, p=0.312), uncapped, mite-infested honey bee brood and capped mite-free controls ($F_{(1,46)}$=0.296, p=0.589), or capped mite-infested brood and capped mite-free controls ($F_{(1,46)}$=0.407, p=0.527). Mean P15 quantity was not significantly different for uncapped, mite-infested honey bee brood and capped mite-infested brood ($F_{(1,46)}$=0.574, p=0.453), uncapped, mite-infested honey bee brood and capped mite-free controls ($F_{(1,46)}$=0.127, p=0.723), or capped mite-infested brood and capped mite-free controls ($F_{(1,46)}$=0.159, p=0.692). Mean P14 quantity was not significantly different for uncapped, mite-infested honey bee brood and capped mite-infested brood ($F_{(1,46)}$=2478, p=0.122), uncapped, mite-infested honey bee brood and capped mite-free controls ($F_{(1,46)}$=0.939, p=0.338), or capped mite-infested brood and capped mite-free controls ($F_{(1,46)}$=0.432, p=0.514). Again, DWV is not thought to play a role in differences in hygienic behavior measured. DWV titers were significantly higher in mite-infested cells than non-infested cells ($F_{(1,67)}$=3.005, p=0.044) but did not differ significantly between capped mite-infested cells and uncapped mite-infested cells ($F_{(1,46)}$=0.041, p=0.420).

3. Induced Hygienic Behavior Study with Mite-Infested Brood Extract

Methods

CHC extracts of the same volume but different concentrations representing 3 brood, 1 brood, and 0.3 brood (3, 1, 0.3 brood equivalents (BEqs) respectively) were transferred from mite-infested and control brood to the wax caps of healthy cells. The experiment could have been performed in any type of hive. Given the brood treatment effect described above, VSH hives were preferred and selected as a first test.

The bioassay was performed using experimental brood aged 4 days post-capping, as our previous findings suggest that this is the brood age at which hygienic behavior is most likely to occur (data not shown). Appropriately aged brood was identified 4 days before each bioassay via marking of recently capped cells, as described above.

To collect CHC extracts from brood, the location of uncapped cells containing $5^1$ instar larvae were marked using a permanent marker and transparent plastic sheet secured over each frame with thumb tacks. Frames were placed back into the hives. The following day, frames were recollected, and only brood that had been capped was marked for experimental use. Within 18 hours of capping, Varroa mites was introduced to approximately 50% of capped cells. Careful timing of Varroa introductions is necessary to ensure initiation of mite oogenesis. [165, 37] Mites used were collected by sugar shake [187, 105] from a donor colony and were introduced randomly to cells using a fine-tipped paintbrush. The remaining 50% of capped cells were control cells. Control cells were opened and resealed just as mite cells, but did not receive a mite.

Brood from 65 mite-infested cells and an equal number of non-infested cells were collected on the $4^{th}$ day post-capping. Pools of 5 brood were soaked for 9 minutes in approximately 1.5 ml hexane. The solvent containing brood cuticular extracts was then removed from the brood. The extracts collected from within each treatment group (mite-infested and control) were combined in their respective groups, evaporated overnight, and reconstituted using a total of 90 μl of hexane. After a 3 minute wait period the remaining 65 μl for each treatment group was aliquoted into vials labeled with three different brood-equivalent (BEq) concentrations: 3 BEq, 1 BEq, and 0.3 BEq. These vials received 45, 15 and 5 μl of the extract, respectively. Samples were evaporated overnight again, transported on ice to the bee station, and then reconstituted (one at a time) using 33 μl hexane. After a 3 minute wait period, the remaining 30 μl of extract was collected in an airtight syringe, and aliquoted onto 15 randomly selected wax caps of experimental cells (2 μl per cell). This was repeated for each extract concentration (3 BEq, 1 BEq and 0.3 BEq) for each treatment (mite and control). The brood frame was then placed back into the hive, and uncapping and removal were checked and recorded after 8, 24, and 48 hours.

A chi-square analysis was used to test for a difference in uncapping between treatment groups. The statistical test was performed using IBM SPSS Statistics, Version 22.

Results

Mite-infested brood extract at concentrations of 0.3 BEq and 1 BEq each induced more uncapping than control brood extract at concentrations of 0.3 BEq and 1 BEq, respectively; and more uncapping than hexane treatment (FIG. 10). Mite-infested brood extract at a concentration of 3 BEq did not demonstrate significant differences from control brood extract at a concentration of 3 BEq; however both demonstrate more uncapping compared to hexane treatment (FIG. 10). Control brood extract at a concentration of 3 BEq demonstrated uncapping effects, likely due to excessive concentrations of both hexane and control brood extract.

Figure i compares control brood extract and mite-infested brood extract, using the same data represented in FIG. 10 and combining data sets from all three concentrations of 0.3 BEq, I BEq, and 3 BEq for each group. Mite-infested brood extract induced significantly more uncapping than extracts from control brood extract (FIG. 11) ($\chi^2=3.64$, d.f.=1, p=0.029).

While the majority of studies of hygienic behavior mechanisms have focused on sensitivity and modulation of adult olfaction [10, 31, 85, 166, 167, 175], recent evidence indicates the importance of brood signals in triggering of hygienic behavior. [102, 176, 179]

The chemical study above demonstrates significant P32 levels in i) *Varroa* mite-treated VSH brood (FIG. 8A), ii) both control and HYG brood with high levels of Deformed Wing Virus (FIG. 8B), and iii) uncapped hive cells with *Varroa*-infested brood (FIGS. 9B and 9C). The behavioral study above demonstrates a positive correlation between removal of brood and the level of hygiene of the brood's hive of origin.

4. Examples: Induced Hygienic Behavior Studies with a Tritriacontene a. Synthesis of a Tritriacontene Methods:

Synthesis methods of a tritriacontene or agriculturally acceptable derivatives can be readily determined by those skilled in the art, including but not limited to the field of insect semiochemicals. Synthesis methods generally include, but are not limited to, alkylation of a long, straight-chained alkyne followed by reduction to form the double bond (see for example, use of two commercially available synthons [206]); a cis-selective Wittig reaction [207]; and an olefin metathesis reaction [205]. Also, certain tritriacontenes are commercially available. For example, (Z)-10-tritriacontene, which has the structure, is commercially available (CAS Registry No. 99026-87-6). Products may be purified by gas chromatography and/or recrystallization. Identity and purity of the compound may be ascertained by GC-MS analysis. In addition to analyzing the synthesis product alone, it will be added to aliquots of hexane extracts of *Varroa*-mite infested VSH brood to quantify the increase of the P32 peak, relative to the other constituents of the extracted mixture.

Results:

(Z)-10-tritriacontene and (Z)-16-dotriacontene (Z10-C320), described below, were synthesized by collaborator Jocelyn Millar from the University of California Riverside using standard procedures. The identity of the synthesized (Z)-10-tritriacontene was verified using comparative GC-MS analysis of a honey bee brood cuticular extract with and without a spike of the synthesized compound. The peak from the synthesized (Z)-10-tritriacontene coincided perfectly with the P32 peak from the honey bee brood extract. Accordingly, "P32" and "(Z)-10-tritriacontene" and "Z10-C33" are used interchangeably herein.

b.i. Induced Hygienic Behavior Study with Synthesized P32

Methods: The pure P32 compound will be aliquoted and diluted in hexane.

1 ul of different dilutions will be applied onto larvae and/or caps of individual brood cells in three experimental hives. The VSH, MH, and control genotype (together, hereinafter, referred to as "line") will be tested for their response. Hives from each source will be set up in an experimental apiary and standardized in size, brood, and resources.

Brood frames containing uncapped $5^{th}$ larval instars will be collected from each hive, and the location of the uncapped cells will be marked using a plastic transparency [208]. Frames will be replaced into the hives, and cells that are capped within the next 16 hours will be recorded and used for the experiment. At day 4 post-capping, cells will be treated with hexane (a negative control) or one of the following dilutions of pure P32: $10^{-1}$, $10^{-3}$, $10^{-5}$, $10^{-7}$, $10^{-9}$, $10^{-11}$. Pin-killed brood will be used as a positive control. Twenty cells will receive each treatment in each colony for a total sample size of 1440 (20 cells×8 treatments×3 replicate hives×3 genotypes).

Treatments will be randomly distributed across experimental combs and the location of each treatment recorded on a clear transparent sheet put over the comb [208]. Cell uncapping behavior and removal of brood will be surveyed 1 hour, 4 hours, 8 hours, and 24 hours after treatment. Uncapping and removal rates at each time point will be compared among the different experimental groups in each colony. Chi-squared analysis will be used to test for differ-

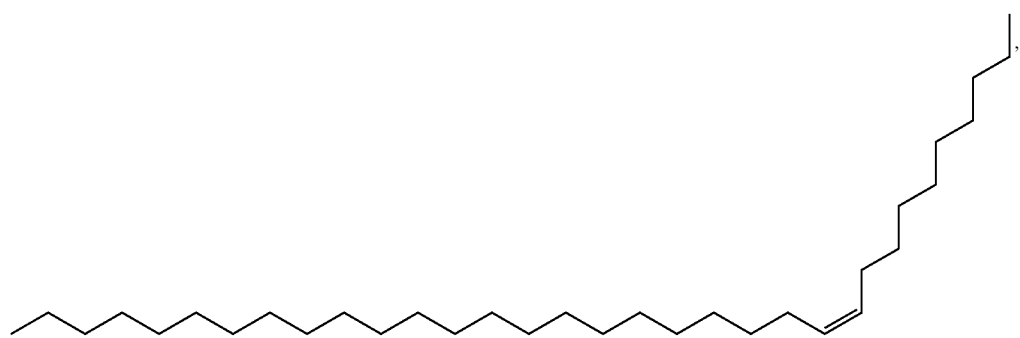 [SMILES: CCCCCCCCC/C=C\CCCCCCCCCCCCCCCCCCCCCC]

ences in the frequency of hygienic behavior between treatment groups at each time point.

Results:

Synthesized P32 and controls were applied to cell caps by syringe. Results suggested significantly higher removal of P32-treated cells compared to hexane treated cells in both of the MH colonies tested. No VSH colonies were available for testing, and no significant difference was observed between removal of P32- and hexane-treated cells in control colonies. However, methodological issues justified the discarding of these results, and repetition of the experiment using improved methods. Specifically, chemical dilutions were not properly performed because the volume of the experimental chemical was not taken into account when making dilutions in the hexane solvent. Additionally, high variability between pin-killed treatments suggested that these were not reliable as positive controls. The following experiment serves as a replacement for the experiment described above. Improved methods in the replacement experiment below include corrected dilution procedures (solvent was added to the experimental chemical to a specific final volume), removal of the pin-killed positive control, and use of the alkene (Z)-16-dotriacontene (also called Z16-C32) as the negative control. Compared to the alkanes used previously, (Z)-16-dotriacontene more closely resembles P32, and thus serves as a more appropriate negative control. A new method for application of chemicals by airbrushing was also utilized to increase speed and quantity in chemical application (FIG. 12).

b.ii. Induced Hygienic Behavior Study with Synthesized P32 Applied to Cell Caps by Airbrushing Methods: The dose dependent removal effects of (Z)-10-tritriacontene and (Z)-16-dotriacontene applied to wax caps of honey bee brood cells were measured repeatedly in a single VSH colony. (Z)-10-tritriacontene, along with (Z)-16-dotriacontene and hexane controls were applied to capped honey bee brood cells using a Paasche H-100D Single Action Airbrush & Compressor system, operating at 25 PSI. To control the amount of brood cells exposed to each chemical treatment (and thus the dose per cell) 3" diameter PVC pipe pieces were inserted into a brood frames containing capped pupae. Thus, for each treatment and replicate, 2 mL of solution was applied to a single 3"-diameter section of brood comb by airbrushing. Since there are roughly 200 cells per 3" diameter circle, this is roughly 10 ul solution per cell. Concentrations of 1%, 0.3%, and 0.1% (Z)-10-tritriacontene and (Z)-16-dotriacontene were tested. Sample sizes for (Z)-10-tritriacontene were 532, 420, and 282 cells for concentrations of 1%, 0.3%, and 0.1%, respectively. Sample sizes for (Z)-16-dotriacontene were 289, 296, and 311 for concentrations of 1%, 0.3%, and 0.1%, respectively. Sample sizes for the hexane control and no treatment control were 425 and 154, respectively. The location of all assays on frames was randomized. The frequency of uncapping and removal was recorded at four hours and twenty-four hours post treatment. Chi-square analysis with Bonferroni correction was used to compare hygienic removal and uncapping between treatments.

Results:

Removal of pupae in brood cells treated with 1% and 0.3% (Z)-10-tritriacontene was significantly greater than that of pupae in all control brood cells, including cells treated with any concentration of (Z)-16-dotriacontene (FIG. 13). Both (Z)-10-tritriacontene and (Z)-16-dotriacontene appear to be removed in a dose-dependent manner, with the highest concentrations eliciting the greatest removal. These results indicate that the removal effect is specific to (Z)-10-tritriacontene, supporting our hypothesis that this (Z)-10-tritriacontene is a natural trigger of hygienic removal in honey bees. While the relatively high removal rates of pupae in cells treated with (Z)-10-tritriacontene indicates that this or a similar assay may be useful for selection of hygienic honey bees, more studies are needed to determine an optimal dose for triggering uncapping of cells and a) removal of diseased brood or b) recapping of healthy brood.

c. Prophetic Example: Induced Hygienic Behavior Study with P32-Spiked Extracts

Hexane will be used to extract cuticular chemicals from 200 mite-infested and 200 non-infested honey bee larvae aged 4-days post capping. The pooled mite-infested and pooled non-infested larval extracts will each be divided into five vials of 40 brood equivalents (Beq) each, and spiked with 40 µl of one of the following: hexane, $10^{-3}$ P32, $10^{-1}$P32, $10^{-7}$P32, $10^{-9}$ P32. Spiked extracts in each vial will be evaporated under a stream of nitrogen and reconstituted in 40 µl of hexane. At day 4 post-capping, wax-caps of cells and/or larvae in each cell will be treated with 1 ul of each extract type. Forty cells will receive each treatment for a total sample size of 400 (40 cells×2 extract types×5 P32 treatments).

Treatments will be randomly distributed across experimental combs and the location of each treatment recorded on a clear transparent sheet put over the comb. Cell uncapping behavior and removal of brood will be surveyed 1 hour, 4 hours, 8 hours, and 24 hours after treatment. Chi-squared analysis will be used to test for differences in the frequency of hygienic behavior between treatment groups at each time point.

d. Prophetic Example: Commercial Scale Induced Hygienic Behavior Study with P32 Treatment for *Varroa*-Infested Honey Bee Hives The P32 compound will be synthesized at a larger scale. Based on the results of the smaller-scale studies above in subsection 4.1.b, an application to deliver the most efficient P32 concentration will be formulated and readily determined by those skilled in the art. The formulation may be a spray that can be applied homogenously onto brood frames.

Thirty experimental hives will be established and integrated into the regular operation of a commercial beekeeper. To simulate the *Varroa* mite infestation of more mature hives, each experimental hive will receive 20 adult mites, obtained by "sugar shaking" [105]. A comprehensive pre-assessment of the experimental hives, including *Varroa* mite populations and virus prevalence, will be conducted followed by the actual experiment applying P32 as a *Varroa* treatment [59, 105, 209]. Specific variables that will be assessed are *Varroa* mite counts on sticky bottom boards and *Varroa* population determined by alcohol washes of adult bees [105], the prevalence of ten viruses in 24 individual pupae [210], queen presence and drone population, open and capped brood quantity and solidness, worker population, and stored pollen and honey, according to existing protocols [209]. Throughout the active season until August, P32 treatments will be performed in 15 randomly selective hives, while the remaining 15 will remain untreated controls. P32 will be applied every 21 days, according to the length of one honey bee brood cycle. Although the *Varroa* life cycle is considerably shorter than this interval, this application frequency will be effective and an even lower frequency is anticipated to be optimal from an economic perspective.

Just prior to each P32 application and at the end of the experimental period, hives will be inspected as above, and the data will be recorded in the field for subsequent analyses by simple comparisons of hive strength and health variables between treatment and control hives. In addition, subsequent over wintering success of these hives will be reported to gain a comprehensive understanding of the impact of a P32 treatment in a commercial setting.

e. Prophetic Example: Bioassay for Hygienic Behavior in Honey Bees

Methods:

The timing of the induced uncapping behavior determined in the experiment of in subsection 4.1.b above will inform this bioassay study. The conventional "freeze-killed brood" assay [100] will be compared to a new P32-spray assay for labor, reproducibility, and predictive power of overall performance outcome of the assayed hives.

A sample of 120 representative hives in different locations will be tested with both assays simultaneously. In parallel to the "freeze-killed brood" assay, P32 will be sprayed on a section of capped brood comb of identical size. Uncapping and removal of brood will be recorded for both assays 2, 4, 8, and 24 hours after treatment. On the following day, both assays will be repeated on a second frame from the same hives. The 16 different variables (4 time points×2 assays×2 outcomes: uncapped or removed) will be assessed for repeatability by correlating the scores from the first day with the corresponding scores from the second day. For each hygienicity variable an overall value will be computed as the average of corresponding scores from both days. The size and health of the 120 colonies will also be assessed [209] at this time. The survival of the hives will be recorded throughout the season and a final assessment of *Varroa* population [105], size and health will be performed. The relation between hive performance and the overall values of the hygienicity variables will be quantified in a general linear model to assess the predictive power of each variable.

Results:

A trial of this experiment was completed on a small scale. In 10 colonies with various selective breeding histories, removal of brood in capped cells treated with 1% (Z)-10-tritriacontene applied by airbrushing was compared, side-by-side in single frames, to removal of brood in capped cells treated with liquid nitrogen (FKB assay). The frequency of uncapping and removal in each assay was recorded at two hours and twenty-four hours post treatment. Results indicate a significant positive correlation at 24 hours (Pearson Correlation Coefficient=0.688, p=0.014) between uncapping and removal of cells treated with P32 and those treated with liquid nitrogen (FIG. 14).

REFERENCES

1. Biesmeijer J C, Roberts S P, Reemer M, Ohlemuller R, Edwards M, Peeters T, Schaffers A P, Potts S G, Kleukers R, Thomas C D et al: Parallel declines in pollinators and insect-pollinated plants in Britain and the Netherlands. *Science* 2006, 313(5785):351-354.
2. Potts S G, Biesmeijer J C, Kremen C, Neumann P, Schweiger O, Kunin W E: Global pollinator declines: trends, impacts and drivers. *Trends Ecol Evol* 2010, 25(6):345-353.
3. Morse R A, Calderone N W: The value of honey bees as pollinators of U.S. crops in 2000. *Bee Culture* 2000, 128:1-15.
4. Committee on the Status of Pollinators in North America NRC: Status of Pollinators in North America. Washington, D C: The National Academies Press; 2007.
5. Calderone N W: Insect pollinated crops, insect pollinators and U S agriculture: trend analysis of aggregate data for the period 1992-2009. *PLoS One* 2012, 7(5):e37235.
6. Singh R. Levitt A L, Rajotte E G, Holmes E C, Ostiguy N, vanEngelsdorp D, Lipkin W I, dePamphilis C W V, Toth A L, Cox-Foster D L: RNA viruses in Hymenopteran pollinators: Evidence of inter-taxa virus transmission via pollen and potential impact on non-*Apis Hymenopteran* species. *PLoS One* 2010, 5(12):e14357.
7. Winston M L: The Biology of the Honey Bee. Cambridge, Mass.: Harvard University Press; 1987.
8. Boecking O, Spivak M: Behavioral defenses of honey bees against *Varroa jacobsoni Oud. Apidologie* 1999, 30(2-3): 141-158.
9. Spivak M, Reulter G S: *Varroa destructor* infestation in untreated honey bee (Hymenoptera:Apidae) colonies selected for hygienic behavior. *J Econ Entomol* 2001, 94(2):326-331.
10. Spivak M, Masterman R, Ross R, Mesce K A: Hygienic behavior in the honey bee (*Apis mellifera* L.) and the modulatory role of octopamine. *J Neurobiol* 2003, 55(3): 341-354.
11. Wilson-Rich N, Spivak M, Fefferman N H, Starks P T: Genetic, individual, and group facilitation of disease resistance in insect societies. *Annu Rev Entorol* 2009, 54:405-423.
12, Oldroyd B P, Fewell J H: Genetic diversity promotes homeostasis in insect colonies. *Trends Ecol Evol* 2007, 22(8):408-413.
13. Whitfield C W, Behura S K, Berlocher S H, Clark A G, Johnston J S, Sheppard W S, Smith D R, Suarez A V, Weaver D, Tsutsui N D: Thrice out of Africa: Ancient and recent expansions of the honey bee, *Apis mellifera. Science* 2006, 314(5799):642-645.
14. Ruttner F: Biogeography and Taxonormy of Honeybees. Berlin: Springer: 1988.
15. Goulson D, Nicholls E, Botias C, Rotheray E L: Bee declines driven by combined stress from parasites, pesticides, and lack of flowers. *Science* 2015, 347(6229): DOI: 10.1126/science.1255957.
16. Hawthorne D J, Dively G P: Killing them with kindness? In-hive medications may inhibit xenobiotic efflux transporters and endanger honey bees. *PLoS One* 2011, 6(11):e26796.
17. vanEngelsdorp D, Evans J D, Saegerman C, Mullin C, Haubruge E, Nguyen B K, Frazier I M, Frazier J, Cox-Foster D, Chen Y et al: Colony Collapse Disorder: A descriptive study. *PLoS ONE* 2009, 4(8):e6481.
18. vanEngelsdorp D, Meixner M D: A historical review of managed honey bee populations in Europe and the United States and the factors that may affect them. Journal of *Invertebrate Pathology* 2010, 103:S80-S95.
19. McMenamin A J, Genersch E: Honey bee colony losses and associated viruses. Current Opinion in Insect *Science* 2015, 8:doi.org/10.1016/j.cois.2015.1001.1015.
20. van Dooremalen C, Gerritsen L, Comelissen B, van der Steen J J M, van Langevelde F, Blacquiere T: Winter survival of individual honey bees and honey bee colonies depends on level of *Varroa destructor* infestation. *PLoS One* 2012, 7(4):e36285.
21. Dainat B. Evans J D, Chen Y P, Gauthier L. Neumann P: Predictive markers of honey bee colony collapse. *PLoS One* 2012, 7(2):e32151.
22. Cox-Foster D L, Conlan S, Holmes E C, Placios G, Evans J D, Moran N A, Quan P L, Briese T, Homrnig M, Geiser D M et al: A metagenomic survey of microbes in honey bee colony collapse disorder. *Science* 2007, 318 (5848):283-287.
23. Higes M, Martin-Hernandez R, Botias C, Bailon E G, Gonzalez-Porto A V, Barrios L, del Nozal M J, Benal J L, Jimenez J J, Palencia P G et al: How natural infection by Nosema ceranae causes honeybee colony collapse. *Environ Microbiol* 2008, 10(10):2659-2669.
24. Johnson R M, Evans J D, Robinson G E, Berenbaunm M R: Changes in transcript abundance relating to colony collapse disorder in honey bees (*Apis mellifera*). *Proc Natl Acad Sci USA* 2009, 106(35): 14790-14795.
25. Cornmman R S, Tarpy D R, Chen Y, Jeffreys L, Lopez D, Pettis J S, vanEngelsdorp D, Evans J D: Pathogen webs in collapsing honey bee colonies. *PLoS One* 2012, 7(8): e43562.
26. Genersch E: Honey bee pathology: current threats to honey bees and beekeeping. *Appl Micriobiol Biot* 2010, 87(1):87-97.
27. Schmid-Hempel P: Parasites in Social Insects. Princeton, N.J.: Princeton University Press; 1998.
28. Runckel C, Flenniken M L, Engel J C, Ruby J G, Ganernm D, Andino R, DeRisi J L: Temporal analysis of the honey bee microbiome reveals four novel viruses and seasonal prevalence of known viruses, *Nosema*, and *Crithicia*. *PLoS One* 2011, 6(6):e20656.
29. Pettis J S, vanEngelsdorp D, Johnson J, Dively G: Pesticide exposure in honey bees results in increased levels of the gut pathogen *Nosema*. *Naturwissenschaften* 2012, 99(2): 153-158.
30. Sammataro D, Gerson U, Needharn G: Parasitic mites of honey bees: Life history, implications, and impact. *Annu Rev Entomol* 2000, 45:519-548.
31. Rosenkranz P, Aumeier P, Ziegelmann B: Biology and control of *Varroa destructor*. *J Invertebr Pothol* 2010, 103 Suppl 1:S96-119.
32. Anderson D L, Trueman J W H: *Varroa jacobsoni* (Acari: Varroidae) is more than one species. *Experimental and Applied Acarology* 2000, 24(3): 165-189.
33. Kraus B, Page R E: Effect of *Varroa jacobsoni* (Mesostigmata: Varroidae) on feral *Apis melifera* (Hymenoptera: Apidae) in California. *Environ Entonmo* 1995, 24(6): 1473-1480.
34. Seeley I D: Honey bees of the Amot Forest: a population of feral colonies persisting with *Varroa destructor* in the northeastern United States. *Apidologie* 2007, 38(1): 19-29.
35. Herrmann M, Kanbar C, Engels W: Survival of honey bee (*Apis mellifera*) pupae after trypan blue staining of wounds caused by *Varroa destructor* mites or artificial perforation. *Apidologie* 2005, 36(1):107-111.
36. Ifantidis M D: Ontogenesis of the mite *Varroa jacobsoni* in worker and drone honeybee brood cells. *Journal of Apicultural Research* 1983, 22(3):200-206.
37. Martin S J: Ontogeny of the mite *Varroa jacobsoni* (Oud) in worker brood of the honeybee *Apis mellifera* (L) under natural conditions. *Experimental & Applied Acarology* 1994, 18(2):87-100.
38. Spivak M: Honey bee hygienic behavior and defense against *Varroa jacobsoni*. *Apidologie* 1996, 27(4):245-260.
39. Peng Y S, Fang Y Z, Xu S Y, Ge L S: The resistance mechanism of the Asian Honey Bee, *Apis cerana* Fabr, to an ectoparasitic mite, *Varroa jacobsoni* Oudemans. *Journal of Invertebrate Pathology* 1987, 49(1):54-60.
40. Martin S: A population model for the ectoparasitic mite *Varroa jacobsoni* in honey bee (*Apis mellifera*) colonies. *Ecol Model* 1998, 109(3):267-281.
41. Le Conte Y, Ellis M, Ritter W: *Varroa* mites and honey bee health: can *Varroa* explain part of the colony losses? *Apidologie* 2010, 41(3):353-363.
42. Boecking O, Genersch E: Varroosis—the ongoing crisis in bee keeping. *J Verbrauch Lebensm* 2008, 3(2):221-228.
43. Benoit J B, Yoder J A, Sammataro D, Zettler L W: Mycoflora and fungal vector capacity of the parasitic mite *Varroa destructor* (Mesostigmata: Varroidae) in honey bee (Hymenoptera: Apidae) colonies. *International Journal of Acarology* 2004, 30(2): 103-106.
44. De Jong D, De Jong P, Goncalves L: Weight loss and other damage to developing worker honeybees from infestation with *Varroa jacobsoni*. Journal of Apicultural Research 1982, 21:165-167.
45. Martin S J: The role of *Varroa* and viral pathogens in the collapse of honeybee colonies: a modelling approach. *Journal of Applied Ecology* 2001, 38(5): 1082-1093.
46. Genersch E, Aubert M: Emerging and re-emerging viruses of the honey bee (*Apis mellifera* L). *Vet Res* 2010, 41(6).
47. Nazzi F, Brown S P, Annoscia D, Del Piccolo F. Di Prisco G, Varricchio P, Della Vedova G, Cattonaro F, Caprio E, Pennacchio F: Synergistic parasite-pathogen interactions mediated by host immunity can drive the collapse of honeybee colonies. *PLoS Pathog* 2012, 8(6): e1002735.
48. Neumann P, Yanez O, Fries I, de Miranda J R: *Varroa* invasion and virus adaptation. *Trends Parasitol* 2012, 28(9):353-354.
49. Ryabov E V, Wood G R, Fannon J M, Moore J D, Bull J C, Chandler D, Mead A, Burroughs N, Evans D J: A virulent strain of deformed wing virus (DWV) of honeybees (*Apis mellifera*) prevails after *Varroa destructor*-mediated, or in vitro, transmission. *PLOS Pathogens* 2014, 10(6):e1004230.
50. Kuster R D, Boncristiani H F. Rueppell O: Immunogene and viral transcript dynamics during parasitic *Varroa destructor* mite infection of developing honey bee (*Apis mellifera*) pupae. *J Exp Biol* 2014, 217(Pt 10):1710-1718.
51. Yang X L, Cox-Foster D L: Impact of an ectoparasite on the immunity and pathology of an invertebrate: Evidence for host immunosuppression and viral amplification. *Proc Natl Acad Sci USA* 2005, 102(21):7470-7475.
52. Gregorc A, Evans J D, Scharf M, Ellis J D: Gene expression in honey bee (*Apis mellifera*) larvae exposed to pesticides and *Varroa* mites (*Varroa destructor*). *J Insect Physiol* 2012, 58(8):1042-1049.
53. Gregory P G, Evans J D, Rinderer T, de Guzman L: Conditional immune-gene suppression of honeybees parasitized by *Varroa* mites. *J Insect Sci* 2005, 5:7.
54. Boncristiani H F, Evans J D, Chen Y, Pettis J, Murphy C, Lopez D L, Simone-Finstrom M D, Strand M, Tarpy D R, Rueppell O: In-vitro infection of pupae with Israeli Acute Paralysis Virus suggests variation for susceptibility and disturbance of transcriptional homeostasis in honey bees (*Apis mellifera*). *PLoS One* 2013, 8(9):e73429.
55. Azzami K, Ritter W. Tautz J. Beier H: Infection of honey bees with acute bee paralysis virus does not trigger humoral or cellular immune responses. *Arch Virol* 2012, 157(4):689-702.
56. Galbraith D A, Yang X, Nifo E L, Yi S, Grozinger C, Schneider D S: Parallel epigenomic and transcriptomic responses to viral infection in honey bees (*Apis mellifera*). *PLOS Pathogens* 2015, 11(3):e1004713.
57. Carreck N L, Ball B V. Martin S J: Honey bee colony collapse and changes in viral prevalence associated with *Varroa destructor*. *Journal of Apicultural Research* 2010, 49(1):93-94.
58. Di Prisco G, Pennacchio F. Caprio E. Boncristiani H F, Evans J D, Chen Y P: *Varroa destructor* is an effective vector of Israeli acute paralysis virus in the honeybee, *Apis mellifera*. *Journal of General Virology* 2011, 92:151-155.
59. de Miranda J R, Bailey L, Ball B V, Blanchard P, Budge G E, Chejanovsky N, Chen Y-P, Gauthier L. Genersch E, de Graaf D C: Standard methods for virus research in *Apis mellifera*. *Journal of Apicultural Research* 2013, 52.
60. Martin S J, Highfield A C, Brettell L. Villalobos E M, Budge G E, Powell M, Nikaido S, Schroeder D C: Global honey bee viral landscape altered by a parasitic mite. *Science* 2012, 336(6086):1304-1306.
61. Locke B, Forsgren E, de Miranda J: Increased tolerance and resistance to virus infections: a possible factor in the survival of *Varroa destructor*. *PLoS One* 2014, 9:e99998.
62. Frazier M, Mullin C. Frazier J, Ashcraft S: What have pesticides got to do with it? *American Bee Journal* 2008, 148(6):521-524.
63. Tsigouri A D, Menkissoglu S U: Study of tau-fluvalinate persistence in honey. *Pest Manag Sci* 2001, 57:467-471.
64. Mullin C A, Frazier M, Frazier J L. Ashcraft S, Simonds R, vanEngelsdorp D, Pettis J S: High levels of miticides and agrochemicals in North American apiaries: Implications for honey bee health. *PLoS One* 2010, 5(3):e9754.
65. Johnson R M: Honey bee toxicology. *Annu Rev Entomol* 2015, 60:415-434.
66. Desneux N, Decourtye A, Delpuech J M: The sublethal effects of pesticides on beneficial arthropods. *Annu Rev Entomol* 2007, 52:81-106.
67. Wu J Y, Anelli C M, Sheppard W S: Sub-lethal effects of pesticide residues in brood comb on worker honey bee (*Apis mellifera*) development and longevity. *PLoS One* 2011, 6(2):e14720.
68. Haarmann T, Spivak M, Weaver D, Weaver B, Glenn T: Effects of fluvalinate and coumaphos on queen honey bees (Hymenoptera: Apidae) in two commercial queen rearing operations. *J Econ Entomol* 2002, 95(1):28-35.
69. Forkpah C, Dixon L R, Fahrbach S E, Rueppell O: Xenobiotic effects on intestinal stem cell proliferation in adult honey bee (*Apis mellifera* L) workers. *PLoS One* 2014, 9(3): e91180.
70. Boncristiani H, Underwood R, Schwarz R, Evans J D, Pettis J, vanEngelsdorp D: Direct effect of acaricides on pathogen loads and gene expression levels in honey bees *Apis mellifera*. *J Insect Physiol* 2012, 58(5):613-620.
71. Williamson S M, Wright G A: Exposure to multiple cholinergic pesticides impairs olfactory learning and memory in honeybees. *The Journal of Experimental Biology* 2013, 216(10):1799-1807.
72. Sammataro D, Olafson P, Guerrero F, Finley J: The resistance of *Varroa* mites (Acari: Varroidae) to Acaridies and the presence of esterase. *International Journal of Acarology* 2005, 31(1):67-74.
73. Rademacher E, Harz M: Oxalic acid for the control of varroosis in honey bee colonies-a review. *Apidologie* 2006, 37(1):98-120.
74. Calderone N W: Evaluation of formic acid and a thymol-based blend of natural products for the fall control of *Varroa jacobsoni* (Acari:Varroidae) in colonies of *Apis mellifera* (Hymenoptera:Apidae). *J Econ Entomol* 1999, 92(2):253-260.
75. Dietemann V, Pflugfelder J, Anderson D, Charrière J D, Chejanovsky N. Dainat B, De Miranda J, Delaplane K, Dillier F X, Fuch S et al: *Varroa destructor*: Research avenues towards sustainable control. *Journal of Apicultural Research* 2012, 51(1): 125-132.
76. Evans J D: Diverse origins of tetracycline resistance in the honey bee bacterial pathogen *Paenibacillus larvae*. *Journal of Invertebrate Pathology* 2003, 83(1):46-50.
77. Kochansky J, Knox D A, Feldlaufer M. Pettis J S: Screening alternative antibiotics against oxytetracycline-susceptible and -resistant *Paenibacillus larvae*. *Apidologie* 2001, 32(3):215-222.
78. Desai S D, Eu Y-J, Whyard S, Currie R W: Reduction in deformed wing virus infection in larval and adult honey bees (*Apis mellifera* L.) by double-stranded RNA ingestion. *Insect Molecular Biology* 2012, 21(4):446-455.
79. Flenniken M L, Andino R: Non-specific dsRNA-mediated antiviral response in the honey bee. *PLoS One* 2013, 8(10):e77263.
80. Hunter W, Ellis J, Hayes J, Westervelt D, Glick E, Williams M, Sela I, Maori E, Pettis J, Cox-Foster D: Large-scale field application of RNAi technology reducing Israeli acute paralysis virus disease in honey bees (*Apis mellifera*, Hymenoptera: Apidae). *PLOS Pathogens* 2010, 6(12):e1001160.
81. Maori E. Paldi N, Shafir S, Kalev H, Tsur E. Glick E, Sela I: IAPV, a bee-affecting virus associated with Colony Collapse Disorder can be silenced by dsRNA ingestion. *Insect Molecular Biology* 2009, 18(1):55-60.
82. Bourgeois A L, Rinderer T E: Genetic characterization of Russian Honey Bee stock selected for improved resistance to *Varroa destructor*. *J. Econ Entomol* 2009, 102 (3):1233-1238.
83. Spivak M, Reuter G S: Performance of hygienic honey bee colonies in a commercial apiary. *Apidologie* 1998, 29(3):291-302.
84. Harris J W: Bees with *Varroa* Sensitive Hygiene preferentially remove mite infested pupae aged <=five days post capping. *Journal of Apicultural Research* 2007, 46(3): 134-139.
85. Ibrahim A. Spivak M: The relationship between hygienic behavior and suppression of mite reproduction as honey bee (*Apis mellifera*) mechanisms of resistance to *Varroa destructor*. *Apidologie* 2006, 37(1):31-40.
86. Oxley P R, Spivak M, Oldroyd B P: Six quantitative trait loci influence task thresholds for hygienic behaviour in honeybees (*Apis mellifera*). *Mol Ecol* 2010, 19(7): 1452-1461.
87. Tsuruda J M, Harris J W, Bourgeois L, Danka R G, Hunt G J: High-resolution linkage analyses to identify genes that influence *Varroa* Sensitive Hygiene behavior in honey bees. *PLoS One* 2012, 7(11):e48276.
88. De Guzman L I, Rinderer T E, Stelzer J A, Beaman L, Delatte G, Harper C: Hygienic behavior by honey bees from far-eastern Russia. *American Bee Journal* 2002, 142(1):58-60.
89. Locke B. Fries I: Characteristics of honey bee colonies (*Apis mellifera*) in Sweden surviving *Varroa destructor* infestation. *Apidologie* 2011., 42(4):533-542.
90. Locke B, Conte Y L, Crauser D, Fries I: Host adaptations reduce the reproductive success of *Varroa destructor* in two distinct European honey bee populations. *Ecol Evol* 2012, 2(6):1144-1150.
91. Behrens D. Huang Q. Gessner C. Rosenkranz P, Frey E, Locke B, Moritz R F, Kraus F B: Three QTL in the honey bee *Apis mellifera* L. suppress reproduction of the parasitic mite *Varroa destructor*. *Ecol Evol* 2011, 1 (4):451-458.
92. Rinderer T E, Harris J W, Hunt G J, de Guzman L I: Breeding for resistance to *Varroa destructor* in North America. *Apidologie* 2010, 41(3):409-424.

93. Espinosa-Montano L G, Guzman-Novoa E, Sanchez-Albarran A, Montaldo H H, Correa-Benitez A: Comparative study of three assays to evaluate hygienic behavior in honey bee (*Apis mellifera* L.) colonies. *Veterinaria Mexico* 2008:39-54.
94. Spotter A, Gupta P, Nirnberg G, Reinsch N, Bienefeld K: Development of a 44K SNP assay focussing on the analysis of a *Varroa*-specific defence behaviour in honey bees (*Apis mellifera* camica). *Molecular Ecology Resources* 2012, 12(2):323-332.
95. Pemal S F, Sewalem A. Melathopoulos A P: Breeding for hygienic behaviour in honeybees (*Apis mellifera*) using free-mated nucleus colonies. *Apidologie* 2012, 43(4):403-416.
96. Harris J W, Danka R G, Villa J D: Changes in infestation, cell cap condition, and reproductive status of *Varroa destructor* (Mesostigmata: Varroidae) in brood exposed to honey bees with *Varroa* sensitive hygiene. *Ann Entomol Soc Am* 2012, 105(3):512-518.
97. Prisco G D, Zhang X, Pennacchio F, Caprio E, Li J, Evans J D. DeGrandi-Hoffman G, Hamilton M, Chen Y P: Dynamics of persistent and acute deformed wing virus infections in honey bees, *Apis mellifera. Viruses* 2011, 3(12):2425-2441.
98. Le Conte Y, De Vaublanc G, Crauser D, Jeanne F, Rousselle J C, Becard J M: Honey bee colonies that have survived *Varroa destructor. Apidologie* 2007, 38(6):566-572.
99. Basterfield D: *Varroa*—Still a problem in the 21st century? *Bee World* 2011, 88(1):2-4.
100. Spivak M, Downey D L: Field assays for hygienic behavior in honey bees (Hymenoptera: Apidae). *J Econ Entomol* 1998, 91(1):64-70.
101. Spivak M. Gilliam M: Hygienic behaviour of honey bees and its application for control of brood diseases and *Varroa* Part I. Hygienic behaviour and resistance to American foulbrood. *Bee World* 1998, 79(3):124-134, 169-186.
102. Swanson J A, Torto B, Kells S A, Mesce K A, Tumlinson J H, Spivak M: Odorants that induce hygienic behavior in honeybees: identification of volatile compounds in chalkbrood-infected honeybee larvae. *Journal of Chemical Ecology* 2009, 35(9): 1108-1116.
103. SchOning C, Gisder S, Geiselhardt S, Kretschmann I, Bienefeld K. Hilker M, Genersch E: Evidence for damage-dependent hygienic behaviour towards *Varroa destructor*-parasitised brood in the western honey bee, *Apis mellifera. J Exp Biol* 2012, 215(2):264-271.
104. Baracchi D, Fadda A, Turillazzi S: Evidence for antiseptic behaviour towards sick adult bees in honey bee colonies. *J Insect Physiol* 2012. 58(12):1589-1596.
105. Dietemann V, Nazzi F, Martin S J, Anderson D, Locke B, Delaplane K S, Wauquiez Q, Tannahill C, Frey E, Ziegelmann B et al: Standard methods for *Varroa* research. Journal of *Apicultural Research* 2013, 52(1): 1.09.
106. Dunkelblum E, Tan S H, Silk P J: Double-bond location in monounsaturated fatty acids by dimethyl disulfide derivatization and mass spectrometry: Application to analysis of fatty acids in pheromone glands of four lepidoptera. *Journal of chemical ecology* 1985, 11(3): 265-277.
107. Bello J E, McElfresh J S, Millar J G: Isolation and determination of absolute configurations of insect-produced methyl-branched hydrocarbons. *Proceedings of the National Academy of Sciences* 2015, 112(4): 1077-1082.
108. Vincent M, Guglielmetti G, Cassani G, Tonini C: Determination of double-bond position in diunsaturated compounds by mass spectrometry of dimethyl disulfide derivatives. *Analytical Chemistry* 1987, 59(5):694-699.
109. Aboshi T, Shimizu N. Nakajima Y, Honda Y. Kuwahara Y, Amano H. Mori N: Biosynthesis of linoleic acid in *Tyrophagus* mites (Acarina:Acaridae). *Insect Biochem Molec* 2013, 43(11):991-996.
110. Katzav-Gozansky T. Soroker V, Hefetz A, Cojocaru M, Erdmann D, Francke W: Plasticity of caste-specific Dufour's gland secretion in the honey bee (*Apis mellifera* L.). *Naturwissenschaften* 1997, 84(6):238-241.
111. Nojima S, Apperson C S, Schal C: A simple, convenient, and efficient preparative G C system that uses a short megabore capillary column as a trap. *Journal of chemical ecology* 2008, 34(3):418-428.
112. Richard F J, Aubert A. Grozinger C M: Modulation of social interactions by immune stimulation in honey bee. *Apis mellifera*, workers. *BMC Biol* 2008, 6:50.
113. Rueppell O, Hayworth M K. Ross N P: Altruistic self-removal of health-compromised honey bee workers from their hive. *Journal of Evolutionary Biology* 2010, 23:1538-1546.
114. Torto B, Carroll M J, Duehl A, Fombong A T, Gozansky T K, Nazzi F, Soroker V. Teal P E: Standard methods for chemical ecology research in *Apis mellifera. Journal of Apicultural Research* 2013, 52(4).
115. Böröczky K, Wada-Katsumata A. Batchelor D. Zhukovskaya M, Schal C: Insects groom their antennae to enhance olfactory acuity. *Proceedings of the National Academy of Sciences* 2013, 110(9):3615-3620.
116. Eliyahu D, Nojima S, Santangelo R G, Carpenter S. Webster F X, Kiemle D J, Gemeno C, Leal W S, Schal C: Unusual macrocyclic lactone sex pheromone of *Parcoblatta lata*, a primary food source of the endangered red-cockaded woodpecker. *Proceedings of the National Academy of Sciences* 2012, 109(8):E490-E496.
117. Youngsteadt E, Nojima S. Haberlein C, Schulz S, Schal C: Seed odor mediates an obligate ant-plant mutualism in Amazonian rainforests. *Proceedings of the National Academy of Sciences* 2008, 105(12):4571-4575.
118. Nojima S, Schal C, Webster F X, Santangelo R G, Roelofs W L: Identification of the sex pheromone of the German cockroach, *Blattella germanica. Science* 2005. 307(5712):1104-1106.
119. Mant J, Brändli C, Vereecken N J, Schulz C M, Francke W. Schiestl F P: Cuticular hydrocarbons as sex pheromone of the bee *Colletes cunicularius* and the key to its mimicry by the sexually deceptive orchid, *Ophrys exaltata. Journal of chemical ecology* 2005, 31(8): 1765-1787.
120. Rosenkranz P. Tewarson N, Singh A. Engels W: Differential hygienic behavior towards *Varroa jacobsoni* in capped worker brood of *Apis cerana* depends on alien scent adhering to the mites. *Journal of Apicultural Research* 1993, 32(2):89-93.
121. Furman D, Jojic V, Sharma S, Shen-Orr S S. L. Angel C J, Onengut-Gumuscu S. Kidd B A. Maecker H T. Concannon P, Dekker C L et al: Cytomegalovirus infection enhances the immune response to influenza. *Science Translational Medicine* 2015, 7(281):281 ra243.
122. Mondet F, de Miranda J R, Kretzschmar A, Le Conte Y. Mercer A R: On the front line: quantitative virus dynamics in honeybee (*Apis mellifera* L.) colonies along a new expansion front of the parasite *Varroa destructor. PLOS Pathogens* 2014, 10(8):e1004323.

123. Podgwaite J D, Mazzone H M: Latency of insect viruses. *Advances in Virus Research* 1986, 31:293-320.
124. Evans J D: Beepath: an ordered quantitative-PCR array for exploring honey bee immunity and disease. *J Invertebr Pathol* 2006, 93(2): 135-139.
125. Williams G R, Alaux C, Costa C. Csaki T. Doublet V. Eisenhardt D, Fries I. Kuhn R. McMahon D P, Medrzycki P et al: Standard methods for maintaining adult *Apis mellifera* in cages under in vitro laboratory conditions. *Journal of Apicultural Research* 2013, 52(1).
126. Andersen C L, Jensen J L, Omrntoft T F: Normalization of real-time quantitative reverse transcription-PCR data: a model-based variance estimation approach to identify genes suited for normalization, applied to bladder and colon cancer data sets. *Cancer research* 2004, 64(15): 5245-5250.
127. Severson D, Erickson Jr E, Williamson J, Aiken J: Heat stress induced enhancement of heat shock protein gene activity in the honey bee (*Apis mellifera*). *Experientia* 1990, 46(7):737-739.
128. Otvos L, O I, Rogers M E, Consolvo P J, Condie B A, Lovas S, Bulet P, Blaszczyk-Thurin M: Interaction between heat shock proteins and antimicrobial peptides. *Biochemistry* 2000, 39(46):14150-14159.
129. Coelho J R: Heat transfer and body temperature in honey bee (Hymenoptera: Apidae) drones and workers. *Environ Entomol* 1991, 20(6): 1627-1635.
130. Alaux C, Dantec C, Parrinello H, Le Conte Y: Nutrigenomics in honey bees: digital gene expression analysis of pollen's nutritive effects on healthy and *Varroa*-parasitized bees. *BMC Genomics* 2011, 12:496.
131. Wang Y, Kaftanoglu O, Fondrk M K, Page R E: Nurse bee behaviour manipulates worker honeybee (*Apis mellifera* L.) reproductive development. *Anim Behav* 2014, 92:253-261.
132. Johnson R M, Ellis M D, Mullin C A, Frazier M: Pesticides and honey bee toxicity—USA. *Apidologie* 2010, 41(3):312-331.
133. Collins A M, Pettis J S, Wilbanks R, Feldlaufer M F: Performance of honey bee (*Apis mellifera*) queens reared in beeswax cells impregnated with coumaphos. *Journal of Apicultural Research* 2004, 43(3): 128-134.
134. Dahlgren L. Johnson R M, Siegfried B D, Ellis M D: Comparative toxicity of acaricides to honey bee (Hymenoptera: Apidae) workers and queens. *J Econ Entomol* 2012, 105(6): 1895-1902.
135. Kanbar G. Engels W: Ultrastructure and bacterial infection of wounds in honey bee (*Apis mellifera*) pupae punctured by *Varroa* mites. *Parasitol Res* 2003, 90(5): 349-354.
136. Arrese E L, Soulages J L: Insect fat body: energy, metabolism, and regulation. *Annu Rev Entomol* 2010, 55:207-225.
137. Gillespie and J P, Kanost M R, Trenczek T: Biological mediators of insect immunity. *Annu Rev Entomol* 1997, 42(1):611-643.
138. Trapnell C, Pachter L. Salzberg S L: TopHat: discovering splice junctions with RNA-*Seq. Bioinformatics* 2009, 25(9):1105-1111.
139. Trapnell C, Williams B A, Pertea G, Mortazavi A, Kwan G, van Baren M J, Salzberg S L, Wold B J, Pachter L: Transcript assembly and quantification by RNA-Seq reveals unannotated transcripts and isoform switching during cell differentiation. *Nat Biotechnol* 2010, 28(5): 511-515.
140. Trapnell C, Roberts A, Goff L, Pertea G. Kim D, Kelley D R, Pimentel H, Salzberg S L, Rinn J L, Pachter L: Differential gene and transcript expression analysis of RNA-seq experiments with TopHat and Cufflinks. *Nat Protoc* 2012, 7(3):562-578.
141. Mortazavi A, Williams B A, McCue K. Schaeffer L, Wold B: Mapping and quantifying mammalian transcriptomes by RNA-Seq. *Nat Methods* 2008, 5(7):621-628.
142. Pepke S, Wold B, Mortazavi A: Computation for ChIP-seq and RNA-seq studies. *Natl Methods* 2009, 6(11 Suppl):S22-32.
143. Elsik C G, Worley K C, Bennett A K, Beye M, Camara F, Childers C P, de Graaf D C, Debyser G, Deng J, Devreese B et al: Finding the missing honey bee genes: lessons learned from a genome upgrade. *BMC Genomics* 2014, 15:86.
144. Langmead B, Salzberg S L: Fast gapped-read alignment with Bowtie 2. *Nat Methods* 2012, 9(4):357-359.
145. Anders S, Pyl P T, Huber W: HTSeq-A Python framework to work with high-throughput sequencing data. *Bioinformatics* 2014:btu638.
146. Huang A S, Baltimore D: Defective viral particles and viral disease processes. *Nature* 1970, 226:325-327.
147. Li D, Lott W B, Lowry K, Jones A, Thu H M, Aaskov J: Defective interfering viral particles in acute dengue infections. *PLoS One* 2011, 6(4):e19447.
148. Hurd H: Manipulation of medically important insect vectors by their parasites. *Annu Rev Entomol* 2003, 48(1): 141-161.
149. Chen Y P, Siede R: Honey bee viruses. *Adv Virus Res* 2007, 70:33-80.
150. Granberg F, Vicente-Rubiano M, Rubio-Guerri C, Karlsson O E, Kukielka D. Belák S, Sánchez-Vizcaino J M: Metagenomic detection of viral pathogens in spanish honeybees: co-infection by aphid lethal paralysis, Israel acute paralysis and lake sinai viruses. *PLoS One* 2013, 8(2):e57459.
151. Comman R S, Boncristiani H. Dainat B, Chen Y, Weaver D, Evans J D: Population-genomic variation within RNA viruses of the Western honey bee, *Apis mellifera*, inferred from deep sequencing. *BMC Genomics* 2013, 14(1): 154.
152. Garbian Y, Maori E, Kalev H. Shafir S, Sela I: Bidirectional transfer of RNAi between honey bee and *Varroa destructor: Varroa* gene silencing reduces *Varroa* population. *PLOS Pathogens* 2012, 8(12):e1003035.
153. Aumeier P., P. Rosenkranz. (2001) Scent or movement of *Varroa destructor* mites does not elicit hygienic behaviour by Africanized and Camiolan honey bees. Apidologie 32(3): 253-264.
154. Berry J. (January 2009) Pesticides, Bees and Wax: An Unhealthy, Untidy Mix. Bee Culture: 33-35.
155. Boecking O., K. Bienefeld, W. Drescher. (2000) Heritability of the *Varroa*, a specific hygienic behaviour in honey bees (Hymenoptera: Apidae). Journal of Animal Breeding and Genetics 117(6): 417-424.
156. Boecking O., W. Drescher. (1992) The removal response of *Apis mellifera* L. colonies to brood in wax and plastic cells after artificial and natural infestation with *Varroa jacobsoni* Oud. and to freeze-killed brood. Experimental and Applied Acarology 16(4): 321-329.
157. Bogdanov S. (2006) Contaminants of bee products. Apidologie 37: 1-18.
158. Bostanian N. J., V. Preedy, R. Watson. (2004) Pesticide toxicology: mode of action, residues in fruit crops, and risk assessment. Reviews in Food and Nutrition Toxicity 2: 215-268.
159. Bowen-Walker P., S. Martin, A. Gunn. (1999) The Transmission of Deformed Wing Virus between Honeybees (*Apis mellifera* L.) by the Ectoparasitic Mite *Varroa jacobsoni* Oud. Journal of Invertebrate Pathology 73(1): 101-106.
160. Calderon R. A., N. Fallas, L. G. Zamora, J. W. van Veen. L. A. Sanchez. (2009) Behavior of *Varroa* mites in worker brood cells of Africanized honey bees. Experimental and Applied Acarology 49(4): 329-338.
161. Chen Y., J. S. Pettis, J. D. Evans, M. Kramer, M. F. Feldlaufer. (2004) Transmission of Kashmir bee virus by the ectoparasitic mite *Varroa destructor*. Apidologie 35: 441-448.
162. Claudianos C., H. Ranson, R Johnson, S. Biswas, M. Schuler, et al. (2006) A deficit of detoxification enzymes: pesticide sensitivity and environmental response in the honeybee. Insect Molecular Biology 15(5): 615-636.
163. Dekeyser M. A., R. G. H. Downer. (1994) Biochemical and physiological targets for miticides. Pesticide Science 40(2): 85-101.
164. Edwards D. (2005) Reregistration Eligibility Decision for Tau-fluvalinate, in: Environmental Protection Agency, S. R. and R. D. (Ed.), pp. 1-76.
165. Frey E., R. Odemer. T. Blum, P. Rosenkranz. (2013) Activation and interruption of the reproduction of *Varroa destructor* is triggered by host signals (*Apis mellifera*). Journal of Invertebrate Pathology.
166. Goode K., Z. Huber, K. A. Mesce, M. Spivak. (2006) Hygienic behavior of the honey bee (*Apis mellifera*) is independent of sucrose responsiveness and foraging ontogeny. Hormones and Behavior 49(3): 391-397.
167. Harbo J. R., J. W. Harris. (2001) Resistance to *Varroa destructor* (Mesostigmata: Varroidae) when mite-resistant queen honey bees (Hymenoptera: Apidae) were free-mated with unselected drones. Journal of Economic Entomology 94(6): 1319-1323.
168. Harbo J. R., J. W. Harris. (2009) Responses to *Varroa* by honey bees with different levels of *Varroa* Sensitive Hygiene. Journal of Apicultural Research 48(3): 156-161.
169. Harris, J. W. (2008) Effect of brood type on *Varroa*-sensitive hygiene by worker honey bees (Hymenoptera: Apidae). Annals of the Entomological Society of America 101:1137-1144.
170. Ibrahim A., G. S. Reuter, M. Spivak. (2007) Field trial of honey bee colonies bred for mechanisms of resistance against *Varroa destructor*. Apidologie 38(1): 67-76.
171. Imdorf A. C., J D; Kilchemann, V: Bogdanov, S; Fluri, P. (2003) Alternative strategy in central Europe for the control of *Varroa destructor* in honey bee colonies. Apiacta 38: 258-278.
172. Johnson R. M., H. S. Pollock, M. R. Berenbaum. (2009) Synergistic interactions between in-hive miticides in *Apis mellifera*. Journal of Economic Entomology 102(2): 474-479.
173. Kanga L. H. B., A. B. Somorin. (2012) Susceptibility of the small hive beetle, *Aethina tunida* (Coleoptera: Nitidulidae), to insecticides and insect growth regulators. Apidologie 43: 95-102.
174. Martel A. C., S. Zeggane. C. Aurieres, P. Drajnudel, J. P. Faucon, et al. (2007) Acaricide residues in honey and wax after treatment of honey bee colonies with Apivar or Asuntol 50. Apidologie 38(6): 534-544.
175. Masterman R., R. Ross, K. Mesce, M. Spivak. (2001) Olfactory and behavioral response thresholds to odors of diseased brood differ between hygienic and non-hygienic honey bees (*Apis mellifera* L.). Journal of Comparative Physiology A: Neuroethology. Sensory, Neural, and Behavioral Physiology 187(6): 441-452.
176. Parker R., M. M. Guama. A. Melathopoulos, K. M. Moon, R. White, et al. (2012) Correlation of proteome-wide changes with social immunity behaviors provides insight into resistance to the parasitic mite, *Varroa destructor*, in the honey bee (*Apis mellifera*). Genome Biology 13(9): R81.
177. Pettis J. S., A. M. Collins, R. Wilbanks, M. F. Feldlaufer. (2004) Effects of coumaphos on queen rearing in the honey bee, *Apis mellifera*. Apidologie 35(6): 605-610.
178. Sammataro D., P. Untalan, F. Guerrero, J. Finley. (2005) The resistance of *Varroa* mites (Acari: Varroidae) to acaricides and the presence of esterase. International Journal of Acarology 31(1): 67-74.
179. Schoning C., S. Gisder, S. Geiselhardt, I. Kretschmann, K. Bienefeld, et al. (2012) Evidence for damage-dependent hygienic behaviour towards *Varroa destructor*-parasitised brood in the western honey bee, *Apis mellifera*. The Journal of Experimental Biology 215(2): 264-271.
180. Shelton D. R., C. J. Somich. (1988) Isolation and characterization of coumaphos-metabolizing bacteria from cattle dip. Applied and Environmental Microbiology 54(10): 2566-2571.
181. Spivak M., E. Mader, M. Vaughan, N. H. Euliss Jr. (2011) The Plight of the Bees. Environ. Sci. Technol 45(1): 34-38.
182. Spivak M., G. S. Reuter. (2001) Resistance to American foulbrood disease by honey bee colonies *Apis mellifera* bred for hygienic behavior. Apidologie 32(6): 555-565.
183. Spotter A., P. Gupta, G. Numberg, N. Reinsch, K. Bienefeld. (2012) Development of a 44K SNP assay focusing on the analysis of a *Varroa*-specific defence behaviour in honey bees (*Apis mellifera* camica). Molecular Ecology Resources 12: 323-332.
184. vanEngelsdorp D., J. Hayes, R. M. Underwood, J. Pettis. (2008) A survey of honey bee colony losses in the U S, fall 2007 to spring 2008. PLoS One 3(12): e4071.
185. Wallner K. (1999) Varroacides and their residues in bee products. Apidologie 30: 235-248.
186. Dade H A (1994, 2009) Anatomy and dissection of the honey bee (revised edition). International Bee Research Association, Cardiff, U K.
187. Fakhimzadeh K (2001) Effectiveness of confectioner sugar dusting to knock down *Varroa destructor* from adult honey bees in laboratory trials. Apidologie 32: 139-148.
188. Sokal R R & Rohlf F J (1995) The principles and practice of statistics in biological research. W H Freeman and Co., New York.
189. Genersch E., W. von der Ohe, H. Kaatz, A. Schroeder, C. Otten, et al. (2010) The German bee monitoring project: a long term study to understand periodically high winter losses of honey bee colonies. Apidologie 41(3): 332-352.
190. Berenbaum M., P. Bernhardt, S. Buchmann, N. Calderone, P. Goldstein, et al. (2007) Status of pollinators in North America, The National Academies Press, Washington, D.C.
191. Aizen M. A., L. D. Harder. (2009) The global stock of domesticated honey bees is growing slower than agricultural demand for pollination. Current biology 19(11): 915-918.
192. vanEngelsdorp D., D. Caron. J. Haves, R. Underwood, M. Henson, et al. (2012) A national survey of managed honey bee 2010-11 winter colony losses in the USA: results from the Bee Informed Partnership. Journal of Apicultural Research 51(1): 115-124.
193. Spleen A. M., E. J. Lengerich, K. Rennich, D. Caron, R. Rose, et al. (2013) A national survey of managed honey bee 2011-12 winter colony losses in the United States: results from the Bee Informed Partnership. Journal of Apicultural Research 52(2): 44-53.
194. Steinhauer N. A., K. Rennich, M. E. Wilson, D. M. Caron, E. J. Lengerich, et al. (2014) A national survey of managed honey bee 2012-2013 annual colony losses in the USA: results from the Bee Informed Partnership. Journal of Apicultural Research 53(1): 1-18.
195. Lee K. V., N. Steinhauer, K. Rennich, M. E. Wilson, D. R. Tarpy, et al. (2015) A national survey of managed honey bee 2013-2014 annual colony losses in the USA. Apidologie 46(3): 292-305.
196. Kirrane M. J., L. I. De Guzman, T. E. Rinderer, A. M. Frake, J. Wagnitz, et al. (2011) Asynchronous development of Honey Bee host and *Varroa destructor* (Mesostigmata: Varroidae) influences reproductive potential of mites. Journal of economic entomology 104(4): 1146-1152.
197. Carreck N. L. (2011) *Varroa*. Still a problem in the 21st century? International Bee Research Association.
198. Ifantidis M. D. (1988) Some aspects of the process of *Varroa jacobsoni* mite entrance into honey bee (*Apis mellifera*) brood cells. Apidologie 19(4): 387-396.
199. Schatton-Gadelmayer K., W. Engels. (1988) Blood proteins and body weight of newly-emerged worker honeybees with different levels of parasitization of brood mites. *Entomolgia Generalis* 14: 93-101.
200. D'Aubeterre J. P., D. D. Myrold, L. A. Royce, P. A. Rossignol. (1999) A scientific note of an application of isotope ratio mass spectrometry to feeding by the mite, *Varroa jacobsoni* Oudemans, on the honeybee, *Apis mellifera* L. Apidologie 30(4): 351-352.
201. Amdam G. V., K. Hartfelder, K. Norberg, A. Hagen, S. W. Omholt. (2004) Altered physiology in worker honey bees (Hymenoptera: Apidae) infested with the mite *Varroa destructor* (Acari: Varroidae): a factor in colony loss during overwintering? Journal of Economic Entomology 97(3): 741-747.
202. Garedew A., E. Schmolz, I. Lamprecht. (2004) The energy and nutritional demand of the parasitic life of the mite *Varroa destructor*. Apidologie 35: 419-430.
203. Sylvester H. A., R. P. Watts, L. I. Guzman, J. A. Stelzer, T. E. Rinderer. (1999) Varroa in the mating yard. 11. The effects of *Varroa* and fluvalinate on drone mating competitiveness. American Bee Journal 139.
204. Burley L. M., R. D. Fell, R. G. Saacke. (2008) Survival of honey bee (Hymenoptera: Apidae) spermatozoa incubated at room temperature from drones exposed to miticides. Journal of economic entomology 101(4): 1081-1087.
205. Millar J G: Chemical synthesis of insect cuticular hydrocarbons. Insect hydrocarbons: biology, biochemistry, and chemical ecology. Cambridge University Press, Cambridge 2010:163-186.
206. Carlson D, Mackley J: Polyunsaturated hydrocarbons in the stable fly. *Journal of chemical ecology* 1985, 11:1485-1496.
207. Ginzel M D, Moreira J A, Ray A M, Millar J G, Hanks L M: (Z)-9-Nonacosene—major component of the contact sex pheromone of the beetle *Megacyllene caryae*. *Journal of chemical ecology* 2006, 32:435-451.
208. Kuster R D, Boncristiani H F, Rueppell O: Immunogene and viral transcript dynamics during parasitic *Varroa destructor* mite infection of developing honey bee (*Apis mellifera*) pupae. *Journal of Experimental Biology* 2014, 217:1710-1718.
209. Delaplane K S, van der Steen J, Guzman-Novoa E: Standard methods for estimating strength parameters of *Apis mellifera* colonies. *Journal of Apicultural Research* 2013, 52:1-12.
210. De Smet L, Ravoet J, de Miranda J R, Wenseleers T, Mueller M Y, Moritz R F, De Graaf D C: BeeDoctor, a versatile MLPA-based diagnostic tool for screening bee viruses. *PLoS One* 2012, 7:e47953.
211. Mondet, F. et al. Specific Cues Associated With Honey Bee Social Defence against *Varroa destructor* Infested Brood. *Sci. Rep.* 6, 25444 (2016).
212. Le Conte, Y., Arnold, G., Trouiller, J., Masson, C. & Chappe, B. Identification of a brood pheromone in honeybees. Naturwissenschaften 77, 334-336 (1990).
213. Slessor, K., Winston, M. & Conte, Y. Pheromone communication in the honeybee (*Apis mellifera* L.). *J. Chem. Ecol.* 31, 2731-2745 (2005).
214. Francesco Nazzi, Giorgio Della Vedova, Mauro D'Agaro. A semiochemical from brood cells infested by *Varroa destructor* triggers hygienic behaviour in *Apis mellifera*. Apidologie, Springer Verlag, 2004, 35 (1), pp. 65-70.
215. Sonnet, P. E., Uebel, E. C., Lusby, W. R., Schwarz, M., and Miller, R. W. Sex pheromone of the stable fly. Identification, synthesis and evaluation of alkenes from female stable flies. *J. Chem. Ecol.*, 5, 353-351. 1979.
216. Kimura. T., Carlson, D. A., and Mori, K. 2001. Pheromone synthesis. Part 211. Synthesis of all of the stereoisomers of 13,17-dimethyl-1-tritriacontene and 13,17-dimethyl-1-pentatriacontene: the contact sex pheromone components of the female tsetse fly, *Glossina austeni*. European J. Org. Chem. 3385-3390.

All publications, patent applications, patents, and other references mentioned in the specification are indicative of the level of those skilled in the art to which the presently disclosed subject matter pertains. All publications, patent applications, patents, and other references are herein incorporated by reference to the same extent as if each individual publication, patent application, patent, and other reference was specifically and individually indicated to be incorporated by reference. It will be understood that, although a number of patent applications, patents, and other references are referred to herein, such reference does not constitute an admission that any of these documents forms part of the common general knowledge in the art.

Although the foregoing subject matter has been described in some detail by way of illustration and example for purposes of clarity of understanding, it will be understood by those skilled in the art that certain changes and modifications can be practiced within the scope of the appended claims.

What is claimed:

1. A method of inducing hygienic behavior in honey bees, the method comprising contacting hive cells with a composition comprising a tritriacontene and an agriculturally acceptable diluent or carrier, wherein the tritriacontene is in an effective amount for inducing hygienic behavior in honey bees.

2. The method of claim 1, wherein the tritriacontene is of the structure:

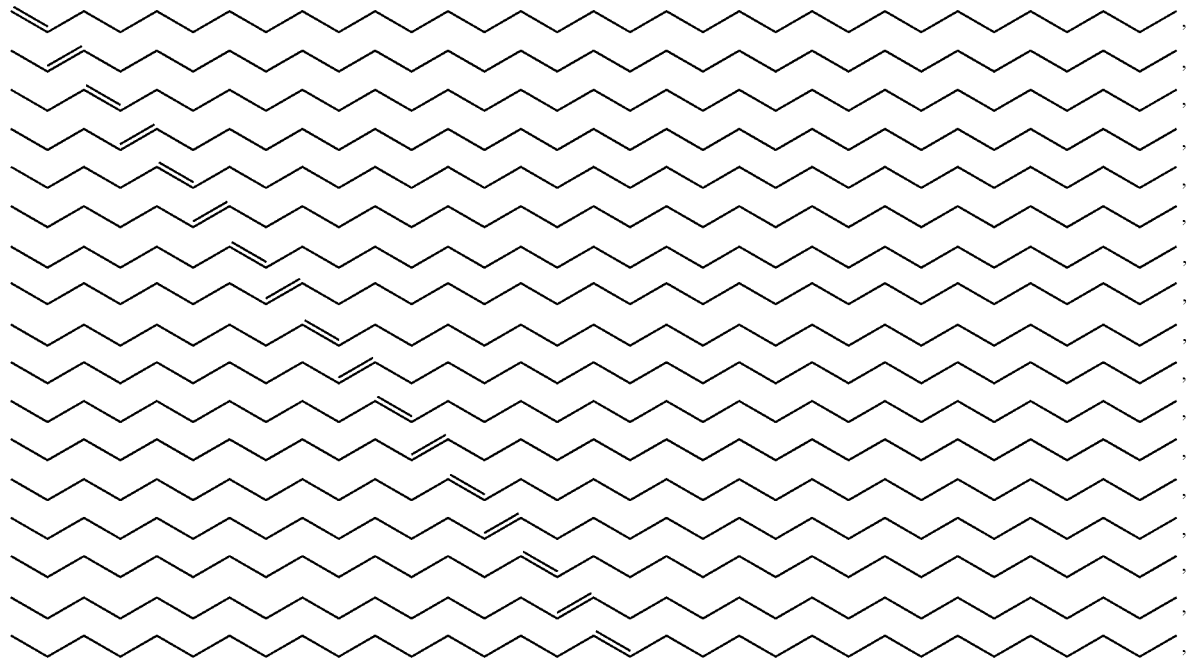

or agriculturally acceptable derivatives thereof.

3. The method of claim 1, wherein the tritriacontene is a cis-isomer.

4. The method of claim 3, wherein the tritriacontene is of the structure:

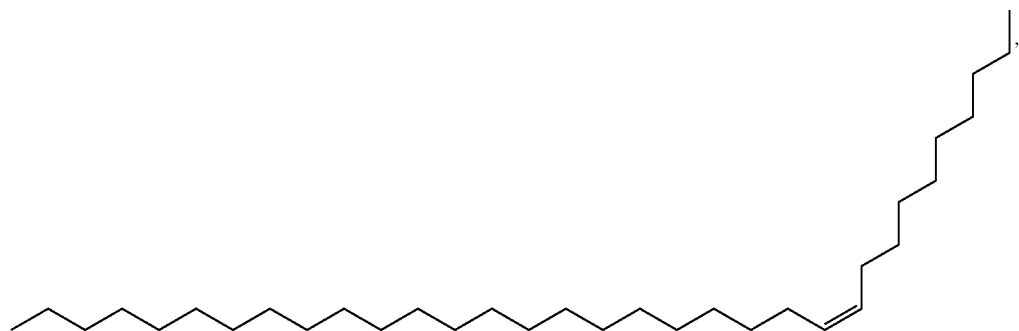 [SMILES: CCCCCCCCC/C=C\CCCCCCCCCCCCCCCCCCCCCC]

or an agriculturally acceptable derivative thereof.

5. The method of claim 1, wherein the hygienic behavior comprises eating diseased brood, eating diseased honey bees, removing diseased brood from hive cells, removing diseased honey bees from hive cells, removing pests or parasites, uncapping hive cells, or uncapping and recapping hive cells.

6. The method of claim 1, wherein the hygienic behavior results in survival of a honey bee colony.

7. The method of claim 1, wherein the hygienic behavior results in suppression of mite reproduction, decreased mite survival, or suppression of a mite infestation.

8. The method of claim 1, wherein the hive cells are capped hive cells or uncapped hive cells.

9. The method of claim 1, wherein the hive cells are worker-brood cells, drone-brood cells, or queen bee cells.

10. The method of claim 5, wherein the diseased brood are eggs, larvae, or pupae.

11. The method of claim 5, wherein the diseased brood or diseased honey bees are infested with pests or parasites: infected with a pathogen: or damaged.

12. The method of claim 5 or 11, wherein the pests or parasites are mites, wax moths, or small hive beetles.

13. The method of claim 11, wherein the pathogen is a bacterium, a fungus, or a virus.

14. The method of claim 13, wherein the pathogen causes chalkbrood, American foulbrood, or European foulbrood.

15. The method of claim 11, wherein the damaged diseased brood or damaged diseased honey bees are health-compromised due to exposure to toxic chemicals.

16. The method of claim 7 or 12, wherein the mites are mites of the genus *Varroa*.

17. The method of claim 16, wherein the mites are mites of the species *Varroa destructor* or *Varroa jacobsoni*.

18. The method of claim 1, wherein the contacting of the hive cells is on one or more days after the hive cells are capped.

19. The method of claim 1, wherein the contacting of the hive cells is on one or more days before the hive cells are capped.

20. A method for selecting one or more honey bee(s) exhibiting hygienic behavior comprising:
   a) applying a tritriacontene composition to a set of hive cells;
   b) performing an assay to identify a hygienic colony, wherein the assay comprises exposing the set of hive cells to a test colony; and
   c) selecting one or more honey bee(s) from an identified hygienic colony, wherein the selected one or more honey bee(s) exhibit hygienic behavior.

21. The method of claim 20, wherein the set of hive cells contains a diseased brood, diseased honey bees, or pests or parasites.

22. The method of claim 20, wherein the tritriacontene composition comprises a tritriacontene and an agriculturally acceptable diluent or carrier, wherein the tritriacontene is in an effective amount for inducing hygienic behavior in honey bees.

23. The composition of claim 22, wherein the tritriacontene is of the structure:

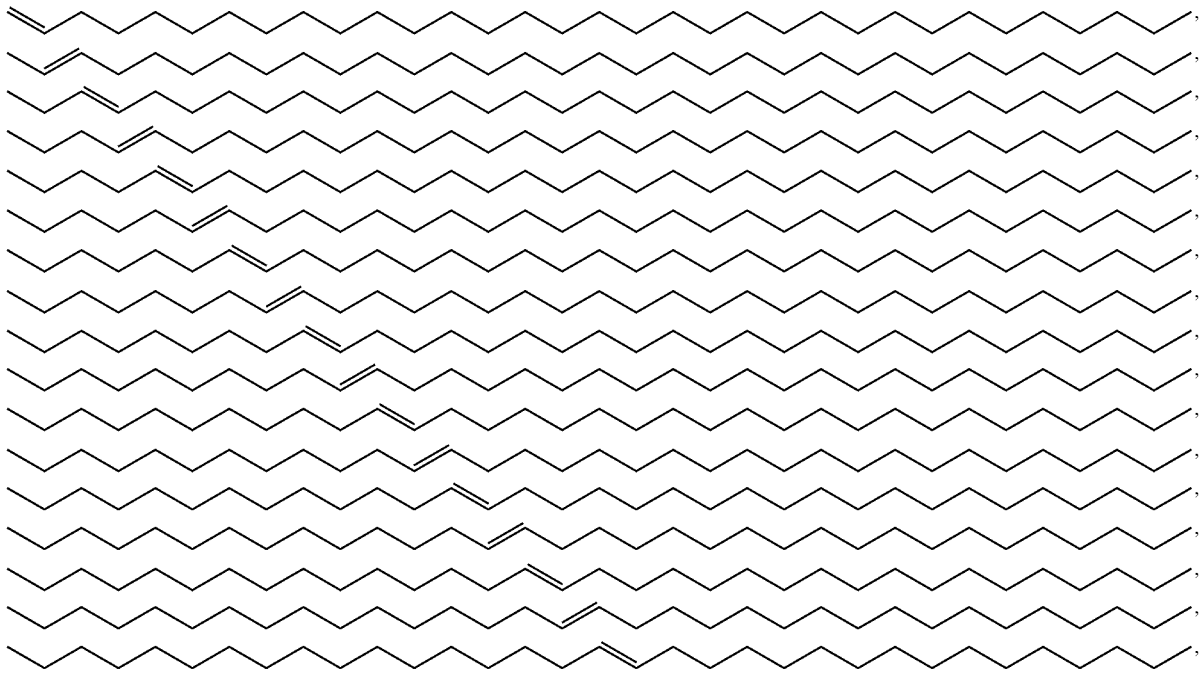

or agriculturally acceptable derivatives thereof.

24. The method of claim 22, wherein the tritriacontene is a cis-isomer.

25. The method of claim 24, wherein the tritriacontene is of the structure:

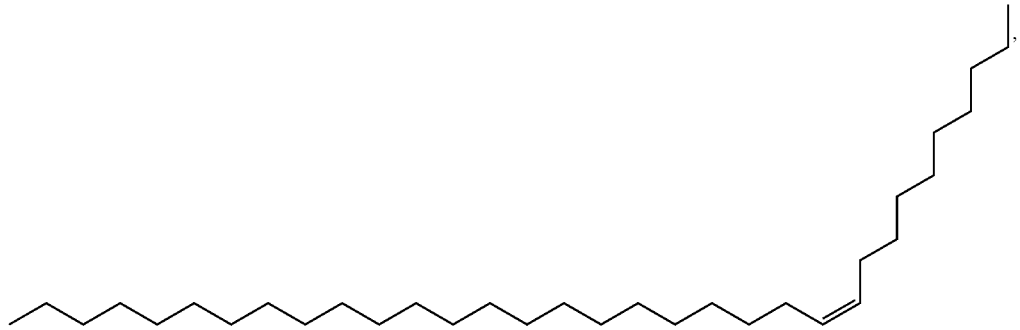 [SMILES: CCCCCCCCC/C=C\CCCCCCCCCCCCCCCCCCCCCC]

or an agriculturally acceptable derivative thereof.

26. The method of claim 20, wherein the selected honey bee(s) is a queen bee or a drone bee.

27. The method of claim 21, wherein the assay further comprises:
   i. determining an amount of emptied hive cells in the set of hive cells; and
   ii. identifying a hygienic colony, wherein a test colony is a hygienic colony if at least 90% of the set of hive cells are emptied.

28. The method of claim 27, wherein the emptied hive cells have no eggs, larvae, or pupae; or contain partially eaten larvae or pupae.

29. The method of claim 27, wherein the emptied hive cells are capped hive cells or uncapped hive cells.

30. The method of claim 20, wherein the hive cells are capped hive cells and the assay further comprises:
   i. determining the amount of uncapped hive cells in the set of capped hive cells; and
   ii. identifying a hygienic colony, wherein a test colony is a hygienic colony if at least 90% of the set of capped hive cells are uncapped.

31. The method of claim 30, wherein the capped hive cells are empty.

32. The method of claim 20, wherein the hive cells are capped hive cells and the assay further comprises:
   i. determining the amount of hive cells uncapped and subsequently recapped in the set of capped hive cells; and
   ii. identifying a hygienic colony, wherein a test colony is a hygienic colony if at least 90% of the set of capped hive cells are uncapped and subsequently recapped.

33. The method of claim 32, wherein the capped hive cells are empty.

34. The method of claim 26, further comprising d) mating a selected honey bee with one or more honey bee(s) from at least one separately identified hygienic colony to produce offspring.

35. The method of claim 26, wherein a queen bee is selected and mated: (a) naturally with one or more drones from at least one separately identified hygienic colony; or (b) artificially inseminated with semen from one or more drones from at least one separately identified hygienic colony.

36. The method of claim 34, further comprising:
   e) raising the offspring,
   f) applying a tritriacontene composition to a second set of hive cells,
   g) performing a second assay to identify whether the raised offspring is a hygienic colony, wherein the second assay comprises exposing the second set of hive cells to the raised offspring, and
   h) selecting one or more honey bee(s) from an identified hygienic colony, wherein the selected one or more honey bee(s) exhibit hygienic behavior.

37. The method of claim 36, wherein the second set of hive cells contains a diseased brood, diseased honey bees, or pests or parasites.

38. The method of claim 34, wherein at least one separately identified hygienic colony was bred or identified by a method comprising the steps of claim 15.

39. The method of claim 34, wherein at least one separately identified hygienic colony was bred or identified by a method based on freeze-killed brood, suppression of mite reproduction, or removal of damaged brood.

40. The method of claim 37, wherein the second assay further comprises:
   i. determining the amount of emptied hive cells in the second set of hive cells; and
   ii. identifying a hygienic colony, wherein the raised offspring is a hygienic colony if at least 90% of the second set of hive cells are emptied.

41. The method of claim 36, wherein the hive cells are capped hive cells and the second assay further comprises:
   i. determining an amount of uncapped hive cells in the second set of capped hive cells; and
   ii. identifying a hygienic colony, wherein the raised offspring is a hygienic colony if at least 90% of the second set of capped hive cells are uncapped.

42. The method of claim 41, wherein the capped hive cells are empty.

43. The method of claim 36, wherein the hive cells are capped hive cells and the second assay further comprises:
   i. determining an amount of hive cells uncapped and subsequently recapped in the second set of capped hive cells; and
   ii. identifying a hygienic colony, wherein the raised offspring is a hygienic colony if at least 90% of the second set of capped hive cells are uncapped and subsequently recapped.

44. The method of claim 43, wherein the capped hive cells are empty.

45. A method for assessing the degree of hygienic behavior within a honey bee colony comprising:
   a. applying a tritriacontene composition to a set of hive cells;
   b. exposing the set of hive cells to a honey bee colony; and
   c. determining the amount of emptied hive cells in the set of hive cells;
wherein a higher amount of the set of hive cells that are emptied is associated with a greater degree of hygienic behavior.

46. The method of claim 45, wherein the set of hive cells contains a diseased brood, diseased honey bees, or pests or parasites.

47. The method of claim 45, wherein the tritriacontene composition comprises a tritriacontene and an agriculturally acceptable diluent or carrier, wherein the tritriacontene is in an effective amount for inducing hygienic behavior in honey bees.

48. The method of claim 47, wherein the tritriacontene is of the structure:

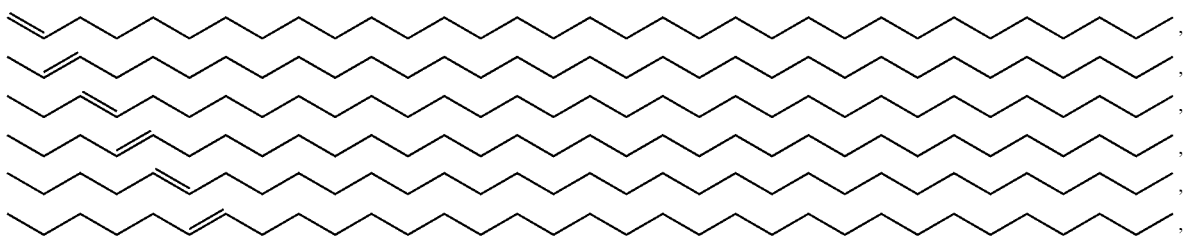

-continued

or agriculturally acceptable derivatives thereof.

49. The method of claim 47, wherein the tritriacontene is a cis-isomer.

50. The method of claim 49, wherein the tritriacontene is of the structure:

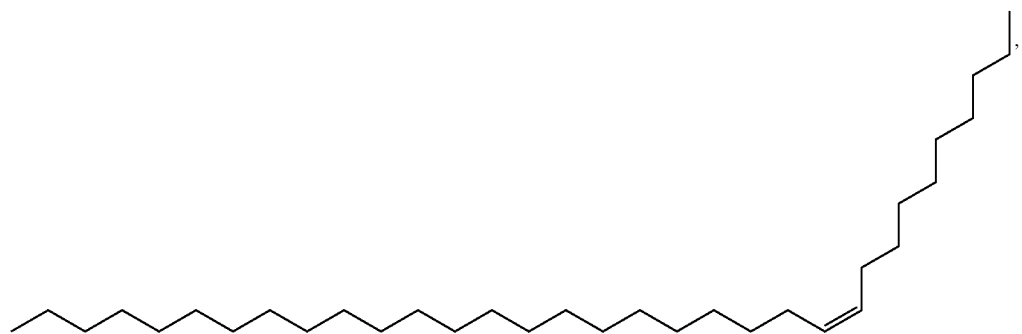 [SMILES: CCCCCCCCC/C=C\CCCCCCCCCCCCCCCCCCCCCC]

or an agriculturally acceptable derivative thereof.

51. A method for assessing the degree of hygienic behavior within a honey bee colony comprising:
 a. applying a tritriacontene composition to a set of capped hive cells;
 b. exposing the set of capped hive cells to a honey bee colony; and
 c. determining the amount of uncapped hive cells in the set of capped hive cells;
wherein a higher amount of the set of hive cells that are uncapped is associated with a greater degree of hygienic behavior.

52. The method of claim 51, wherein the set of capped hive cells contains a diseased brood, diseased honey bees, or pests or parasites.

53. The method of claim 51, wherein the set of capped hive cells is empty.

54. The method of claim 51, wherein the tritriacontene composition comprises a tritriacontene and an agriculturally acceptable diluent or carrier, wherein the tritriacontene is in an effective amount for inducing hygienic behavior in honey bees.

55. The method of claim 54, wherein the tritriacontene is of the structure:

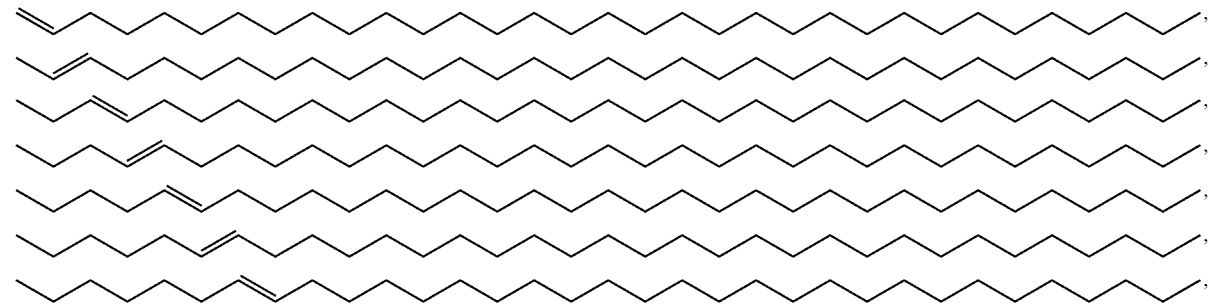

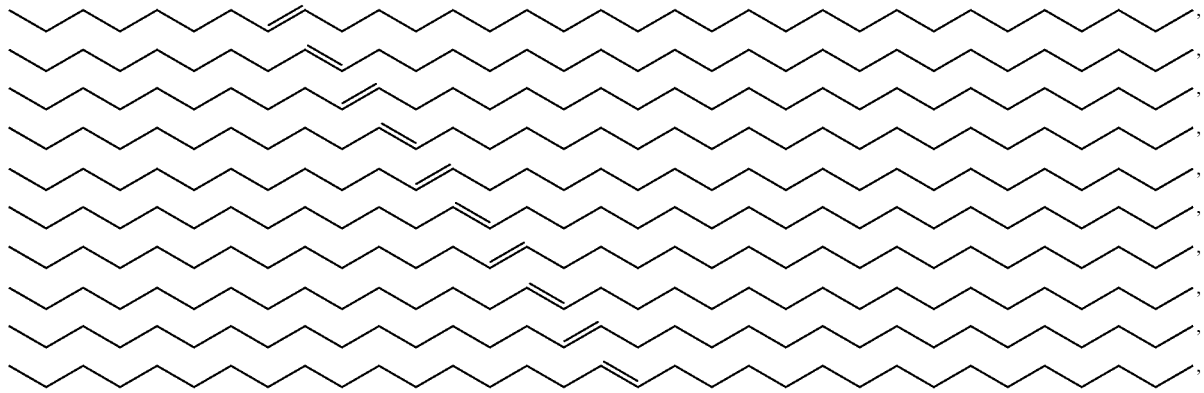

or agriculturally acceptable derivatives thereof.

56. The method of claim 54, wherein the tritriacontene is a cis-isomer.

57. The method of claim 56, wherein the tritriacontene is of the structure:

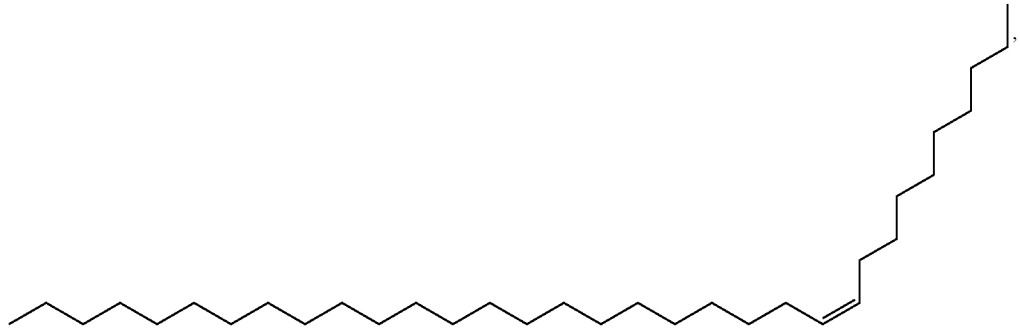 [SMILES: CCCCCCCCC/C=C\CCCCCCCCCCCCCCCCCCCCCC]

or an agriculturally acceptable derivative thereof.

58. A method for assessing the degree of hygienic behavior within a honey bee colony comprising:
   a. applying a tritriacontene composition to a set of capped hive cells;
   b. exposing the set of capped hive cells to a honey bee colony; and
   c. determining the amount of hive cells uncapped and subsequently recapped in the set of capped hive cells;
   wherein a higher amount of the set of hive cells that are uncapped and subsequently recapped is associated with a greater degree of hygienic behavior.

59. The method of claim 58, wherein the set of capped hive cells contains a diseased brood, diseased honey bees, or pests or parasites.

60. The method of claim 58, wherein the set of capped hive cells is empty.

61. The method of claim 58, wherein the tritriacontene composition comprises a tritriacontene and an agriculturally acceptable diluent or carrier, wherein the tritriacontene is in an effective amount for inducing hygienic behavior in honey bees.

62. The method of claim 61, wherein the tritriacontene is of the structure:

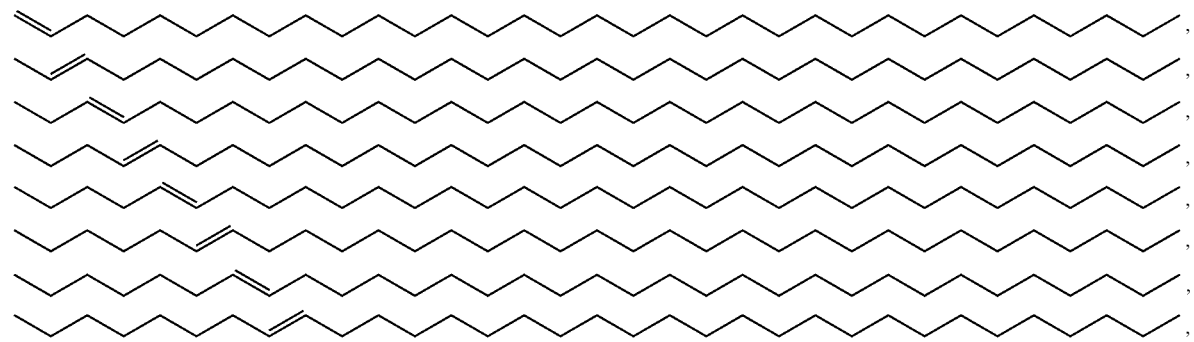

-continued
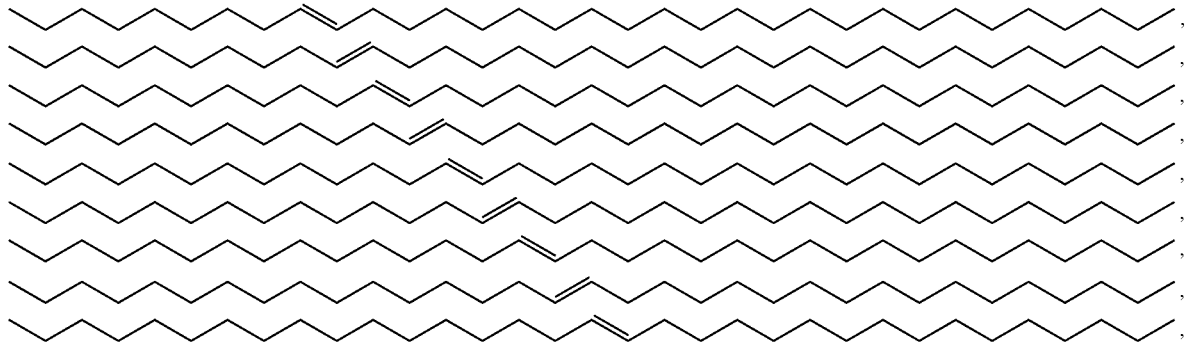
or agriculturally acceptable derivatives thereof.
63. The method of claim 61, wherein the tritriacontene is a cis-isomer.
64. The method of claim 63, wherein the tritriacontene is of the structure:
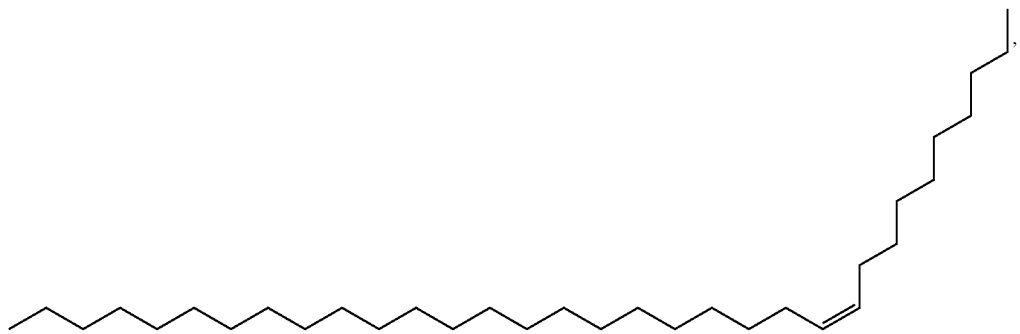 [SMILES: CCCCCCCCC/C=C\CCCCCCCCCCCCCCCCCCCCCC]
or an agriculturally acceptable derivative thereof.
* * * * *

UNITED STATES PATENT AND TRADEMARK OFFICE
CERTIFICATE OF CORRECTION

Page 1 of 1

PATENT NO. : 10,524,455 B2
APPLICATION NO. : 16/279432
DATED : January 7, 2020
INVENTOR(S) : Kaira Wagoner et al.

It is certified that error appears in the above-identified patent and that said Letters Patent is hereby corrected as shown below:

In the Claims

Claim 11 (at Column 72, Lines 41-43): each ':' should be changed to a -- ; --

Signed and Sealed this
Ninth Day of June, 2020

Andrei Iancu
*Director of the United States Patent and Trademark Office*

SEQUENCE LISTING

```
<160> NUMBER OF SEQ ID NOS: 6

<210> SEQ ID NO 1
<211> LENGTH: 20
<212> TYPE: RNA
```

```
<213> ORGANISM: Artificial sequence
<220> FEATURE:
<223> OTHER INFORMATION: DWV forward primer

<400> SEQUENCE: 1
gagattgaag cgcatgaaca                                            20

<210> SEQ ID NO 2
<211> LENGTH: 20
<212> TYPE: RNA
<213> ORGANISM: Artificial sequence
<220> FEATURE:
<223> OTHER INFORMATION: DWV reverse primer

<400> SEQUENCE: 2
tgaattcagt gtcgcccata                                            20

<210> SEQ ID NO 3
<211> LENGTH: 22
<212> TYPE: RNA
<213> ORGANISM: Artificial sequence
<220> FEATURE:
<223> OTHER INFORMATION: Actin forward primer

<400> SEQUENCE: 3
ttgtatgcca acactgtcct tt                                         22

<210> SEQ ID NO 4
<211> LENGTH: 20
<212> TYPE: RNA
<213> ORGANISM: Artificial sequence
<220> FEATURE:
<223> OTHER INFORMATION: Actin reverse primer

<400> SEQUENCE: 4
tggcgcgatg atcttaattt                                            20

<210> SEQ ID NO 5
<211> LENGTH: 22
<212> TYPE: RNA
<213> ORGANISM: Artificial sequence
<220> FEATURE:
<223> OTHER INFORMATION: RPSS forward primer

<400> SEQUENCE: 5
aattatttgg tcgctggaat tg                                         22

<210> SEQ ID NO 6
<211> LENGTH: 22
<212> TYPE: RNA
<213> ORGANISM: Artificial sequence
<220> FEATURE:
<223> OTHER INFORMATION: RPSS reverse primer

<400> SEQUENCE: 6
taacgtccag cagaatgtgg ta                                         22
```